(12) United States Patent
Desjarlais et al.

(10) Patent No.: US 7,459,527 B2
(45) Date of Patent: Dec. 2, 2008

(54) BMP-7 VARIANTS WITH IMPROVED PROPERTIES

(75) Inventors: John R. Desjarlais, Pasadena, CA (US); Shannon Alicia Marshall, San Francisco, CA (US); Jonathan Zalevsky, Riverside, CA (US)

(73) Assignee: Xencor, Inc., Monrovia, CA (US)

( * ) Notice: Subject to any disclaimer, the term of this patent is extended or adjusted under 35 U.S.C. 154(b) by 312 days.

(21) Appl. No.: 11/097,960

(22) Filed: Mar. 31, 2005

(65) Prior Publication Data

US 2006/0058231 A1 Mar. 16, 2006

Related U.S. Application Data

(60) Provisional application No. 60/558,189, filed on Mar. 31, 2004, provisional application No. 60/570,520, filed on May 11, 2004, provisional application No. 60/578,432, filed on Jun. 9, 2004, provisional application No. 60/587,464, filed on Jul. 13, 2004.

(51) Int. Cl.
*C07K 14/00* (2006.01)
*C07K 14/52* (2006.01)
*C12N 15/00* (2006.01)

(52) U.S. Cl. .................. 530/350; 530/351; 435/69.1; 435/69.5

(58) Field of Classification Search .................. None
See application file for complete search history.

(56) References Cited

U.S. PATENT DOCUMENTS 6,949,505 B1 * 9/2005 Rueger et al. ............ 514/2

OTHER PUBLICATIONS

Wharton et al., PNAS, 1991, vol. 88:9214-9218.*
Keller et al. (Nature Struct. Mol. Biol., 2004, vol. 11(5):481-488.*
Kirsch et al. (2000, EMBO J., vol. 19:3314-3324.*

* cited by examiner

*Primary Examiner*—Elizabeth C. Kemmerer
*Assistant Examiner*—Xiaozhen Xie
(74) *Attorney, Agent, or Firm*—Joyce Morrison; Kenton Abel

(57) ABSTRACT

The invention relates to variants of BMP-7 with improved properties and methods for their use.

2 Claims, 18 Drawing Sheets

Figure 1

| SEQ ID NO: | | |
|---|---|---|
| 71 | Cons: | CxxxxLYVxFxDxGWxDWIIAPxGYxAxYCxGxCxFPLxxxx N----xTNHAIxQ |
| 1 (Residues 14-114) | BMP-2: | CKRHPLYVDFSDVGWNDWIVAPPGYHAFYCHGECPFPLADHLN----STNHAIVQ |
| 72 | BMP-3: | CARRYLKVDFADIGWSEWIISPKSFDAYYCSGACQFPMPKSLK----PSNHATIQ |
| 73 | BMP-3b: | CSRRYLKVDFADIGWNEWIISPKSFDAYYCAGACEFPMPKIVR----PSNHATIQ |
| 2 (Residues 16-116) | BMP-4: | CRRHSLYVDFSDVGWNDWIVAPPGYQAFYCHGDCPFPLADHLN----STNHAIVQ |
| 3 (Residues 37-138) | BMP-5: | CKKHELYVSFRDLGWQDWIIAPEGYAAFYCDGECSFPLNAHMN----ATNHAIVQ |
| 4 (Residues 38-139) | BMP-6: | CRHELYVSFQDLGWQDWIIAPKGYAANYCDGECSFPLNAHMN----ATNHAIVQ |
| 5 (Residues 38-139) | BMP-7: | CRKHELYVSFRDLGWQDWIIAPEGYAAYYCEGECAFPLNSYMN----ATNHAIVQ |
| 6 (Residues 38-139) | BMP-8: | CKKHELYVSFQDLGWLDWVIAPQGYSAYYCEGECSFPLDSCMN----ATNHAILQ |
| 74 | BMP-9: | CQKTSLRVNFEDIGWDSWIIAPKEYEAYECKGGCPFPLADDVT----PTKHAIVQ |
| 75 | BMP-10: | CKRTPLYIDFKEIGWDSWIIAPPGYEAYECRGVCNYPLAEHLT----PTKHAIIQ |
| 76 | GDF-1: | CRARRLYVSFREVGWHRWVIAPRGFLANYCQGQCALPVALSGSGPPALNHAVLR |
| 77 | GDF-3: | CHRHQLFINFRDLGWHHKWIIAPKGFMANYCHGECPFSLTISLN----SSNYAFMQ |
| 78 | GDF-5: | CSRKALHVNFKDMGWDDWIIAPLEYEAFHCEGLCEFPLRSHLE----PTNHAVIQ |
| 79 | GDF-7: | CSRKPLHVDFKELGWDDWIIAPLDYEAYHCEGLCDFPLRSHLE----PTNHAIIQ |
| 80 | GDF-8: | CCRYPLTVDFEAFGWD-WIIAPKRYKANYCSGECEFVFLQKY----PHTHLVHQ |
| 81 | BMP-11: | CCRYPLTVDFEAFGWD-WIIAPKRYKANYCSGQCEYMFMQKY----PHTHLVQQ |
| 82 | BMP-15: | CSLHPFQISFRQLGWDHWIIAPPFYTPNYCKGTCLRVLRDGLN----SPNHAIIQ |
| 83 | BMP-16: | CRKVKFQVDFNLIGWSWIIYPKQYNAYRCEGECPNPVGEEFH----PTNHAYIQ |
| 71 | Cons: | TLVxxxxxxxxPKxCCxPTxLxAxSxLYxDxxxxVxLx-xYxxMxVxxCGCx |
| 1 (Residues 14-114) | BMP-2: | TLVNSVN--SKIPKACCVPTELSAISMLYLDENEKVVLK-NYQDMVVEGCGCR |
| 72 | BMP-3: | SIVRAVGVVPGIPEPCCVPEKMSSLSILFFDENKNVVLK-VYPNMTVESCACR |
| 73 | BMP-3b: | SIVRAVGIIPGIPEPCCVPDKMNSLGVLFLDENRNVVLK-VYPNMSVDTCACR |
| 2 (Residues 16-116) | BMP-4: | TLVNSVN--SSIPKACCVPTELSAISMLYLDEYDKVVLK-NYQEMVVEGCGCR |
| 3 (Residues 37-138) | BMP-5: | TLVHLMFP-DHVPKPCCAPTKLNAISVLYFDDSSNVILK-KYRNMVRSCGCH |
| 4 (Residues 38-139) | BMP-6: | TLVHLMNP-EYVPKPCCAPTKLNAISVLYFDDNSNVILK-KYRNMVRACGCH |
| 5 (Residues 38-139) | BMP-7: | TLVHFINP-DTVPKPCCAPTQLNAISVLYFDDSSNVILK-KYRNMVVRACGCH |
| 6 (Residues 38-139) | BMP-8: | SLVHLMKP-NAVPKACCAPTKLSATSVLYYDSSNNVILR-KHRNMVVXACGCH |
| 74 | BMP-9: | TLVHLKFP-TKVGKACCVPTKLSPISVLYLKDDMGVPTLK-HYEGMSVAECGCR |
| 75 | BMP-10: | ALVHLKNS-QKASKACCVPTKLEPISILYL-DKGVVTYKFYEGMAVSECGCR |
| 76 | GDF-1: | ALMHAAAP-GAADLPCCVPARLSPISVLFFDNSDPNVVLR-QYEDMVVDECGCR |
| 77 | GDF-3: | ALMHAVDP-E-IPQAVCIPTKLSPISMLYQDNNDNVILR-HYEDMVVDECGCG |
| 78 | GDF-5: | TLMNSMDP-ESTPPTCCVPTRLSPISILFIDSANNVVYK-QYEDMVVESCGCR |
| 79 | GDF-7: | TLLNSMAP-DRAPASCCVPARLSPISILYIDAANNVVYK-QYEDMVEACGCR |
| 80 | GDF-8: | A--NPRG--SAGP--CCTPTKMSPINMLYFNGKEQIIYG-KIPAMVDRCGCS |
| 81 | BMP-11: | A--NPRG--SAGP--CCTPTKMSPINMLYFNDKQQIIYG-KIPGMVDRCGSS |
| 82 | BMP-15: | NLINQLVD-QSVPRPSCVPYKYVPISVLMLEANGSILYK-EYEGMIAESCTCR |
| 83 | BMP-16: | SLLKRYQP-HRVFSTCCAPVKTKPLSMLYVDNG-RVLLDH-HKDMIVEECGCL |

Figure 3

| SEQ ID NO: | | |
|---|---|---|
| 7 | ALK2 : | lymcvceglscgned---hcegg-qcfsslsindgfh--vyqkgcfqvyeggkmtc |
| 8 | ALK3 : | FLKCYCSG-HCPDDAINNTCITNGHCFAIIEEDDQGETTLASGCMKYEGS-DFQC |
| 9 | ALK6 : | vlrckchh-hcpedsvnnicstdgyciftmieeddsglpvvtsgCLGLEGS-DFQC |
| 7 | ALK2 : | ktppspg--qaveccgg-dwcnrnitaql |
| 8 | ALK3 : | KDSPKAQLRRTIECCRT-NLCNQYLQPTL |
| 9 | ALK6 : | rdtpiphqrrsieccternecnkdlhptl |
| 10 | ActRIIa : | ETQECLFFNANWEKDRTNQTGVEPCYGDKDKRRHCFATWKNISGSIEIVKQGCW |
| 11 | ActRIIb : | ETRECIYYNANWELERTNQsGlErCeGeqDKRlHCyAsWaNsSGtIElVKkGCW |
| 12 | BMPRII : | fkdpyqgdlgigesrishengtilcskgst----cyglweksgkdinlvkqgcw |
| 10 | ActRIIa : | ---LDDINCYDRTDCvEKKDSP------EVYFCCCEGNMCNEKFSYFP |
| 11 | ActRIIb : | ---LDDfNCYDRqeCvateenP------qVYFCCCEGNfCNErFthlP |
| 12 | BMPRII : | shigdpqechy-eecvvttppsignqtyrfcccstdlcnvnftenf |

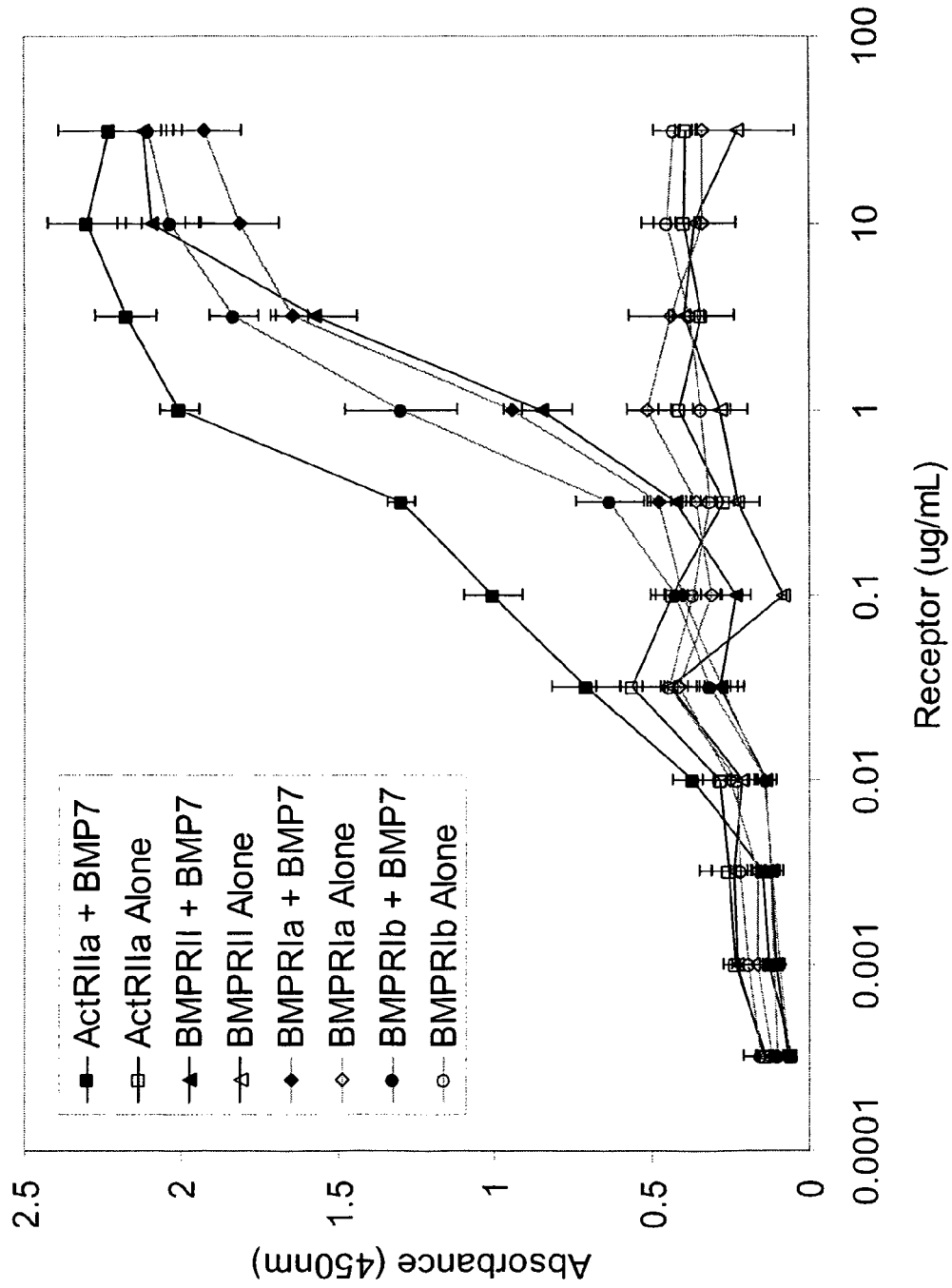

SEQUENCE LISTING

<160> NUMBER OF SEQ ID NOS: 87

<210> SEQ ID NO 1
<211> LENGTH: 114
<212> TYPE: PRT
<213> ORGANISM: Homo sapiens

<400> SEQUENCE: 1

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
```

85                  90                  95
Lys Val Val Leu Lys Asn Tyr Gln Asp Met Val Val Glu Gly Cys Gly
                100                 105                 110

Cys Arg

<210> SEQ ID NO 2
<211> LENGTH: 116
<212> TYPE: PRT
<213> ORGANISM: Homo sapiens

<400> SEQUENCE: 2

Ser Pro Lys His His Ser Gln Arg Ala Arg Lys Lys Asn Lys Asn Cys
1               5                   10                  15

Arg Arg His Ser Leu Tyr Val Asp Phe Ser Asp Val Gly Trp Asn Asp
                20                  25                  30

Trp Ile Val Ala Pro Pro Gly Tyr Gln Ala Phe Tyr Cys His Gly Asp
            35                  40                  45

Cys Pro Phe Pro Leu Ala Asp His Leu Asn Ser Thr Asn His Ala Ile
        50                  55                  60

Val Gln Thr Leu Val Asn Ser Val Asn Ser Ser Ile Pro Lys Ala Cys
65                  70                  75                  80

Cys Val Pro Thr Glu Leu Ser Ala Ile Ser Met Leu Tyr Leu Asp Glu
                85                  90                  95

Tyr Asp Lys Val Val Leu Lys Asn Tyr Gln Glu Met Val Val Glu Gly
                100                 105                 110

Cys Gly Cys Arg
        115

<210> SEQ ID NO 3
<211> LENGTH: 138
<212> TYPE: PRT
<213> ORGANISM: Homo sapiens

<400> SEQUENCE: 3

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser Glu
                20                  25                  30

Gln Lys Gln Ala Cys Lys Lys His Glu Leu Tyr Val Ser Phe Arg Asp
            35                  40                  45

Leu Gly Trp Gln Asp Trp Ile Ile Ala Pro Glu Gly Tyr Ala Ala Phe
        50                  55                  60

Tyr Cys Asp Gly Glu Cys Ser Phe Pro Leu Asn Ala His Met Asn Ala
65                  70                  75                  80

Thr Asn His Ala Ile Val Gln Thr Leu Val His Leu Met Phe Pro Asp
                85                  90                  95

His Val Pro Lys Pro Cys Cys Ala Pro Thr Lys Leu Asn Ala Ile Ser
                100                 105                 110

Val Leu Tyr Phe Asp Asp Ser Ser Asn Val Ile Leu Lys Lys Tyr Arg
            115                 120                 125

Asn Met Val Val Arg Ser Cys Gly Cys His
        130                 135

<210> SEQ ID NO 4
<211> LENGTH: 139
<212> TYPE: PRT
<213> ORGANISM: Homo sapiens

<400> SEQUENCE: 4

Ser Ala Ser Ser Arg Arg Gln Gln Ser Arg Asn Arg Ser Thr Gln
1               5                   10                  15

Ser Gln Asp Val Ala Arg Val Ser Ser Ala Ser Asp Tyr Asn Ser Ser
                20                  25                  30

Glu Leu Lys Thr Ala Cys Arg Lys His Glu Leu Tyr Val Ser Phe Gln
            35                  40                  45

Asp Leu Gly Trp Gln Asp Trp Ile Ile Ala Pro Lys Gly Tyr Ala Ala
        50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135

<210> SEQ ID NO 5
<211> LENGTH: 139
<212> TYPE: PRT
<213> ORGANISM: Homo sapiens

<400> SEQUENCE: 5

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
                20                  25                  30

Asp Gln Arg Gln Ala Cys Lys Lys His Glu Leu Tyr Val Ser Phe Arg
            35                  40                  45

Asp Leu Gly Trp Gln Asp Trp Ile Ile Ala Pro Glu Gly Tyr Ala Ala
        50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 6
<211> LENGTH: 139
<212> TYPE: PRT
<213> ORGANISM: Homo sapiens

<400> SEQUENCE: 6

Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
                20                  25                  30

```
His Gly Arg Gln Val Cys Arg Arg His Glu Leu Tyr Val Ser Phe Gln
            35                  40                  45

Asp Leu Gly Trp Leu Asp Trp Val Ile Ala Pro Gln Gly Tyr Ser Ala
 50                  55                  60

Tyr Tyr Cys Glu Gly Glu Cys Ser Phe Pro Leu Asp Ser Cys Met Asn
 65                  70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
                100                 105                 110

Ser Val Leu Tyr Tyr Asp Ser Ser Asn Asn Val Ile Leu Arg Lys His
                115                 120                 125

Arg Asn Met Val Val Lys Ala Cys Gly Cys His
                130                 135
```

<210> SEQ ID NO 7
<211> LENGTH: 76
<212> TYPE: PRT
<213> ORGANISM: Homo sapiens

<400> SEQUENCE: 7

```
Leu Tyr Met Cys Val Cys Glu Gly Leu Ser Cys Gly Asn Glu Asp His
 1               5                  10                  15

Cys Glu Gly Gln Gln Cys Phe Ser Ser Leu Ser Ile Asn Asp Gly Phe
                20                  25                  30

His Val Tyr Gln Lys Gly Cys Phe Gln Val Tyr Glu Gln Gly Lys Met
                35                  40                  45

Thr Cys Lys Thr Pro Pro Ser Pro Gly Gln Ala Val Glu Cys Cys Gln
 50                  55                  60

Gly Asp Trp Cys Asn Arg Asn Ile Thr Ala Gln Leu
 65                  70                  75
```

<210> SEQ ID NO 8
<211> LENGTH: 81
<212> TYPE: PRT
<213> ORGANISM: Homo sapiens

<400> SEQUENCE: 8

```
Phe Leu Lys Cys Tyr Cys Ser Gly His Cys Pro Asp Asp Ala Ile Asn
 1               5                  10                  15

Asn Thr Cys Ile Thr Asn Gly His Cys Phe Ala Ile Ile Glu Glu Asp
                20                  25                  30

Asp Gln Gly Glu Thr Thr Leu Ala Ser Gly Cys Met Lys Tyr Glu Gly
                35                  40                  45

Ser Asp Phe Gln Cys Lys Asp Ser Pro Lys Ala Gln Leu Arg Arg Thr
 50                  55                  60

Ile Glu Cys Cys Arg Thr Asn Leu Cys Asn Gln Tyr Leu Gln Pro Thr
 65                  70                  75                  80

Leu
```

<210> SEQ ID NO 9
<211> LENGTH: 82
<212> TYPE: PRT
<213> ORGANISM: Homo sapiens

<400> SEQUENCE: 9

```
Val Leu Arg Cys Lys Cys His His His Cys Pro Glu Asp Ser Val Asn
 1               5                  10                  15
```

```
Asn Ile Cys Ser Thr Asp Gly Tyr Cys Phe Thr Met Ile Glu Glu Asp
            20                  25                  30

Asp Ser Gly Leu Pro Val Val Thr Ser Gly Cys Leu Gly Leu Glu Gly
        35                  40                  45

Ser Asp Phe Gln Cys Arg Asp Thr Pro Ile Pro His Gln Arg Arg Ser
    50                  55                  60

Ile Glu Cys Cys Thr Glu Arg Asn Glu Cys Asn Lys Asp Leu His Pro
65                  70                  75                  80

Thr Leu

<210> SEQ ID NO 10
<211> LENGTH: 93
<212> TYPE: PRT
<213> ORGANISM: Homo sapiens

<400> SEQUENCE: 10

Glu Thr Gln Glu Cys Leu Phe Phe Asn Ala Asn Trp Glu Lys Asp Arg
1               5                   10                  15

Thr Asn Gln Thr Gly Val Glu Pro Cys Tyr Gly Asp Lys Asp Lys Arg
            20                  25                  30

Arg His Cys Phe Ala Thr Trp Lys Asn Ile Ser Gly Ser Ile Glu Ile
        35                  40                  45

Val Lys Gln Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Met Cys Asn Glu Lys Phe Ser Tyr Phe Pro
                85                  90

<210> SEQ ID NO 11
<211> LENGTH: 93
<212> TYPE: PRT
<213> ORGANISM: Homo sapiens

<400> SEQUENCE: 11

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro
                85                  90

<210> SEQ ID NO 12
<211> LENGTH: 96
<212> TYPE: PRT
<213> ORGANISM: Homo sapiens

<400> SEQUENCE: 12

Phe Lys Asp Pro Tyr Gln Gln Asp Leu Gly Ile Gly Glu Ser Arg Ile
1               5                   10                  15

Ser His Glu Asn Gly Thr Ile Leu Cys Ser Lys Gly Ser Thr Cys Tyr
```

-continued

```
                20                  25                  30
Gly Leu Trp Glu Lys Ser Lys Gly Asp Ile Asn Leu Val Lys Gln Gly
            35                  40                  45

Cys Trp Ser His Ile Gly Asp Pro Gln Glu Cys His Tyr Glu Glu Cys
        50                  55                  60

Val Val Thr Thr Thr Pro Pro Ser Ile Gln Asn Gly Thr Tyr Arg Phe
65                  70                  75                  80

Cys Cys Cys Ser Thr Asp Leu Cys Asn Val Asn Phe Thr Glu Asn Phe
                85                  90                  95
```

<210> SEQ ID NO 13
<211> LENGTH: 184
<212> TYPE: PRT
<213> ORGANISM: Homo sapiens

<400> SEQUENCE: 13

```
Met Ser Arg Thr Ala Tyr Thr Val Gly Ala Leu Leu Leu Leu Leu Gly
1               5                   10                  15

Thr Leu Leu Pro Ala Ala Glu Gly Lys Lys Lys Gly Ser Gln Gly Ala
                20                  25                  30

Ile Pro Pro Pro Asp Lys Ala Gln His Asn Asp Ser Glu Gln Thr Gln
            35                  40                  45

Ser Pro Gln Gln Pro Gly Ser Arg Asn Arg Gly Arg Gly Gln Gly Arg
        50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Lys Arg Val Thr Arg Val Lys Gln Cys
                165                 170                 175

Arg Cys Ile Ser Ile Asp Leu Asp
            180
```

<210> SEQ ID NO 14
<211> LENGTH: 232
<212> TYPE: PRT
<213> ORGANISM: Homo sapiens

<400> SEQUENCE: 14

```
Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
                20                  25                  30

Ile Arg Pro Ala Pro Ser Asp Asn Leu Pro Leu Val Asp Leu Ile Glu
            35                  40                  45

His Pro Asp Pro Ile Phe Asp Pro Lys Glu Lys Asp Leu Asn Glu Thr
        50                  55                  60

Leu Leu Arg Ser Leu Leu Gly Gly His Tyr Asp Pro Gly Phe Met Ala
```

```
            65                  70                  75                  80
Thr Ser Pro Pro Glu Asp Arg Pro Gly Gly Gly Gly Ala Ala Gly
                    85                  90                  95

Gly Ala Glu Asp Leu Ala Glu Leu Asp Gln Leu Leu Arg Gln Arg Pro
                100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Lys Leu Arg Arg Lys
        130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
                180                 185                 190

Lys Pro Ser Lys Ser Val His Leu Thr Val Leu Arg Trp Arg Cys Gln
            195                 200                 205

Arg Arg Gly Gly Gln Arg Cys Gly Trp Ile Pro Ile Gln Tyr Pro Ile
        210                 215                 220

Ile Ser Glu Cys Lys Cys Ser Cys
225                 230

<210> SEQ ID NO 15
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Xaa can be Aspartic Acid, Glutamic Acid,
      Glycine, Lysine, Asparagine, Arginine or Serine

<400> SEQUENCE: 15

Ser Thr Gly Gly Lys Gln Arg Ser Gln Asn Arg Ser Lys Thr Pro Lys
1               5                   10                  15

Asn Gln Glu Ala Xaa Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 16
<211> LENGTH: 139
<212> TYPE: PRT
<213> ORGANISM: Artificial
```

```
<220> FEATURE:
<223> OTHER INFORMATION: Synthetic
<220> FEATURE:
<221> NAME/KEY: misc_feature
<222> LOCATION: (23)..(23)
<223> OTHER INFORMATION: Xaa can be Aspartic Acid, Glycine, Lysine,
      Asparagine, Arginine or Serine

<400> SEQUENCE: 16
```

Ser Thr Gly Gly Lys Gln Arg Ser Gln Asn Arg Ser Lys Thr Pro Lys
1               5                   10                  15

Asn Gln Glu Ala Leu Arg Xaa Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

```
<210> SEQ ID NO 17
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Xaa can be Aspartic Acid, Glutamic Acid,
      Glycine, Lysine, Asparagine or Serine

<400> SEQUENCE: 17
```

Ser Thr Gly Gly Lys Gln Arg Ser Gln Asn Arg Ser Lys Thr Pro Lys
1               5                   10                  15

Asn Gln Glu Ala Leu Arg Met Ala Ser Xaa Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

```
<210> SEQ ID NO 18
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (36)..(36)
<223> OTHER INFORMATION: Xaa can be Glutamic Acid, Asparagine or
      Arginine

<400> SEQUENCE: 18

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Xaa Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 19
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (37)..(37)
<223> OTHER INFORMATION: Xaa can be Aspartic Acid, Glutamic Acid,
      Histidine, Lysine or Arginine

<400> SEQUENCE: 19

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Xaa Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
```

```
                    115                 120                 125

Arg Asn Met Val Val Arg Ala Cys Gly Cys His
        130                 135

<210> SEQ ID NO 20
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (39)..(39)
<223> OTHER INFORMATION: Xaa can be Alanine, Aspartic Acid, Glutamic
      Acid, Glycine, Asparagine, Arginine, Serine or Threonine

<400> SEQUENCE: 20

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Xaa Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
        130                 135

<210> SEQ ID NO 21
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (42)..(42)
<223> OTHER INFORMATION: Xaa can be Aspartic Acid, Glutamine, Arginine
      or Threonine

<400> SEQUENCE: 21

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Xaa Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95
```

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 22
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (44)..(44)
<223> OTHER INFORMATION: Xaa can be Alanine, Aspartic Acid, Glutamic
      Acid, Glycine, Histidine, Lysine, Asparagine, Proline, Glutamine,
      Arginine, Serine or Threonine

<400> SEQUENCE: 22

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Xaa Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 23
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (48)..(48)
<223> OTHER INFORMATION: Xaa can be Aspartic Acid, Glutamic Acid,
      Histidine, Lysine, Asparagine or Glutamine

<400> SEQUENCE: 23

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Xaa
        35                  40                  45

Asp Leu Gly Trp Gln Asp Trp Ile Ile Ala Pro Glu Gly Tyr Ala Ala
    50                  55                  60

```
Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
             85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 24
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (49)..(49)
<223> OTHER INFORMATION: Xaa can be Glutamic Acid or Serine

<400> SEQUENCE: 24

Ser Thr Gly Gly Lys Gln Arg Ser Gln Asn Arg Ser Lys Thr Pro Lys
  1               5                  10                  15

Asn Gln Glu Ala Leu Arg Met Ala Ser Val Ala Glu Asn Ser Ser Ser
             20                  25                  30

Asp Gln Arg Gln Ala Cys Lys Lys His Glu Leu Tyr Val Ser Phe Arg
             35                  40                  45

Xaa Leu Gly Trp Gln Asp Trp Ile Ile Ala Pro Glu Gly Tyr Ala Ala
 50                  55                  60

Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
             85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 25
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (52)..(52)
<223> OTHER INFORMATION: Xaa can be Alanine, Glutamic Acid, Lysine,
      Proline, Glutamine or Threonine

<400> SEQUENCE: 25

Ser Thr Gly Gly Lys Gln Arg Ser Gln Asn Arg Ser Lys Thr Pro Lys
  1               5                  10                  15

Asn Gln Glu Ala Leu Arg Met Ala Ser Val Ala Glu Asn Ser Ser Ser
             20                  25                  30

Asp Gln Arg Gln Ala Cys Lys Lys His Glu Leu Tyr Val Ser Phe Arg
```

```
                35                  40                  45
Asp Leu Gly Xaa Gln Asp Trp Ile Ile Ala Pro Glu Gly Tyr Ala Ala
         50                  55                  60
Tyr Tyr Cys Glu Gly Glu Cys Ala Phe Pro Leu Asn Ser Tyr Met Asn
 65                  70                  75                  80
Ala Thr Asn His Ala Ile Val Gln Thr Leu Val His Phe Ile Asn Pro
                 85                  90                  95
Asp Thr Val Pro Lys Pro Cys Cys Ala Pro Thr Gln Leu Asn Ala Ile
            100                 105                 110
Ser Val Leu Tyr Phe Asp Asp Ser Ser Asn Val Ile Leu Lys Lys Tyr
        115                 120                 125
Arg Asn Met Val Val Arg Ala Cys Gly Cys His
    130                 135
```

<210> SEQ ID NO 26
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (53)..(53)
<223> OTHER INFORMATION: Xaa can be Alanine, Aspartic Acid, Glutamic
      Acid, Glycine, Histidine, Lysine, Arginine, Serine or Threonine

<400> SEQUENCE: 26

```
Ser Thr Gly Gly Lys Gln Arg Ser Gln Asn Arg Ser Lys Thr Pro Lys
 1               5                  10                  15
Asn Gln Glu Ala Leu Arg Met Ala Ser Val Ala Glu Asn Ser Ser Ser
            20                  25                  30
Asp Gln Arg Gln Ala Cys Lys Lys His Glu Leu Tyr Val Ser Phe Arg
        35                  40                  45
Asp Leu Gly Trp Xaa Asp Trp Ile Ile Ala Pro Glu Gly Tyr Ala Ala
     50                 55                  60
Tyr Tyr Cys Glu Gly Glu Cys Ala Phe Pro Leu Asn Ser Tyr Met Asn
 65                  70                  75                  80
Ala Thr Asn His Ala Ile Val Gln Thr Leu Val His Phe Ile Asn Pro
                85                  90                  95
Asp Thr Val Pro Lys Pro Cys Cys Ala Pro Thr Gln Leu Asn Ala Ile
            100                 105                 110
Ser Val Leu Tyr Phe Asp Asp Ser Ser Asn Val Ile Leu Lys Lys Tyr
        115                 120                 125
Arg Asn Met Val Val Arg Ala Cys Gly Cys His
    130                 135
```

<210> SEQ ID NO 27
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (54)..(54)
<223> OTHER INFORMATION: Xaa can be Lysine, Asparagine, Arginine or
      Serine

<400> SEQUENCE: 27

```
Ser Thr Gly Gly Lys Gln Arg Ser Gln Asn Arg Ser Lys Thr Pro Lys
 1               5                  10                  15
```

```
Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Xaa Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 28
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (55)..(55)
<223> OTHER INFORMATION: Xaa can be Alanine, Glutamic Acid, Histidine,
      Lysine, Asparagine, Proline, Glutamine, Arginine or Threonine

<400> SEQUENCE: 28

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Xaa Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 29
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (57)..(57)
<223> OTHER INFORMATION: Xaa can be Alanine, Aspartic Acid, Glutamic
      Acid, Histidine, Lysine, Leucine, Proline, Glutamine, Threonine or
```

Valine

<400> SEQUENCE: 29

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Xaa Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 30
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (60)..(60)
<223> OTHER INFORMATION: Xaa can be Histidine, Lysine, Asparagine,
      Proline, Glutamine, Arginine, Serine or Threonine

<400> SEQUENCE: 30

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Xaa Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 31
<211> LENGTH: 139
<212> TYPE: PRT
<213> ORGANISM: Artificial
<220> FEATURE:

```
<223> OTHER INFORMATION: Synthetic
<220> FEATURE:
<221> NAME/KEY: misc_feature
<222> LOCATION: (63)..(63)
<223> OTHER INFORMATION: Xaa can be Glutamic Acid, Glutamine, Arginine
      or Serine

<400> SEQUENCE: 31

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Xaa Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 32
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (65)..(65)
<223> OTHER INFORMATION: Xaa can be Aspartic Acid, Glutamic Acid or
      Asparagine

<400> SEQUENCE: 32

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Xaa Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

```
<210> SEQ ID NO 33
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (70)..(70)
<223> OTHER INFORMATION: Xaa can be Alanine or Glutamine

<400> SEQUENCE: 33

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Xaa Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 34
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (72)..(72)
<223> OTHER INFORMATION: Xaa can be Aspartic Acid, Glutamic Acid,
      Histidine, Lysine, Asparagine, Arginine or Serine

<400> SEQUENCE: 34

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Xaa Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125
```

Arg Asn Met Val Val Arg Ala Cys Gly Cys His
    130                 135

<210> SEQ ID NO 35
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (73)..(73)
<223> OTHER INFORMATION: Xaa can be Alanine, Aspartic Acid, Glutamic
      Acid, Glycine, Histidine, Lysine, Asparagine, Glutamine, Arginine,
      Serine or Threonine

<400> SEQUENCE: 35

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Xaa Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 36
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (76)..(76)
<223> OTHER INFORMATION: Xaa can be Alanine, Aspartic Acid, Asparagine,
      Serine, Threonine or Tyrosine

<400> SEQUENCE: 36

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Xaa Ser Tyr Met Asn
65                  70                  75                  80

Ala Thr Asn His Ala Ile Val Gln Thr Leu Val His Phe Ile Asn Pro
                85                  90                  95

```
Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 37
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (77)..(77)
<223> OTHER INFORMATION: Xaa can be Alanine, Aspartic Acid, Glutamic
      Acid, Histidine, Lysine, Asparagine, Proline, Glutamine or
      Threonine

```
<400> SEQUENCE: 37

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Xaa Tyr Met Asn
65                  70                  75                  80

Ala Thr Asn His Ala Ile Val Gln Thr Leu Val His Phe Ile Asn Pro
            85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 38
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (78)..(78)
<223> OTHER INFORMATION: Xaa can be Aspartic Acid, Glycine, Histidine,
      Asparagine, Proline, Arginine, Serine or Threonine

```
<400> SEQUENCE: 38

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60
```

```
Tyr Tyr Cys Glu Gly Glu Cys Ala Phe Pro Leu Asn Ser Xaa Met Asn
 65                  70                  75                  80

Ala Thr Asn His Ala Ile Val Gln Thr Leu Val His Phe Ile Asn Pro
             85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 39
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (80)..(80)
<223> OTHER INFORMATION: Xaa can be Aspartic Acid, Glutamine, Serine or
      Threonine

<400> SEQUENCE: 39

Ser Thr Gly Gly Lys Gln Arg Ser Gln Asn Arg Ser Lys Thr Pro Lys
  1               5                  10                  15

Asn Gln Glu Ala Leu Arg Met Ala Ser Val Ala Glu Asn Ser Ser Ser
             20                  25                  30

Asp Gln Arg Gln Ala Cys Lys Lys His Glu Leu Tyr Val Ser Phe Arg
         35                  40                  45

Asp Leu Gly Trp Gln Asp Trp Ile Ile Ala Pro Glu Gly Tyr Ala Ala
     50                  55                  60

Tyr Tyr Cys Glu Gly Glu Cys Ala Phe Pro Leu Asn Ser Tyr Met Xaa
 65                  70                  75                  80

Ala Thr Asn His Ala Ile Val Gln Thr Leu Val His Phe Ile Asn Pro
             85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 40
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (82)..(82)
<223> OTHER INFORMATION: Xaa can be Valine

<400> SEQUENCE: 40

Ser Thr Gly Gly Lys Gln Arg Ser Gln Asn Arg Ser Lys Thr Pro Lys
  1               5                  10                  15

Asn Gln Glu Ala Leu Arg Met Ala Ser Val Ala Glu Asn Ser Ser Ser
             20                  25                  30

Asp Gln Arg Gln Ala Cys Lys Lys His Glu Leu Tyr Val Ser Phe Arg
         35                  40                  45
```

```
Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
 65              70                  75                  80

Ala Xaa Asn His Ala Ile Val Gln Thr Leu Val His Phe Ile Asn Pro
            85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 41
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (83)..(83)
<223> OTHER INFORMATION: Xaa can be Proline

<400> SEQUENCE: 41

```
Ser Thr Gly Gly Lys Gln Arg Ser Gln Asn Arg Ser Lys Thr Pro Lys
 1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
 65              70                  75                  80

Ala Thr Xaa His Ala Ile Val Gln Thr Leu Val His Phe Ile Asn Pro
            85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 42
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (86)..(86)
<223> OTHER INFORMATION: Xaa can be Alanine, Aspartic Acid, Glutamic
      Acid, Lysine, Proline, Glutamine or Threonine

<400> SEQUENCE: 42

```
Ser Thr Gly Gly Lys Gln Arg Ser Gln Asn Arg Ser Lys Thr Pro Lys
 1               5                   10                  15

Asn Gln Glu Ala Leu Arg Met Ala Ser Val Ala Glu Asn Ser Ser Ser
```

```
                    20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Xaa Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
        130                 135

<210> SEQ ID NO 43
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (88)..(88)
<223> OTHER INFORMATION: Xaa can be Glutamic Acid

<400> SEQUENCE: 43

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
                20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Xaa Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
        130                 135

<210> SEQ ID NO 44
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (90)..(90)
<223> OTHER INFORMATION: Xaa can be Glutamic Acid, Glycine, Histidine,
      Lysine, Asparagine, Proline, Glutamine, Arginine, Serine or
      Threonine

<400> SEQUENCE: 44
```

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65              70                  75                  80

Ala Thr Asn His Ala Ile Val Gln Thr Xaa Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 45
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (93)..(93)
<223> OTHER INFORMATION: Xaa can be Alanine, Aspartic Acid, Glutamic
      Acid, Glycine, Histidine, Proline, Glutamine, Arginine, Serine or
      Threonine

<400> SEQUENCE: 45

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65              70                  75                  80

Ala Thr Asn His Ala Ile Val Gln Thr Leu Val His Xaa Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 46
<211> LENGTH: 139
<212> TYPE: PRT
<213> ORGANISM: Artificial
<220> FEATURE:
<223> OTHER INFORMATION: Synthetic
<220> FEATURE:

```
<221> NAME/KEY: misc_feature
<222> LOCATION: (94)..(94)
<223> OTHER INFORMATION: Xaa can be Alanine, Glutamic Acid, Histidine,
      Lysine, Proline, Glutamine, Arginine or Threonine

<400> SEQUENCE: 46
```

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Xaa Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

```
<210> SEQ ID NO 47
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (95)..(95)
<223> OTHER INFORMATION: Xaa can be Aspartic Acid, Lysine, Glutamine or
      Arginine

<400> SEQUENCE: 47
```

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Xaa Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

```
<210> SEQ ID NO 48
<211> LENGTH: 139
```

```
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (97)..(97)
<223> OTHER INFORMATION: Xaa can be Aspartic Acid, Lysine or Arginine

<400> SEQUENCE: 48

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Xaa Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 49
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (98)..(98)
<223> OTHER INFORMATION: Xaa can be Alanine, Glutamic Acid, Lysine,
      Arginine or a deletion

<400> SEQUENCE: 49

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Xaa Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 50
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (105)..(105)
<223> OTHER INFORMATION: Xaa can be Valine

<400> SEQUENCE: 50

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Xaa Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 51
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be Aspartic Acid, Lysine or Serine

<400> SEQUENCE: 51

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Xaa Leu Asn Ala Ile
            100                 105                 110

Ser Val Leu Tyr Phe Asp Asp Ser Ser Asn Val Ile Leu Lys Lys Tyr
        115                 120                 125
```

```
Arg Asn Met Val Val Arg Ala Cys Gly Cys His
    130                 135

<210> SEQ ID NO 52
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (110)..(110)
<223> OTHER INFORMATION: Xaa can be Aspartic Acid, Glutamic Acid or
      Histidine

<400> SEQUENCE: 52

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Xaa Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 53
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (111)..(111)
<223> OTHER INFORMATION: Xaa can be Aspartic Acid or Serine

<400> SEQUENCE: 53

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Xaa Ile
```

```
                    100                 105                 110
Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 54
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (115)..(115)
<223> OTHER INFORMATION: Xaa can be Alanine, Glutamic Acid, Lysine,
      Glutamine or Threonine

<400> SEQUENCE: 54

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Xaa Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 55
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (116)..(116)
<223> OTHER INFORMATION: Xaa can be Alanine, Aspartic Acid, Glutamic
      Acid, Histidine, Lysine, Glutamine, Serine or Threonine

<400> SEQUENCE: 55

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80
```

```
Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Xaa Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 56
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (117)..(117)
<223> OTHER INFORMATION: Xaa can be Alanine, Aspartic Acid, Glutamic
      Acid, Histidine, Lysine, Glutamine, Arginine, Serine or Tyrosine

<400> SEQUENCE: 56

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Xaa Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 57
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (119)..(119)
<223> OTHER INFORMATION: Xaa can be Glutamic Acid, Asparagine, Serine or
      Threonine

<400> SEQUENCE: 57

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45
```

```
Asp Leu Gly Trp Gln Asp Trp Ile Ile Ala Pro Glu Gly Tyr Ala Ala
         50                  55                  60

Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
                 85                  90                  95

Asp Thr Val Pro Lys Pro Cys Cys Ala Pro Thr Gln Leu Asn Ala Ile
            100                 105                 110

Ser Val Leu Tyr Phe Asp Xaa Ser Asn Val Ile Leu Lys Lys Tyr
        115                 120                 125

Arg Asn Met Val Val Arg Ala Cys Gly Cys His
        130                 135
```

<210> SEQ ID NO 58
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (120)..(120)
<223> OTHER INFORMATION: Xaa can be Aspartic Acid, Glutamic Acid,
      Asparagine or Arginine

<400> SEQUENCE: 58

```
Ser Thr Gly Gly Lys Gln Arg Ser Gln Asn Arg Ser Lys Thr Pro Lys
 1               5                  10                  15

Asn Gln Glu Ala Leu Arg Met Ala Ser Val Ala Glu Asn Ser Ser Ser
             20                  25                  30

Asp Gln Arg Gln Ala Cys Lys Lys His Glu Leu Tyr Val Ser Phe Arg
         35                  40                  45

Asp Leu Gly Trp Gln Asp Trp Ile Ile Ala Pro Glu Gly Tyr Ala Ala
         50                  55                  60

Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
                 85                  90                  95

Asp Thr Val Pro Lys Pro Cys Cys Ala Pro Thr Gln Leu Asn Ala Ile
            100                 105                 110

Ser Val Leu Tyr Phe Asp Asp Xaa Ser Asn Val Ile Leu Lys Lys Tyr
        115                 120                 125

Arg Asn Met Val Val Arg Ala Cys Gly Cys His
        130                 135
```

<210> SEQ ID NO 59
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (121)..(121)
<223> OTHER INFORMATION: Xaa can be Aspartic Acid, Glutamic Acid,
      Lysine, Asparagine or Threonine

<400> SEQUENCE: 59

```
Ser Thr Gly Gly Lys Gln Arg Ser Gln Asn Arg Ser Lys Thr Pro Lys
 1               5                  10                  15

Asn Gln Glu Ala Leu Arg Met Ala Ser Val Ala Glu Asn Ser Ser Ser
```

```
                    20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Xaa Asn Val Ile Leu Lys Lys Tyr
            115                 120                 125

Arg Asn Met Val Val Arg Ala Cys Gly Cys His
            130                 135

<210> SEQ ID NO 60
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (122)..(122)
<223> OTHER INFORMATION: Xaa can be Glutamic Acid, Glutamine or Arginine

<400> SEQUENCE: 60

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
                20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Xaa Val Ile Leu Lys Lys Tyr
            115                 120                 125

Arg Asn Met Val Val Arg Ala Cys Gly Cys His
            130                 135

<210> SEQ ID NO 61
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (123)..(123)
<223> OTHER INFORMATION: Xaa can be Alanine, Aspartic Acid, Glycine,
      Asparagine, Arginine or Threonine

<400> SEQUENCE: 61
```

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65              70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Xaa Ile Leu Lys Lys Tyr
        115                 120                 125

Arg Asn Met Val Val Arg Ala Cys Gly Cys His
        130                 135

<210> SEQ ID NO 62
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (125)..(125)
<223> OTHER INFORMATION: Xaa can be Alanine, Glutamic Acid, Lysine,
      Proline, Glutamine, Threonine or Tyrosine

<400> SEQUENCE: 62

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65              70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Xaa Lys Lys Tyr
        115                 120                 125

Arg Asn Met Val Val Arg Ala Cys Gly Cys His
        130                 135

<210> SEQ ID NO 63
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (126)..(126)
```

<223> OTHER INFORMATION: Xaa can be Aspartic Acid, Glutamic Acid, Glycine, Glutamine or Arginine

<400> SEQUENCE: 63

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Xaa Lys Tyr
        115                 120                 125

Arg Asn Met Val Val Arg Ala Cys Gly Cys His
    130                 135
```

<210> SEQ ID NO 64
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (127)..(127)
<223> OTHER INFORMATION: Xaa can be Alanine, Aspartic Acid, Glutamic Acid, Histidine, Asparagine, Proline, Glutamine, Serine, Threonine or Tyrosine

<400> SEQUENCE: 64

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Xaa Tyr
        115                 120                 125

Arg Asn Met Val Val Arg Ala Cys Gly Cys His
    130                 135
```

<210> SEQ ID NO 65
<211> LENGTH: 139
<212> TYPE: PRT

```
<213> ORGANISM: Artificial
<220> FEATURE:
<223> OTHER INFORMATION: Synthetic
<220> FEATURE:
<221> NAME/KEY: misc_feature
<222> LOCATION: (128)..(128)
<223> OTHER INFORMATION: Xaa can be Aspartic Acid, Glutamic Acid,
      Histidine, Lysine or Glutamine

<400> SEQUENCE: 65

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Xaa
        115                 120                 125

Arg Asn Met Val Val Arg Ala Cys Gly Cys His
    130                 135

<210> SEQ ID NO 66
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (129)..(129)
<223> OTHER INFORMATION: Xaa can be Aspartic Acid, Glutamic Acid,
      Lysine, Asparagine or Serine

<400> SEQUENCE: 66

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Xaa Asn Met Val Val Arg Ala Cys Gly Cys His
    130                 135
```

<210> SEQ ID NO 67
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (130)..(130)
<223> OTHER INFORMATION: Xaa can be Aspartic Acid

<400> SEQUENCE: 67

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Xaa Met Val Val Arg Ala Cys Gly Cys His
    130                 135

<210> SEQ ID NO 68
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (134)..(134)
<223> OTHER INFORMATION: Xaa can be Aspartic Acid, Glutamic Acid,
      Lysine, Leucine, Proline, Glutamine, Arginine or Serine

<400> SEQUENCE: 68

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr

```
                115                 120                 125
Arg Asn Met Val Val Xaa Ala Cys Gly Cys His
    130                 135

<210> SEQ ID NO 69
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (135)..(135)
<223> OTHER INFORMATION: Xaa can be Aspartic Acid, Glutamic Acid or
      Serine

<400> SEQUENCE: 69

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Xaa Cys Gly Cys His
    130                 135

<210> SEQ ID NO 70
<211> LENGTH: 139
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (139)..(139)
<223> OTHER INFORMATION: Xaa can be Arginine

<400> SEQUENCE: 70

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95
```

```
Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys Xaa
        130                 135

<210> SEQ ID NO 71
<211> LENGTH: 103
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (55)..(63)
<223> OTHER INFORMATION: Xaa can be any naturally occurring amino acid
<220> FEATURE:
<221> NAME/KEY: misc_feature
<222> LOCATION: (66)..(66)
```

```
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (83)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid

<400> SEQUENCE: 71

Cys Xaa Xaa Xaa Xaa Leu Tyr Val Xaa Phe Xaa Asp Xaa Gly Trp Xaa
1               5                   10                  15

Asp Trp Ile Ile Ala Pro Xaa Gly Tyr Xaa Ala Xaa Tyr Cys Xaa Gly
            20                  25                  30

Xaa Cys Xaa Phe Pro Leu Xaa Xaa Xaa Xaa Asn Xaa Thr Asn His Ala
        35                  40                  45

Ile Xaa Gln Thr Leu Val Xaa Xaa Xaa Xaa Xaa Xaa Xaa Xaa Xaa Pro
    50                  55                  60

Lys Xaa Cys Cys Xaa Pro Thr Xaa Leu Xaa Ala Xaa Ser Xaa Leu Tyr
65                  70                  75                  80

Xaa Asp Xaa Xaa Xaa Xaa Val Xaa Leu Xaa Xaa Tyr Xaa Xaa Met Xaa
                85                  90                  95

Val Xaa Xaa Cys Gly Cys Xaa
            100

<210> SEQ ID NO 72
```

```
<211> LENGTH: 103
<212> TYPE: PRT
<213> ORGANISM: Homo sapiens

<400> SEQUENCE: 72

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
        35                  40                  45

Thr Ile Gln Ser Ile Val Arg Ala Val Gly Val Pro Gly Ile Pro
    50                  55                  60

Glu Pro Cys Cys Val Pro Glu Lys Met Ser Ser Leu Ser Ile Leu Phe
65                  70                  75                  80

Phe Asp Glu Asn Lys Asn Val Val Leu Lys Val Tyr Pro Asn Met Thr
                85                  90                  95

Val Glu Ser Cys Ala Cys Arg
            100

<210> SEQ ID NO 73
<211> LENGTH: 103
<212> TYPE: PRT
<213> ORGANISM: Homo sapiens

<400> SEQUENCE: 73

Cys Ser Arg Arg Tyr Leu Lys Val Asp Phe Ala Asp Ile Gly Trp Asn
1               5                   10                  15

Glu Trp Ile Ile Ser Pro Lys Ser Phe Asp Ala Tyr Tyr Cys Ala Gly
            20                  25                  30

Ala Cys Glu Phe Pro Met Pro Lys Ile Val Arg Pro Ser Asn His Ala
        35                  40                  45

Thr Ile Gln Ser Ile Val Arg Ala Val Gly Ile Ile Pro Gly Ile Pro
    50                  55                  60

Glu Pro Cys Cys Val Pro Asp Lys Met Asn Ser Leu Gly Val Leu Phe
65                  70                  75                  80

Leu Asp Glu Asn Arg Asn Val Val Leu Lys Val Tyr Pro Asn Met Ser
                85                  90                  95

Val Asp Thr Cys Ala Cys Arg
            100

<210> SEQ ID NO 74
<211> LENGTH: 103
<212> TYPE: PRT
<213> ORGANISM: Homo sapiens

<400> SEQUENCE: 74

Cys Gln Lys Thr Ser Leu Arg Val Asn Phe Glu Asp Ile Gly Trp Asp
1               5                   10                  15

Ser Trp Ile Ile Ala Pro Lys Glu Tyr Glu Ala Tyr Glu Cys Lys Gly
            20                  25                  30

Gly Cys Phe Phe Pro Leu Ala Asp Asp Val Thr Pro Thr Lys His Ala
        35                  40                  45

Ile Val Gln Thr Leu Val His Leu Lys Phe Pro Thr Lys Val Gly Lys
    50                  55                  60

Ala Cys Cys Val Pro Thr Lys Leu Ser Pro Ile Ser Val Leu Tyr Lys
65                  70                  75                  80
```

```
Asp Asp Met Gly Val Pro Thr Leu Lys Tyr His Tyr Glu Gly Met Ser
                85                  90                  95
Val Ala Glu Cys Gly Cys Arg
            100

<210> SEQ ID NO 75
<211> LENGTH: 102
<212> TYPE: PRT
<213> ORGANISM: Homo sapiens

<400> SEQUENCE: 75

Cys Lys Arg Thr Pro Leu Tyr Ile Asp Phe Lys Glu Ile Gly Trp Asp
1               5                   10                  15
Ser Trp Ile Ile Ala Pro Pro Gly Tyr Glu Ala Tyr Glu Cys Arg Gly
            20                  25                  30
Val Cys Asn Tyr Pro Leu Ala Glu His Leu Thr Pro Thr Lys His Ala
        35                  40                  45
Ile Ile Gln Ala Leu Val His Leu Lys Asn Ser Gln Lys Ala Ser Lys
    50                  55                  60
Ala Cys Cys Val Pro Thr Lys Leu Glu Pro Ile Ser Ile Leu Tyr Leu
65                  70                  75                  80
Asp Lys Gly Val Val Thr Tyr Lys Phe Lys Tyr Glu Gly Met Ala Val
                85                  90                  95
Ser Glu Cys Gly Cys Arg
            100

<210> SEQ ID NO 76
<211> LENGTH: 106
<212> TYPE: PRT
<213> ORGANISM: Homo sapiens

<400> SEQUENCE: 76

Cys Arg Ala Arg Arg Leu Tyr Val Ser Phe Arg Glu Val Gly Trp His
1               5                   10                  15
Arg Trp Val Ile Ala Pro Arg Gly Phe Leu Ala Asn Tyr Cys Gln Gly
            20                  25                  30
Gln Cys Ala Leu Pro Val Ala Leu Ser Gly Ser Gly Gly Pro Pro Ala
        35                  40                  45
Leu Asn His Ala Val Leu Arg Ala Leu Met His Ala Ala Ala Pro Gly
    50                  55                  60
Ala Ala Asp Leu Pro Cys Cys Val Pro Ala Arg Leu Ser Pro Ile Ser
65                  70                  75                  80
Val Leu Phe Phe Asp Asn Ser Asp Asn Val Val Leu Arg Gln Tyr Glu
                85                  90                  95
Asp Met Val Val Asp Glu Cys Gly Cys Arg
            100                 105

<210> SEQ ID NO 77
<211> LENGTH: 101
<212> TYPE: PRT
<213> ORGANISM: Homo sapiens

<400> SEQUENCE: 77

Cys His Arg His Gln Leu Phe Ile Asn Phe Arg Asp Leu Gly Trp His
1               5                   10                  15
Lys Trp Ile Ile Ala Pro Lys Gly Phe Met Ala Asn Tyr Cys His Gly
            20                  25                  30
Glu Cys Pro Phe Ser Leu Thr Ile Ser Leu Asn Ser Ser Asn Tyr Ala
```

```
                35                  40                  45
Phe Met Gln Ala Leu Met His Ala Val Asp Pro Glu Ile Pro Gln Ala
            50                  55                  60

Val Cys Ile Pro Thr Lys Leu Ser Pro Ile Ser Met Leu Tyr Gln Asp
 65                  70                  75                  80

Asn Asn Asp Asn Val Ile Leu Arg His Tyr Glu Asp Met Val Val Asp
                85                  90                  95

Glu Cys Gly Cys Gly
            100

<210> SEQ ID NO 78
<211> LENGTH: 102
<212> TYPE: PRT
<213> ORGANISM: Homo sapiens

<400> SEQUENCE: 78

Cys Ser Arg Lys Ala Leu His Val Asn Phe Lys Asp Met Gly Trp Asp
 1               5                  10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
 65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 79
<211> LENGTH: 102
<212> TYPE: PRT
<213> ORGANISM: Homo sapiens

<400> SEQUENCE: 79

Cys Ser Arg Lys Pro Leu His Val Asp Phe Lys Glu Leu Gly Trp Asp
 1               5                  10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 80
<211> LENGTH: 95
<212> TYPE: PRT
<213> ORGANISM: Homo sapiens

<400> SEQUENCE: 80
```

-continued

Cys Cys Arg Tyr Pro Leu Thr Val Asp Phe Glu Ala Phe Gly Trp Asp
1               5                   10                  15

Trp Ile Ile Ala Pro Lys Arg Tyr Lys Ala Asn Tyr Cys Ser Gly Glu
                20                  25                  30

Cys Glu Phe Val Phe Leu Gln Lys Tyr Pro His Thr His Leu Val His
            35                  40                  45

Gln Ala Asn Pro Arg Gly Ser Ala Gly Pro Cys Cys Thr Pro Thr Lys
        50                  55                  60

Met Ser Pro Ile Asn Met Leu Tyr Phe Asn Gly Lys Glu Gln Ile Ile
65                  70                  75                  80

Tyr Gly Lys Ile Pro Ala Met Val Val Asp Arg Cys Gly Cys Ser
                85                  90                  95

<210> SEQ ID NO 81
<211> LENGTH: 95
<212> TYPE: PRT
<213> ORGANISM: Homo sapiens

<400> SEQUENCE: 81

Cys Cys Arg Tyr Pro Leu Thr Val Asp Phe Glu Ala Phe Gly Trp Asp
1               5                   10                  15

Trp Ile Ile Ala Pro Lys Arg Tyr Lys Ala Asn Tyr Cys Ser Gly Gln
                20                  25                  30

Cys Glu Tyr Met Phe Met Gln Lys Tyr Pro His Thr His Leu Val Gln
            35                  40                  45

Gln Ala Asn Pro Arg Gly Ser Ala Gly Pro Cys Cys Thr Pro Thr Lys
        50                  55                  60

Met Ser Pro Ile Asn Met Leu Tyr Phe Asn Asp Lys Gln Gln Ile Ile
65                  70                  75                  80

Tyr Gly Lys Ile Pro Gly Met Val Val Asp Arg Cys Gly Cys Ser
                85                  90                  95

<210> SEQ ID NO 82
<211> LENGTH: 102
<212> TYPE: PRT
<213> ORGANISM: Homo sapiens

<400> SEQUENCE: 82

Cys Ser Leu His Pro Phe Gln Ile Ser Phe Arg Gln Leu Gly Trp Asp
1               5                   10                  15

His Trp Ile Ile Ala Pro Pro Phe Tyr Thr Pro Asn Tyr Cys Lys Gly
                20                  25                  30

Thr Cys Leu Arg Val Leu Arg Asp Gly Leu Asn Ser Pro Asn His Ala
            35                  40                  45

Ile Ile Gln Asn Leu Ile Asn Gln Leu Val Asp Gln Ser Val Pro Arg
        50                  55                  60

Pro Ser Cys Val Pro Tyr Lys Tyr Val Pro Ile Ser Val Leu Met Ile
65                  70                  75                  80

Glu Ala Asn Gly Ser Ile Leu Tyr Lys Glu Tyr Glu Gly Met Ile Ala
                85                  90                  95

Glu Ser Cys Thr Cys Arg
                100

<210> SEQ ID NO 83
<211> LENGTH: 101
<212> TYPE: PRT
<213> ORGANISM: Homo sapiens

```
<400> SEQUENCE: 83

Cys Arg Lys Val Lys Phe Gln Val Asp Phe Asn Leu Ile Gly Trp Gly
1               5                   10                  15

Ser Trp Ile Ile Tyr Pro Lys Gln Tyr Asn Ala Tyr Arg Cys Glu Gly
                20                  25                  30

Glu Cys Pro Asn Pro Val Gly Glu Glu Phe His Pro Thr Asn His Ala
            35                  40                  45

Tyr Ile Gln Ser Leu Leu Lys Arg Tyr Gln Pro His Arg Val Pro Ser
        50                  55                  60

Thr Cys Cys Ala Pro Val Lys Thr Lys Pro Leu Ser Met Leu Tyr Val
65                  70                  75                  80

Asp Asn Gly Arg Val Leu Leu Asp His His Lys Asp Met Ile Val Glu
                85                  90                  95

Glu Cys Gly Cys Leu
            100

<210> SEQ ID NO 84
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Lysine or Arginine

<400> SEQUENCE: 84

Arg Xaa Xaa Xaa
1

<210> SEQ ID NO 85
<211> LENGTH: 12
<212> TYPE: PRT
<213> ORGANISM: Homo sapiens

<400> SEQUENCE: 85

Glu Val His Leu Arg Ser Ile Arg Ser Thr Gly Gly
1               5                   10

<210> SEQ ID NO 86
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be Serine or Threonine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 86

Asn Xaa Xaa Xaa
```

```
<210> SEQ ID NO 87
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 87

Arg Xaa Xaa Arg
1
```

US 7,459,527 B2

BMP-7 VARIANTS WITH IMPROVED PROPERTIES

This application claims benefit under 35 U.S.C. § 119(e) to U.S. Ser. No. 60/558,189 filed on Mar. 31, 2004, entitled "Cysteine Knot Cytokine Variants with Improved Properties"; U.S. Ser. No. 60/570,520 filed on May 11, 2004 entitled "Cysteine Knot Cytokine Variants with Improved Properties"; U.S. Ser. No. 60/578,432 filed on Jun. 9, 2004 entitled "Cysteine Knot Cytokine Variants with Improved Properties"; and U.S. Ser. No. 60/587,464, filed on Jul. 13, 2004 entitled "Cysteine Knot Cytokine Variants with Improved Properties", all of which are expressly incorporated by reference in their entirety.

FIELD OF THE INVENTION

The invention relates to variants of bone morphogenetic proteins and other cysteine knot growth factors with improved properties, and to methods of making and using compositions utilizing these variants.

BACKGROUND OF THE INVENTION

Bone morphogenetic proteins (BMPs) are a well-known family of growth factors that contribute to developmental processes such as pattern formation and tissue specification as well as promoting wound healing and repair processes in adult tissues. BMPs were initially isolated by their ability to induce bone and cartilage formation and are now known to regulate cell proliferation, migration, differentiation, and apoptosis in a number of tissues and organs.

BMPs include a number of related human proteins, such as BMP-2, BMP-3 (osteogenin), BMP-3b (GDF-10), BMP-4 (BMP-2b), BMP-5, BMP-6, BMP-7 (osteogenic protein-1 or OP-1), BMP-8 (OP-2), BMP-8B (OP-3), BMP-9 (GDF-2), BMP-10, BMP-11 (GDF-11, BMP-12 (GDF-7), BMP-13 (GDF-6, CDMP-2), BMP-15 (GDF-9), BMP-16, GDF-1, GDF-3, GDF-5 (CDMP-1), and GDF-8 (myostatin). BMPs may be grouped into subfamilies. For example, BMP-2 and BMP-4 are closely related, as are BMP-5, BMP-6, BMP-7, BMP-8, and BMP-8B. BMP-13, BMP-14, and BMP-12 also constitute a subfamily. BMPs are also present in other animal species. Furthermore, there is some allelic variation in BMP sequences among different members of the human population.

BMPs are a subset of the transforming growth factor-β (TGF-β) family, which also includes TGFs (TGF-β1, TGF-β2, and TGF-β3), activins (activin A) and inhibins, macrophage inhibitory cytokine-1 (MIC-1), Mullerian inhibiting substance, anti-Mullerian hormone, and glial cell line derived neurotrophic factor (GDNF). The TGF-β family is in turn a subset of the cysteine knot cytokine superfamily. Additional members of the cysteine knot cytokine superfamily include, but are not limited to, platelet derived growth factor (PDGF), vascular endothelial growth factor (VEGF), placenta growth factor (PlGF), noggin, neurotrophins (BDNF, NT3, NT4, and βNGF), gonadotropin, follitropin, lutropin, interleukin-17, and coagulogen.

BMPs have demonstrated utility in the treatment of a variety of conditions and diseases. BMP-2 and BMP-7 have been used to promote bone formation, bone fracture healing, and spinal fusion. BMP-4 (Rundle et. al., (2003) Bone 32: 591-601), BMP-5 (Arosarena and Collins (2003) Arch. Otolaryngol. Head Neck Surg. 129: 1125-1130), BMP-6 (Helm (2003) Gene Ther. 10: 1735-1743), and BMP-9 (Li et. al., (2003) J. Gene Med. 5: 748-756), have also been demonstrated to promote bone healing in animal models. Animal studies indicate that BMP-7 may be used to treat renal fibrosis and renal failure (Wang et. al., (2001) J. Am. Soc. Nephrol. 12: 2392-2399; Wang and Hirshberg (2003) Am. J. Physiol. Renal Physiol. 284: 1006-1013; Zeisberg et. al., (2003) Nat. Med. 9: 964-968; and Zeisberg et. al., (2003) Am. J. Physiol. Renal Physiol. 285: F1060-F1067), ischemic stroke (Chang et. al., (2003) Stroke 34: 558-564 and Harvey et. al., Pharmacol. Ther. (2005) 105: 113-125) and inflammatory bowel diseases (Maric et. al., (2003) J. Cell Physiol. 196: 258-264).

Structurally, BMPs are dimeric cysteine knot proteins. Each BMP monomer comprises multiple intramolecular disulfide bonds. An additional intermolecular disulfide bond mediates dimerization in most BMPs. BMPs may form homodimers; furthermore some BMPs may form heterodimers. BMPs are expressed as pro-proteins comprising a long pro-domain, one or more cleavage sites, and a mature domain. The pro-domain is believed to aid in the correct folding and processing of BMPs. Furthermore, in some but not all BMPs, the pro-domain may noncovalently bind the mature domain and may act as an inhibitor (e.g., Thies et. al., (2001) Growth Factors 18: 251-259).

BMP signal transduction is initiated when a BMP dimer binds two type I and two type II serine/threonine kinase receptors. Type I receptors include but are not limited to ALK-1, ALK-2 (also called ActRIa or ActRI), ALK-3 (also called BMPRIa), and ALK-6 (also called BMPRIb) and type II receptors include but are not limited to ActRIIa (also called ActRII), ActRIIb, and BMPRII. Following BMP binding, the type II receptors phosphorylate the type I receptors, the type I receptors phosphorylate members of the Smad family of transcription factors, and the Smads translocate to the nucleus and activate the expression of a number of genes.

BMPs also interact with inhibitors, soluble receptors, and decoy receptors, including BAMBI (BMP and activin membrane bound inhibitor), BMPER (BMP-binding endothelial cell precursor-derived regulator), Cerberus, cordin, cordin-like, Dan, Dante, follistatin, follistatin-related protein (FSRP), ectodin, gremlin, noggin, protein related to Dan and cerberus (PRDC), sclerostin, sclerostin-like, and uterine sensitization-associated gene-1 (USAG-1). Furthermore, BMPs may interact with co-receptors, for example BMP-2 and BMP-4 bind the co-receptor DRAGON (Samad et. al., (2005) J. Biol. Chem.), and extracellular matrix components such as heparin sulfate and heparin (Irie et. al., (2003) Biochem. Biophys. Res. Commun. 308: 858-865)

For further background on the BMP family, see Balemans and Hul (2002) Dev. Biol. 250: 231-250; Bubnoff and Cho (2001) Dev. Biol. 239: 1-14; Celeste et. al., (1990) Proc. Nat. Acad. Sci. USA 87: 9843-9847; and Cheng et. al., (2003) J. Bone Joint Surgery 85A: 1544-1552

A number of unfavorable properties of naturally occurring BMPs limit the development and use of BMP therapeutics. BMP expression yields are typically poor and suitable expression hosts are limited, hindering development and production. BMPs often possess multiple biological effects, including unwanted side effects. Many BMPs are poorly soluble, reducing storage stability and bioavailability. Finally, BMPs may induce unwanted immune responses.

Earlier studies have identified BMP variants with a number of interesting properties. BMP variants with improved yield in the context of *E. coli* expression and subsequent refolding from inclusion bodies have been disclosed (U.S. Pat. No. 5,399,677; U.S. Pat. No. 5,804,416; and U.S. Pat. No. 6,677,432). Consensus BMP variants with BMP-like activity have also been described (U.S. Pat. No. 5,011,691; U.S. Pat. No. 6,395,883; U.S. Pat. No. 6,531,445). A BMP-2 point mutant, L51 P, has been described that does not bind type I receptors but binds type II receptors normally (Keller et. al., (2004) Nat. Struct. Mol. Biol. 11: 481-488). Deletion mutants of BMP-4 that act as competitive inhibitors of BMP signaling have been disclosed (Weber et. al., (2003) J. Bone Miner. Res. 18: 2142-2151). Mutagenesis experiments have also been performed on BMP-2 to identify residues important for receptor binding; some of these variants were found to act as antagonists (Kirsch et. al., (2000) EMBO J. 19: 3314-3324 and Nickel et. al., (2001) J. Bone Joint Surg. Am. 83-A: S7-S14). In addition, methods for identifying analogs of morphogenetic proteins have been claimed (U.S. Pat. No. 6,273,598). Furthermore, several point mutants of ActA with reduced ALK-4 binding have been identified: S60P, I63P, M91E, I105E, and M108A (Harrison et. al., (2004) J. Biol. Chem. 279: 28036-28044).

SUMMARY OF THE INVENTION

The present invention is related to variants of human bone morphogenetic proteins and other cysteine knot cytokine proteins with improved properties, including increased expression yield, expression in the absence of a pro-domain, increased solubility, increased specific activity, altered receptor, co-receptor, and inhibitor specificity, and decreased immunogenicity.

In one aspect, the invention provides variant BMP-7 protein comprising the sequence:
Fx(1-20)-Vb(21)-Fx(22-38)-Vb(39)-Fx(40-64)-Vb(65)-Fx(66-71)-Vb(72)-Fx(73-77)-Vb(78)-Fx(79-92)-Vb(93)-Fx(94-119)-Vb(120)-Fx(121-134)-Vb(135)

wherein
Fx1(1-20) corresponds to amino acid residues 1-20 of human BMP-7 (SEQ ID NO:5);
Vb(21) is selected from the group consisting of L and G;
Fx(22-38) corresponds to amino acid residues 22-38 of human BMP-7 (SEQ ID NO:5);
Vb(39) is selected from the group consisting of K, A and S;
Fx(40-64) corresponds to amino acid residues 40-64 of human BMP-7 (SEQ ID NO:5);
Vb(65) is selected from the group consisting of Y and N;
Fx(66-71) corresponds to amino acid residues 66-71 of human BMP-7 (SEQ ID NO:5);
Vb(72) is selected from the group consisting of A and D;
Fx(73-77) corresponds to amino acid residues 73-77 of human BMP-7 (SEQ ID NO:5);
Vb(78) is selected from the group consisting of Y and H;
Fx(79-92) corresponds to amino acid residues 79-92 of human BMP-7 (SEQ ID NO:5);
Vb(93) is selected from the group consisting of F, H, S and T;
Fx(94-119) corresponds to amino acid residues 94-119 of human BMP-7 (SEQ ID NO:5);
Vb(120) is selected from the group consisting of S and D;
Fx(121-134) corresponds to amino acid residues 121-134 of human BMP-7 (SEQ ID NO:5);
Vb(135) is selected from the group consisting of A and E;
wherein the variant comprises an amino acid substitution as compared to human BMP-7 (SEQ ID NO:5).

In a further aspect, the invention provides variant BMP-7 proteins comprising a substitution as compared to human BMP-7 (SEQ ID NO:5) selected from the group consisting of: L21G, K39A, K39S, Y65N, A72D, Y78H, F93H, F93S, F93T, S120D and A135E. In both cases, particular variants with single substitutions include, L21G, K39A, K39S, Y65N, A72D, Y78H, F93H, F93S, F93T, S120D and A135E. Particular sets of substitutions include, K39S-F93S; K39S-S120D; K39S-S120D-Y65N; K39S-S120D-A72D; K39S-S120D-Y78H; K39S-S120D-F93H; K39S-S120D-F93S; Y65N-L21G; Y65N-L21R; Y65N-K39S; Y65N-Y78H; Y65N-S120D; Y78H-A72D; Y78H-F93H-Y65N; Y78H-F93H-A72D; Y78H-F93H-S120D; Y78H-S120D and F93H-K39S.

In an additional aspect, the invention provides variant BMP-7 proteins having altered receptor binding affinity compared to wild-type BMP-7 (SEQ ID NO:5), the variant BMP-7 protein comprising one or more substitutions selected from the group consisting of: M23N, Q53G, Q53H and I86D.

BRIEF DESCRIPTION OF THE DRAWINGS

FIG. 1 shows sequence alignments of the mature domains of human BMP and GDF proteins (Residues 14-114 of SEQ ID NO:1, residues 16-116 of SEQ ID NO:2, residues 37-138 of SEQ ID NO:3, residues 38-139 of SEQ ID NO:4, residues 38-139 of SEQ ID NO:5, residues 38-139 of SEQ ID NO:6 and SEQ ID NOS:71-83). The consensus BMP sequence and the MIC-1 sequence are shown for reference. The N-terminal most residues of the mature domain, which are significantly less well aligned, are not shown.

FIG. 3 shows alignments of human type I BMP receptors and human type II BMP receptors used for homology modeling (SEQ ID NOS:7-12).

FIG. 4 shows 12-point binding curves for wild-type BMP-7 (Image clone) binding to ActRIIa, BMPRII, BMPRIa, and BMPRIb.

DETAILED DESCRIPTION OF THE INVENTION

Figure 2:
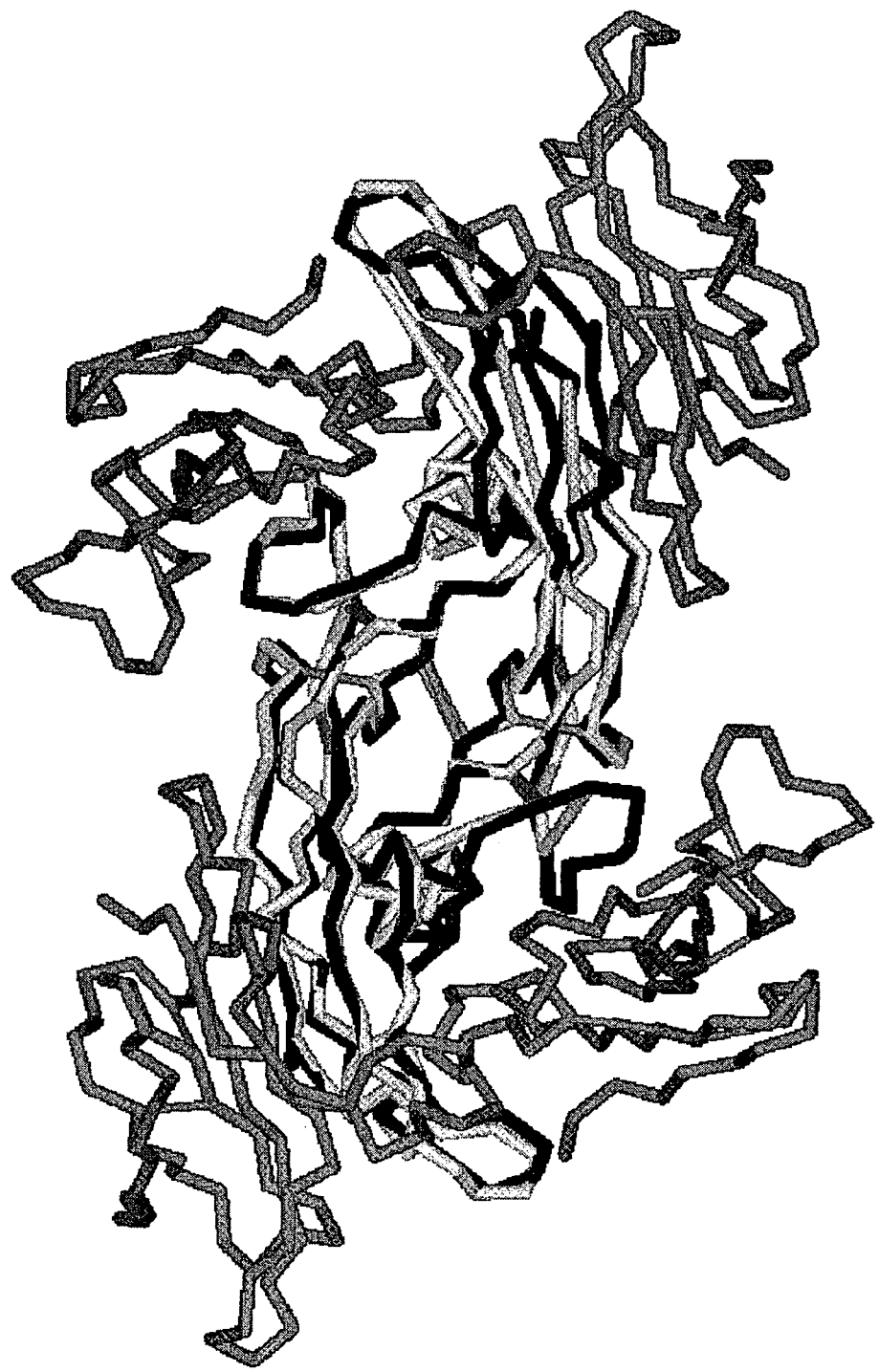
FIG. 2 shows the hexameric structure comprising BMP-7 dimer bound to two type I receptors and two type II receptors. The structure was generated by superimposing BMP-2 (white) bound to ALK-3 (gray, upper right and lower left) and BMP-7 (black) bound to ActRIIa (gray, upper left and lower right).

By "BMP responsive disorders" and grammatical equivalents herein is meant diseases, disorders, and conditions that may benefit from treatment with one or more BMPs. Examples of BMP responsive disorders include, but are not limited to, cartilage, bone, and tooth disorders or conditions including but not limited to bone fractures, bone degeneration, osteoporosis, spinal fusion, spinal degenerative disc disease, osteotomy, orthopedic and reconstructive surgery, and periodontal disease; repair of tendons and ligaments; renal disease including but not limited to chronic or acute renal failure, renal injury due to reperfusion, drug-induced renal toxicity, renal fibrosis, renal osteodystrophy, and vascular complications resulting from kidney disease; liver disease including but not limited to cirrhosis and hepatic fibrosis; lung disease including but not limited to asthma, emphysema, and pulmonary fibrosis; wound healing; cancers including but not limited to prostate cancer; inflammatory bowel disease; conditions that would benefit from a neuroprotective agent including but not limited to stroke, Parkinson's disease, traumatic brain injury, and amyotrophic lateral sclerosis; and skin and hair disorders. By "exposed residues" and grammatical equivalents herein are meant those residues whose side chains have at least 50 Å$^2$ (square Angstroms) of solvent accessible surface area in the context of a specified protein structure, preferably an x-ray crystal structure. As will be appreciated by those skilled in the art, other values such as 75 Å (square Angstroms) or fractional values such as 50% could be used instead. Furthermore, alternative methods such as contact models, among others, may be used to identify exposed residues. By "expression yield" and grammatical equivalents herein is meant the amount of protein, preferably in mg/L or PCD (picograms per cell per day) that is produced or secreted under a given expression protocol (that is, a specific expression host, transfection method, media, time, etc.). By "improved expression yield" and grammatical equivalents herein is meant an increase in expression yield, relative to a wild type or parent protein, under a given set of expression conditions. In a preferred embodiment, at least a 50% improvement is achieved, with improvements of at least 100%, 5-fold, 10-fold, or more being especially preferred. In another preferred embodiment, the expression yield is improved to yields of at least 1 μg/ml, with at least 10 μg/ml or 100 μg/ml being especially preferred. By "hydrophobic residues" and grammatical equivalents are meant valine, isoleucine, leucine, methionine, phenylalanine, tyrosine, and tryptophan. By "interface residues" and grammatical equivalents herein are meant those residues located within 8 Å (Angstroms) of a protein-protein contact. Distances of less than 5 Å (Angstroms) are especially preferred. Distances may be measured in the context of any structure, with high-resolution crystal structures being especially preferred. By "library" as used herein is meant a collection of protein sequences that are likely to take on a particular fold or have particular protein properties. The library preferably comprises a set of sequences resulting from computation, which may include energy calculations or statistical or knowledge based approaches. Libraries that range in size from about 5 to about 10$^{13}$ sequences are preferred. Libraries are generally generated experimentally and analyzed for the presence of members possessing desired protein properties. By "mature domain" herein is meant, in the context of BMP-7, a domain substantially comprising residues 1-137 of BMP-7. In wild type BMP-7, the mature domain is cleaved from the pro-domain by furin or a furin-like proprotein convertase. By "modification" and grammatical equivalents is meant one or more insertions, deletions, or substitutions to a protein or nucleic acid sequence. By "naturally occurring" or "wild type" or "wt" and grammatical equivalents thereof herein is meant an amino acid sequence or a nucleotide sequence that is found in nature, including allelic variations. In a preferred embodiment, the wild type sequence is the most prevalent human sequence. However, the wild type BMP nucleic acids and proteins may be a less prevalent human allele or BMP nucleic acids and proteins from any number of organisms, including but not limited to rodents (rats, mice, hamsters, guinea pigs, etc.), primates, and farm animals (including sheep, goats, pigs, cows, horses, etc.). By "nucleic acid" and grammatical equivalents herein is meant DNA, RNA, or molecules which contain both deoxy- and ribonucleotides. Nucleic acids include genomic DNA, cDNA and oligonucleotides including sense and anti-sense nucleic acids. Nucleic acids may also contain modifications, such as modifications in the ribose-phosphate backbone that confer increased stability and half-life. By "polar residues" and grammatical equivalents herein are meant aspartic acid, asparagine, glutamic acid, glutamine, lysine, arginine, histidine, serine, and threonine. By "pro-domain" herein is meant, in the context of a BMP or other TGF-β family member, the N-terminal domain that is removed following cleavage by furin or a furin-like proprotein convertase. The presence of the pro-domain may promote proper folding and processing. By "protein" herein is meant a molecule comprising at least two covalently attached amino acids, which includes proteins, polypeptides, oligopeptides and peptides. The protein may be made up of naturally occurring amino acids and peptide bonds, or synthetic peptidomimetic structures such as peptoids (see Simon et al. (1992) Proc. Natl. Acad. Sci. USA 89: 9367-9371). For example, homo-phenylalanine, citrulline, and norleucine are considered amino acids for the purposes of the invention, and both D- and L-amino acids may be utilized. By "protein properties" herein are meant physical, chemical, and biological properties including but not limited to physical properties (including molecular weight, hydrodynamic properties such as radius of gyration, net charge, isoelectric point, and spectral properties such as extinction coefficient), structural properties (including secondary, tertiary, and quaternary structural elements) stability (including thermal stability, stability as a function of pH or solution conditions, storage stability, and resistance or susceptibility to ubiquitination, proteolytic degradation, or chemical modifications such as methionine oxidation, asparagine and glutamine deamidation, sidechain racemerization or epimerization, and hydrolysis of peptide bonds), solubility (including susceptibility to aggregation under various conditions, oligomerization state, and crystallizability), kinetic and dynamic properties (including flexibility, rigidity, folding rate, folding mechanism, allostery, and the ability to undergo conformational changes and correlated motions), binding affinity and specificity (to one or more molecules including proteins, nucleic acids, polysaccharides, lipids, and small molecules, and including affinities and association and dissociation rates), enzymatic activity (including substrate specificity; association, reaction, and dissociation rates; reaction mechanism; and pH profile), ammenability to synthetic modification (including PEGylation and attachment to other molecules or surfaces), expression properties (such as yield in one or more expression hosts, soluble versus inclusion body expression, subcellular localization, ability to be secreted, and ability to be displayed on the surface of a cell), processing and posttranslational modifications (including proteolytic processing, N- or C-linked glycosylation, lipidation, sulfation, and phosphorylation), pharmacokinetic and pharmacodynamic properties (including bioavailability following subcutaneous, intramuscular, oral, or pulmonary delivery; serum half-life, distribution, and mechanism and rate of elimination) and ability to induce altered phenotype or changed physiology (including immunogenicity, toxicity, ability to signal or inhibit signaling, ability to stimulate or inhibit cell proliferation, differentiation, or migration, ability to induce apoptosis, and ability to treat disease). By "solubility" and grammatical equivalents herein is meant the maximum possible concentration of protein, in the desired or physiologically appropriate oligomerization state, in a solution of specified condition (i.e., pH, temperature, concentration of any buffer components, salts, detergents, osmolytes, etc.). Unless otherwise noted, dimeric BMPs are the desired species. By "soluble expression" and grammatical equivalents herein is meant that the protein is able to be produced at least partially in soluble form rather than in inclusion bodies when expressed in a prokaryotic host. It is preferred that at least 1 μg soluble protein is produced per 100 mL culture, with at least 10 μg or 100 μg being especially preferred. By "improved solubility" and grammatical equivalents herein is meant an increase in the maximum possible concentration of protein, in the desired or physiologically appropriate oligomerization state, in solution. For example, if the naturally occurring protein can be concentrated to 1 mM and the variant can be concentrated to 5 mM under the same solution conditions, the variant can be said to have improved solubility. In a preferred embodiment, solubility is increased by at least a factor of 2, with increases of at least 5-fold or 10-fold being especially preferred. As will be appreciated by those skilled in the art, solubility is a function of solution conditions. For the purposes of this invention, solubility should be assessed under solution conditions that are pharmaceutically acceptable. Specifically, pH should be between 6.0 and 8.0, salt concentration should be between 50 and 250 mM. Additional buffer components such as excipients may also be included; although it is preferred that albumin is not required. By "variant BMP nucleic acids" and grammatical equivalents herein is meant nucleic acids that encode variant BMPs. Due to the degeneracy of the genetic code, an extremely large number of nucleic acids may be made, all of which encode the variant BMPs of the present invention, by simply modifying the sequence of one or more codons in a way that does not change the amino acid sequence of the variant BMP. By "variant BMPs" or "non-naturally occurring BMPs" and grammatical equivalents thereof herein is meant non-naturally occurring BMPs which differ from a wild type or parent BMP by at least one (1) amino acid insertion, deletion, or substitution. It should be noted that unless otherwise stated, all positional numbering of variant BMPs and variant BMP nucleic acids is based on these sequences. BMP variants are characterized by the predetermined nature of the variation, a feature that sets them apart from naturally occurring allelic or interspecies variation of the BMP sequence. BMP variants must retain at least 50% of wild type BMP activity in one or more cell types, as determined using an appropriate assay described below. Variants that retain at least 75% or 90% of wild type activity are more preferred, and variants that are more active than wild type are especially preferred. Alternatively, in some embodiments BMP variants may be engineered to have different activities than a wild type BMP. For example, competitive inhibitors may be designed. A variant BMP may contain insertions, deletions, and/or substitutions at the N-terminus, C-terminus, or internally. In a preferred embodiment, variant BMPs have at least 1 residue that differs from the most similar human BMP sequence, with at least 2, 3, 4, or 5 different residues being more preferred. Variant BMPs may contain further modifications, for instance mutations that alter additional protein properties such as stability or immunogenicity or which enable or prevent posttranslational modifications such as PEGylation or glycosylation. Variant BMPs may be subjected to co- or post-translational modifications, including but not limited to synthetic derivatization of one or more side chains or termini, glycosylation, PEGylation, circular permutation, cyclization, fusion to proteins or protein domains, and addition of peptide tags or labels.

Naturally occurring BMPs regulate cell proliferation, migration, differentiation, and apoptosis in a number of tissues and organs; as a result BMPs may serve many therapeutic uses. However, naturally occurring BMPs are difficult to produce in large amounts, are sparingly soluble, exhibit pleiotropic activities, and may induce unwanted immune responses.

Here, are disclosed novel variants of human BMPs. These BMP variants comprise one or more modifications that were selected to improve biophysical properties and clinical performance.

Strategies for Improving Expression Yield

Reported expression yields for BMPs are typically very low. Reported yields range from 2-6 ng/mL for transiently transfected COS-1 cells in roller bottle culture to 100-200 ng/mL in DHFR-amplified stably transfected CHO cells, see U.S. Pat. No. 6,048,964 to John C. Lee, et al. To facilitate the development and therapeutic use of BMPs, it would be desirable to increase the expression yield to at least 10 μg/ml, with at least 100 μg/ml being more preferred and at least 1000 μg/ml being especially preferred.

A number of nucleic acid properties and protein properties may influence expression yields; furthermore the expression host and expression protocol contribute to yields. Any of these parameters may be optimized to improve expression yields. Also, expression yield may be improved by the incorporation of one or mutations that confer improved stability and/or solubility, as discussed further below. Furthermore, interactions between the pro-domain and the mature domain may influence folding efficiency, and so the pro-domain may also be targeted for modification.

In a preferred embodiment, nucleic acid properties are optimized to improve expression yields using one or more of the following strategies: 1) replace imperfect Kozak sequence, 2) reduce 5' GC content and secondary structure of the RNA, 3) optimize codon usage, 4) use an alternate leader sequence, 5) include a chimeric intron, or 6) add an optimized poly-A tail to the C-terminus of the message. In another preferred embodiment, protein properties are optimized to improve expression yields using one or more of the following strategies: 1) optimize the signal sequence, 2) optimize the proteolytic processing site, 3) replace one or more cysteine residues in order to minimize formation of improper disulfide bonds, 4) improve the rate or efficiency of protein folding, or 5) increase protein stability, especially proteolytic stability. In an alternate preferred embodiment, alternate pro-domain sequences are used. For example, the pro-domain from BMP-2 may be used to aid in the expression of BMP-4 (Wozney et. al., (1988) Science 242: 1528-1534). Pro-domains that may be used include but are not limited to the pro-domains from any BMP sequence and the MIC-1 pro-domain. The pro-domain may be expressed in cis or in trans.

In an additional preferred embodiment, transfection or expression conditions are optimized to increase expression yields. For example, since furin and other pro-protein convertase enzymes require calcium, the addition of calcium to the media during expression may increase the yield of properly processed protein. As another example, proteosome inhibitors may be added to minimize proteosomal degradation. Fetal calf serum or heparin may also be used. In a further preferred embodiment, the expression host is selected to optimize expression yields. Folding and processing of BMPs is relatively complex and may be assisted by appropriate chaperones. These chaperones may not be expressed equally in all mammalian cell lines. BMP-7 is naturally produced in the kidney and several well-established expression lines are derived from the kidney; in a preferred embodiment BMP-7 is expressed in a kidney cell line including but not limited to 293T, 239-EBNA, COS, and BHK. In another preferred embodiment, the cleavage site in BMP-7 is optimized to promote more efficient proteolytic processing by furin and related subtilisin-like proprotein convertase enzymes. Substrate preferences for furin have been well-characterized (Henrich et. al., (2003) Nat. Struct. Biol. 10: 520-526; Holyoak et. al., (2004) Biochem. 43: 2412-2421; and Duckert et. al., (2004) PEDS 17: 107-112), and cleavage sites in BMP and TGF-β proteins have been analyzed (Constam and Robertson (1999) JBC 144: 139-149). In an alternate preferred embodiment, BMP-7 is expressed in a cell line that is co-transfected with one or more chaperone or processing proteins, including but not limited to furin.

Strategies for Enabling the Use of Alternate Expression Hosts

BMPs are typically expressed in mammalian cells. In order to enable the use of alternate expression systems, including but not limited to yeast expression systems, it would be desirable to 1) eliminate the N-linked glycosylation site, 2) eliminate potential O-linked glycosylation sites, 3) enable expression in the absence of the pro-domain, and 4) enable processing by an alternate protease present in the desired expression host. In a preferred embodiment, one or more N- or O-linked glycosylation sites is removed. Removal of glycosylation sites from variant BMP polypeptides may be accomplished, for example, by the elimination of one or more serine or threonine residues to the native sequence or variant BMP polypeptide (for O-linked glycosylation sites) or by the modification of a canonical N-linked glycosylation site, N-X-Y-X, where X is any amino acid except for proline and Y is threonine, serine or cysteine. In another preferred embodiment, pro-domain dependence is reduced or eliminated by 1) introducing mutations that stabilize the folded state of the BMP; 2) reducing the exposed hydrophobic surface area of BMP; 3) stabilizing one or more intermediates along the folding pathway of BMP; or 4) replacing one or more pairs of cysteine residues forming a disulfide bond. In an additional preferred embodiment, the furin cleavage site is modified to allow recognition by an alternate protease that is present in the desired expression host. For example, the furin cleavage site may be changed to a kexin cleavage site to facilitate yeast expression. Kexin cleavage sites have been well characterized; see for example Holyoak et. al. (2004) Biochem. 43: 2412-2421.

In an alternate preferred embodiment, the BMPs are expressed using in vitro translation. A number of factors may be added to the reaction to improve the yield of total protein and of correctly folded protein, including but not limited to 1) pro-domains from any TGF-β family member, including but not limited to BMP-2, BMP-4, BMP-7, and MIC-1; 2) accessory factors and chaperones including but not limited to cysteine isomerases, proline isomerases, BiP, heat shock proteins, furin, and other proprotein convertases; 3) redox agents including but not limited to glutathione; 4) monovalent and divalent cations including but not limited to sodium, potassium, calcium, zinc, and magnesium; and 5) microsomes.

Strategies for Improving Solubility

A variety of strategies may be utilized to design BMP variants with improved solubility and expression yield. In a preferred embodiment, one or more of the following strategies are used: 1) reduce hydrophobicity by substituting one or more solvent-exposed hydrophobic residues with suitable polar residues, 2) increase polar character by substituting one or more neutral polar residues with charged polar residues, 3) increase protein stability, for example by one or more modifications that improve packing in the hydrophobic core, increase beta sheet forming propensity, improve helix capping and dipole interactions, or remove unfavorable electrostatic interactions (increasing the stability of a protein may improve solubility by decreasing the population of partially folded or misfolded states that are prone to aggregation), and 4) modify one or more residues that can affect the isoelectric point of the protein (that is, aspartic acid, glutamic acid, histidine, lysine, arginine, tyrosine, and cysteine residues). Protein solubility is typically at a minimum when the isoelectric point of the protein is equal to the pH of the surrounding solution. Modifications that perturb the isoelectric point of the protein away from the pH of a relevant environment, such as serum, may therefore serve to improve solubility. Furthermore, modifications that decrease the isoelectric point of a protein may improve injection site absorption (Holash et. al., (2002) Proc. Nat. Acad. Sci. USA 99: 11393-11398).

Strategies for Altering Receptor Binding Affinity or Specificity

Several strategies may be used to design BMP variants with improved receptor binding affinity or specificity. In a preferred embodiment, diversity is incorporated at one or more receptor interface positions. However, as is known in the art, modifications at positions distal to the receptor binding interface may also alter binding affinity or specificity. In an especially preferred embodiment, modifications are made to positions in BMP that contact one or more non-conserved receptor positions. For example, Arg 48, Gln 53, and Glu 60 in BMP-7 contacts position 76 in the type II receptor; this position is Glu in ActRIIb, Lys in ActRII, and Thr in BMPRII. Some BMPs, such as BMP-2, bind more tightly to type I receptors while other BMPs, such as BMP-7, have higher affinity for type II receptors. In an additional preferred embodiment, a BMP is modified such that its lower affinity receptor binding site is made more similar to a BMP for which that site is the higher affinity site. For example, the type I receptor interface of BMP-7 may be modified to be more similar to BMP-2, or the type II receptor interface of BMP-2 may be altered to be more BMP-7-like. In an alternate embodiment, modifications are made to stabilize the bound conformation of BMP versus the free conformation. For example, BMP-7 binds first to the type II receptor and then to the type I receptor, and binding to the type II receptor may increase binding affinity for the type I receptor. Binding to the type II receptor causes a conformational change in BMP, producing what may be a higher affinity state. Accordingly, mutations may be introduced to stabilize the bound state.

Strategies for Evading BMP Inhibitors

A number of soluble and membrane bound proteins function as endogenous inhibitors of BMP action. In a preferred embodiment, BMPs are engineered to reduce or eliminate binding affinity for one or more BMP inhibitors while retaining affinity for one or more of the BMP receptors. Rational alteration of inhibitor specificity may be used to control the site of BMP action, as many of the inhibitors are expressed in specific tissues or organs. Similar approaches may be used to alter specificity for co-receptors such as DRAGON, extracellular matrix components such as heparin and heparin sulfate, and serum components such as alpha2-macroglobulin.

Protein Design and Engineering Methods

A number of methods can be used to identify modifications (that is, insertion, deletion, or substitution mutations) that will yield BMP variants with improved properties. These methods include, but are not limited to, sequence profiling (Bowie and Eisenberg (1991) Science 253: 164-170), rotamer library selections (Dahiyat and Mayo (1996) Protein Sci 5: 895-903; Dahiyat and Mayo, Science (1997) 278: 82-87; Desjarlais and Handel (1995) Prot. Sci. (1995) 4: 2006-2018; Harbury et. al., (1995) Proc. Nat. Acad. Sci. USA 92: 8408-8412; Kono et al., Proteins (1994) 19: 244-255; Hellinga and Richards (1994) Proc. Nat. Acad. Sci. USA 91: 5803-5807); and residue pair potentials (Jones (1994) Prot. Sci. 3: 567-574).

In a preferred embodiment, one or more sequence alignments of BMPs and related proteins is analyzed to identify residues that are likely to be compatible with each position. In a preferred embodiment, the PFAM or BLAST alignment algorithm is used to generate alignments of the BMP subfamily, the TGF-β family, or the cysteine knot cytokine superfamily. For each variable position, suitable substitutions may be defined as those residues that are observed at the same position in homologous sequences. Especially preferred substitutions are those substitutions that are frequently observed in homologous sequences. In an additional preferred embodiment, an Analogous Contact Environment (ACE) algorithm, U.S. patent application Ser. No. 11/00/,647, filed Dec. 8. 2004, is used in conjunction with the sequence alignment information to identify alternate suitable residues that are located in structurally similar environments in other BMPs or homologs. In an especially preferred embodiment, rational design of improved BMP variants is achieved by using Protein Design Automation® (PDA®) technology; see U.S. Pat. Nos. 6,188,965; 6,269,312; 6,403,312; 6,708,120; WO98/47089 and U.S. Ser. Nos. 09/058,459, 09/127,926, 60/104,612, 60/158,700, 09/419,351, 60/181,630, 60/186,904, 09/419,351, 09/782,004 and 09/927,790, 60/347,772, and 10/218,102; and PCT/US01/218,102 and U.S. Ser. No. 10/218,102, U.S. Ser. No. 60/345,805; U.S. Ser. No. 60/373, 453 and U.S. Ser. No. 60/374,035, or using the sequence prediction algorithm (SPA) (Raha et al., (2000) Protein Sci., 9: 1106-1119; U.S. Ser. No. 09/877,695, filed Jun. 8, 2001 and U.S. Ser. No. 10/071,859, filed Feb. 6, 2002).

Structural Analysis of BMPs

Obtaining Structures of BMPs

PDA® technology calculations require a template protein structure. In one embodiment, the structure of a human BMP is obtained by x-ray crystallography or NMR. Structures of BMPs include BMP-2 (PDB code 3BMP, Scheufler et. al., (1999) J. Mol. Biol. 287: 103), BMP-2 mutant L51P (PDB code 1REU, Keller et. al., (2004) Nat. Struct. Mol. Biol. 11: 481) and wild type human BMP-7 (PDB code 1LXI Griffith et. al., (1996) Proc. Nat. Acad. Sci. USA 93: 878-883). It is also possible to use the crystal structure of another cysteine knot cytokine protein, such as TGF-β2 (PDB code 1TFG, Schlunegger and Grutter (1992) Nature 358: 430), or NMR structures of cysteine knot cytokine proteins such as TFG-β1 (PDB codes 1KLA, 1KLC, and 1KLD; Hinck et. al., (1996) Biochem. 35: 5817) In an especially preferred embodiment, the crystal structure is a co-crystal structure comprising a BMP and a BMP receptor. High-resolution structures are available for BMP-7 in complex with the receptor ActRIIa (PDB code 1LX5, Greenwald et. al., (2003) Mol. Cell 11: 605-617), activin A bound to ActRIIb (PDB codes 1NYS and 1NYU, Thompson et. al., (2003) EMBO J. 22: 1555-1566), and BMP-2 bound to ALK-3 (PDB code 1ES7, Kirsch et. al., (2000) Nat. Struct. Biol. 7: 492; and PDB code 1REW, Keller et. al. (2004) Nat. Struct. Mol. Biol. 11: 481). In another preferred embodiment, the crystal structure is a co-crystal structure comprising BMP and a BMP inhibitor. A high resolution structure is available for BMP-7 bound to the soluble inhibitor noggin (PDB code 1M4U, Groppe et. al. (2002) Nature 420: 636). Structures of additional BMPs alone and bound to one or more receptors or inhibitors may be built using NMR or x-ray crystal structures including but not limited to those described above in conjunction with homology modeling, structural alignment, and protein-protein docking methods known in the art.

Identifying Furin Cleavage Sites

The furin cleavage sites of BMPs may be determined by scanning for the consensus furin cleavage site, R-X-X-K/R (SEQ ID NO:84), in the residues located N-terminally relative to the aligned regions of the BMP mature domains. The sequence of BMP-7 in the region of the cleavage site is (from P8 to P1 before the cleavage site and from P1' to P4' after the cleavage site, with "|" indicating the cleaved bond) is EVHL-RSIR | STGG (SEQ ID NO:85), wherein the residues "STGG" comprise residues 1 through 4 of the BMP-7 mature domain (SEQ ID NO:5). The most favored furin cleavage site comprises R at P4, R at P1, and K or R at P2. It is also favorable to have at least one basic residue in residues P5-P8. Some BMPs have multiple cleavage sites. For example, BMP-4 has two cleavage sites, and sequential cleavage is thought to provide a mechanism for regulation of activation and signaling range (Degnin et. al., (2004) Mol. Biol. Cell 15: 5012-5020).

Identifying Glycosylation Sites

BMP-7 has an N-linked glycosylation site at Asn 80. When expressed in mammalian cells, the mature domain of BMP-7 does not include any O-linked glycosylation sites. However, it is possible that one or more serine or threonine residues would be susceptible to glycosylation in alternate expression hosts, including but not limited to yeast and Baculovirus expression systems. The presence and location of such O-linked glycosylation sites may be determined experimentally, for example using mass spectrometry.

Identifying Solvent-Exposed Hydrophobic Residues

As used herein, exposed hydrophobic residues in BMP-7 include but are not limited to Tyr 44, Trp 52, Trp 55, Ile 57, Phe 73, Tyr 78, Ile 86, Leu 90, Phe 93, Ile 94, Leu 115, Tyr 116, Tyr 117, Val 123, Leu 125, and Tyr 128. BMP-7 also contains three hydrophobic residues in the disordered N-terminal region (that is, residues 1-35). While these residues are not observed in the crystal structures of BMP-7, it is highly likely that they are significantly exposed to solvent. In a preferred embodiment, these additional hydrophobic residues, Leu 21, Met 23, and Val 26, are also considered solvent exposed hydrophobic residues.

Identifying Residues at the Receptor Binding Sites

In a preferred embodiment, residues that mediate intermolecular interactions between BMPs and their receptors are replaced with structurally and functionally compatible residues that confer improved receptor binding affinity or specificity. Preferred residues at the BMP/type I receptor interface include, but are not limited to, residues Lys 39, Phe 47, Asp 49, Leu 50, Gly 51, Pro 74, Leu 75, Asn 76, Ser 77, Tyr 78, Asn 80, Asn 83, Ile 86, Leu 90, Phe 93, Ile94, Pro 96, Tyr 116, Lys 126, Tyr 128, Arg 129, Asn 130, and Met 131. Preferred residues at the BMP/type II receptor interface include, but are not limited to, residues Tyr 44, Arg 48, Gln 53, Ile 57, Ala 58, Pro 59, Glu 60, Gly 61, Tyr 62, Ala 63, Gln 108, Asn 110, Ala 111, Ile 112, Ser 113, Val 114, Leu 115, Phe 117, Asn 122, Val 123, Leu 125, Lys 127, and Arg 134.

Identifying Residues at Inhibitor Binding Sites

In a preferred embodiment, residues that mediate intermolecular interactions between BMPs and their inhibitors are replaced with structurally and functionally compatible residues that confer reduced inhibitor binding affinity or increased inhibitor binding specificity. Preferred residues at the noggin/BMP-7 interface include, but are not limited to, Phe 73, Pro 74, Leu 75, Asn 76, Ser 77, Asn 83, Ile 86, Val 87, and Leu 90.

Identifying Residues in Regions of High Electrostatic Potential

Proteins may be destabilized by the presence of unfavorable electrostatic interactions or stabilized by the presence of favorable electrostatic interactions. Accordingly, a protein may be stabilized by removing unfavorable electrostatic interactions or by incorporating favorable electrostatic interactions. Modifying regions of high electrostatic potential may also modulate interactions with serum and extracellular matrix components, which may affect pharmacokinetics properties. In a preferred embodiment, the electrostatic potential that is present at each residue position is determined, for example by using Debye-Huckel calculations. Residues in BMP-7 that are located in regions of electrostatic potential greater than 0.25 or less than −0.25 include, but are not limited to, Lys 40, Ser 46, Arg 48, Tyr 62, Ala 64, Tyr 65, Tyr 66, Cys 67, Glu 68, Gly 69, Glu 70, Cys 71, Ala 72, Tyr 78, Asn 80, Ala 81, Thr 82, Asn 83, His 84, Ala 85, Val 87, Gln 88, Thr 89, Ile 94, Pro 100, Cys 104, Ala 105, Pro 106, Thr 107, Gln 108, Leu 109, Asn 110, Ala 111, Ile 112, Ser 113, Asn 122, Ile 124, Asn 130, Met 131, Val 132, Val 133, Arg 134, Ala 135, Cys 136, Gly 137, and His 139.

Design of Optimized BMP Variants

Identifying Suitable Modifications of the Furin Cleavage Site

The furin cleavage sequences of several BMPs differ somewhat from the consensus furin cleavage sequence. In BMP-7, preferred modifications to improve proteolytic processing include, but are not limited to, (P8) E→Q or K; (P6) H→K or R; (P5) L+K; and (P2) I→K or R.

Identifying Suitable Replacements for Glycosylation Sites

In a preferred embodiment, residues comprising a N- or O-linked glycosylation site are replaced with structurally and functionally compatible residues that do not comprise a glycosylation site. As is known in the art, N-linked glycosylation sites are specified by the sequence N-3 X-(S/T)-X (SEQ ID NO:86), where X may be any residue other than proline. Accordingly, an N-linked glycosylation site may be eliminated by 1) replacing the N with any other residue, 2) replacing either X with proline, or 3) replacing the S or T with any residue other than T, S, or C. Preferred modifications that remove the N-linked glycosylation site include, but are not limited to, replacing Asn 80 with Asp, Gln, Ser, or Thr; replacing Thr 82 with Val, and replacing Asn 83 with Pro.

Identifying Suitable Polar Residues for Each Exposed Hydrophobic Position

In a preferred embodiment, solvent exposed hydrophobic residues are replaced with structurally and functionally compatible polar residues. Alanine and glycine may also serve as suitable replacements, constituting a reduction in hydrophobicity. Furthermore, mutations that increase polar character, such as Phe to Tyr, and mutations that reduce hydrophobicity, such as Ile to Val, may be appropriate. In a preferred embodiment, preferred suitable polar residues are defined as those polar residues: 1) whose energy in the optimal rotameric configuration, as determined using PDA® technology, is more favorable than the energy of the exposed hydrophobic residue at that position and 2) whose energy in the optimal rotameric configuration is among the most favorable of the set of energies of all polar residues at that position. In a preferred embodiment, the polar residues that are included in the library at each variable position are deemed suitable by both PDA® technology calculations and by sequence alignment data. Alternatively, one or more of the polar residues that are included in the library are deemed suitable by either PDA® technology calculations or sequence alignment data.

Especially preferred modifications to BMP-7 include, but are not limited to, the following substitutions: L21D, L21G, L21K, L21N, L21R, L21S, M23D, M23G, M23K, M23N, M23R, M23S, V26D, V26E, V26G, V26K, V26N, V26S, Y44A, Y44D, Y44E, Y44G, Y44H, Y44K, Y44N, Y44P, Y44Q, Y44R, Y44S, W52A, W52E, W52K, W52Q, W55A, W55E, W55H, W55K, W55N, W55Q, I57A, I57D, I57E, I57H, I57K, I57L, I57T, I57V, E60R, F73A, F73D, F73E, F73H, F73Q, F73R, F73S, Y78D, Y78G, Y78H, Y78N, Y78R, Y78S, Y78T, I86A, I86D, I86E, I86K, I86Q, I86T, L90E, L90K, L90N, L90Q, L90R, L90S, L90T, F93A, F93D, F93E, F93G, F93H, F93Q, F93R, F93S, F93T, I94A, I94E, I94H, I94K, I94Q, I94R, I94T, L115E, L115K, L115T, Y116A, Y116D, Y116E, Y116H, Y116K, Y116S, Y116T, F117A, F117D, F117E, F117H, F117K, F117Q, F117R, F117Y, V123A, V123D, V123N, V123R, V123T, L125A, L125E, L125K, L125Q, Y128D, Y128E, Y128H, Y128K, and Y128Q. Most especially preferred modifications are those modifications that confer improved properties, such as improved expression yield or activity. Most especially preferred modifications to exposed hydrophobic residues in BMP-7 include, but are not limited to, L21G, L21R, M23G, M23N, M23R, M23S, V26G, V26N, Y65N, Y78H, Y78R, I86A, F93D, F93E, F93G, F93H, F93S, F93T, I94R, Y116H, F117H, F117Y, and Y128D.

Identifying Suitable Residues for Each Interface Position

Suitable residues for interface residues as used herein are meant all amino acid residues that are compatible with the structure of a BMP and that retain appreciable binding affinity for at least one of the BMP receptors. Alternatively, competitive inhibitor variants may be generated by identifying alternate residues that are compatible with the structure of a BMP but that substantially eliminate binding affinity for at least one of the BMP receptors. Suitable residues may confer binding specificity by maintaining or increasing affinity for one or two receptors or inhibitors while substantially reducing binding affinity for the other receptors, inhibitors, or additional binding partners. In other cases, modifications are selected to confer other desired properties, for example improved expression yield, while maintaining binding affinities that are substantially similar to the wild type protein. Typically, the interface positions will be substantially exposed to solvent. In such cases, preferred substitutions include the polar residues, alanine, and glycine. However, for interface positions that are substantially buried in the dimer structure, hydrophobic replacements are preferred. Suitable polar residues may also include the subset of polar residues that are observed in analogous positions in homologous proteins, especially other BMPs. In an especially preferred embodiment, suitable polar residues include the subset of polar residues with low or favorable energies as determined using PDA® technology calculations or SPA calculations (described above).

Especially preferred modifications to polar BMP-7 interface residues include, but are not limited to, K39D, K39E, K39G, K39N, K39R, K39S, K39T, R48D, R48E, R48H, R48K, R48N, R48Q, Q53A, Q53D, Q53E, Q53G, Q53H, Q53K, Q53R, Q53S, Q53T, E60H, E60K, E60N, E60P, E60Q, E60R, E60S, E60T, N76A, N76D, N76S, N76T, S77A, S77D, S77E, S77H, S77K, S77N, S77P, S77Q, S77T, K126D, K126E, K126G, K126Q, K126R, K127A, K127D, K127E, K127H, K127N, K127P, K127Q, K127S, K127T, R129D, R129E, R129K, R129N, R129S, R134D, R134E, R134K, R134Q, and R134S. Most especially preferred modifications are those modifications that confer improved properties, such as improved expression yield, improved activity, or enhanced receptor binding specificity. Most especially preferred modifications to residues in regions of high electrostatic potential in BMP-7 include, but are not limited to, K39A, K39S, R48H, R48N, R48Q, Q53A, Q53K, Q53D, Q53G, Q53S, Q53T, E60R, K126R, K127E, R129D, R129N, R134E, and R134S. Additional especially preferred modifications are those modifications that reduce binding to either type I or type II receptors, thereby potentially acting as a competitive inhibitor of BMP. Additional especially preferred modifications to receptor interface residues in BMP-7 include, but are not limited to, Y44T, W52E, and I57Q.

Further preferred modifications are those modifications that alter binding affinity or specificity to a BMP inhibitor. Preferred modifications that reduce binding to noggin include, but are not limited to, W55I, W55L, W55K, W55R, I57M, I57Y, I57E, I57H, I57K, I57Q, I57R, A58I, A58L, A58M, A58Y, A58V, A58E, A58H, A58K, A58Q, A58R, P59Y, N76E, N76Q, N76R, S77E, S77Q, N83F, N83W, N83Y, N83H, N83K, N83R, I86L, I86M, I86F, I86Y, I86R, V87H, S113I, S113L, S113M, S113F, S113Y, S113E, S113H, S113K, S113Q, S113R, L115M, L115K, L115R, V123M, V123Y, V123H, K127I, K127V, K127H, Y128I, and Y128R. Preferred modifications that increase binding to noggin include, but are not limited to, R48M, P59M, E60I, E60L, E60M, E60V, P74M, N76I, N76V, N76A, S77T, D119I, D119L, K126W, and K127M.

Identifying Suitable Residues for Regions of High Electrostatic Potential

Regions of high electrostatic potential may be modified in order to increase protein stability or to alter receptor binding affinity and specificity. In a preferred embodiment, residues that are located in a region of high electrostatic potential are replaced by structurally and functionally compatible residues that are predicted to interact favorably with the local electrostatic field. In a preferred embodiment, suitable polar residues include the subset of electrostatically favorable residues that are observed in analogous positions in homologous proteins, especially other BMPs. In an especially preferred embodiment, suitable polar residues include the subset of polar residues with low or favorable energies as determined using PDA® technology calculations or SPA calculations (described above).

Especially preferred modifications to BMP-7 residues located in regions of high electrostatic potential include, but are not limited to, Q88E, N110D, N110E, N110H, A111D, A111S, N130D, A135D, A135E, and A135S. Most especially preferred modifications are those modifications that confer improved properties, such as improved expression yield, improved activity, or enhanced receptor binding specificity. Most especially preferred modifications to receptor interface residues in BMP-7 include, but are not limited to, N110D, A135E, and A135S.

Identifying Suitable Residues for Additional Surface Positions

Additional residues on the surface of a BMP may be modified in order to improve stability, solubility, or expression yield. In a preferred embodiment, suitable polar residues include the subset of polar residues that are observed in analogous positions in homologous proteins, especially other BMPs. In an especially preferred embodiment, suitable polar residues include the subset of polar residues with low or favorable energies as determined using PDA® technology calculations or SPA calculations (described above).

Additional especially preferred modifications to BMP-7 surface residues include but are not limited to Q36E, Q36N, Q36R, E42D, E42Q, E42R, E42T, D49E, D49S, D54K, D54N, D54R, D54S, E70A, E70Q, N95D, N95K, N95Q, N95R, E97D, E97K, E97R, T98A, T98E, T98K, T98R, Q108D, Q108K, Q108S, D119E, D119N, D119S, D119T, S120D, S120E, S120N, S120R, S121D, S121E, S121K, S121N, S121T, N122E, N122Q, and N122R. Furthermore, residue T98 may be deleted. Most especially preferred modifications are those modifications that confer improved properties, such as improved expression yield, improved activity, or enhanced receptor binding specificity. Most especially preferred modifications to additional residues in BMP-7 include, but are not limited to, S120D.

Identifying Suitable Combinations of Mutations

In a preferred embodiment, variants comprising two or more mutations, including but not limited to those disclosed above, are made. Such variants may exhibit greater improvements in expression yield, solubility, or receptor specificity than point mutants. Such variants may also exhibit improvements in more than one protein property.

Especially preferred variants comprising two mutations include but are not limited to L21G/F93H, L21R/F93H, M23N/Y65N, M23R/Y65N, K39A/Y65N, K39A/F93H, K39S/Y78H, K39S/F93H, K39S/N110D, K39S/S120D, K39S/N130D, K39S/R134E, K39S/A135E, R48N/F93H, Q53D/Y65N, Q53G/Y65N, Q53G/Y78H, Q53S/Y65N, Q53T/Y65N, I57L/Y65N, Y65N/Y78H, Y65N/Y78R, Y65N/S120D, Y65N/A135E, Y65N/A135S, A72D/F93H, Y78H/F93H, Y78H/A105V, Y78H/Q108D, Y78H/Y116H, Y78H/F117Y, Y78H/S120D, Y78H/N130D, Y78H/R134E, Y78H/R134S, Y78H/A135E, Y78H/A135S, Y78H/H139R, Y78R/F93H, F93H/F117Y, F93H/S120D, F93H/R134S, and F93H/H139R. Especially preferred variants comprising three mutations include but are not limited to L21G/K39S/S120D, M23R/K39S/S120D, K39S/Y65N/S120D, K39S/A72D/S120D, K39S/Y78H/S120D, K39S/Q108D/S120D, Y65N/Y78H/F93H, Y65N/Y78H/R134E, A72D/Y78H/F93H, Y78H/F93H/Q108D, Y78H/F93H/F117H, Y78H/F93H/S120D, and Y78H/F93H/R134E, Especially preferred variants comprising four modifications include but are not limited to K39S/F93S/Q108D/S120D, K39S/F93S/S120D/R129D, K39S/Y65N/F93S/S120D, K39S/Y78H/F93S/S120D, K39S/F93S/S120D/R134E, K39S/A72D/F92S/S120D, Y65N/Y78H/F93S/R134E, A72D/Y78H/F93S/R134E, M23R/Y65N/F93S/R129D, Y65N/F93S/Q108D/R129D, K39S/F93T/Q108D/S120D, K39S/F93T/S120D/R129D, K39S/Y65N/F93T/S120D, K39S/Y78H/F93T/S120D, K39S/F93T/S120D/R134E, K39S/A72D/F93T/S120D, Y65N/Y78H/F93T/R134E, A72D/Y78H/F93T/R134E, M23R/Y65N/F93T/R129D, and Y65N/F93T/Q108D/R129D.

Additional Modifications

Additional modifications that might favorably impact expression yield and/or activity can be deduced by observing significant trends in the data obtained. Once such trend is the observation that introduction of a negatively charged amino (E or D) within the Finger 2 region of BMP7 (positions 105-139) leads in most cases to enhanced expression or activity, exemplified by the expression and activity of variants such as Q108D, N110D, N110E, S120D, K127E, Y128D, R129D, N130D, and A135E. Analysis of additional positions within this region indicates that BMP7 substitutions T107D, T107E, S113D, S113E will most likely also possess superior expression and/or activity. A second trend is that the substitution of exposed hydrophobic amino acids with more polar or less hydrophobic alternatives generally leads to enhanced expression yield or activity, exemplified by variants such as Y78H, I86A, Y128D, and multiple substitutions of F93. Application of this trend to I124, another exposed hydrophobic residue, suggests the additional expression- or activity-enhancing variants I124A, I124D, I124E, I124K, I124N, I124Q, I124R, I124S, I124T, and I124V.

Additional insertions, deletions, and substitutions may be incorporated into the variant BMPs of the invention in order to confer other desired properties. In a preferred embodiment, the BMP variant comprises insertions, deletions, or substitutions that reduce immunogenicity, as described in "Antibodies And Fc Fusion Proteins With Altered Immunogenicity," U.S. Ser. No. 60/643,313, filed Jan. 12, 2005. In an alternate preferred embodiment, the BMP variant is further modified to increase stability. As discussed above, modifications that improve stability can also improve solubility, for example by decreasing the concentration of partially unfolded, aggregation-prone species. For example, modifications can be introduced to the protein core that improve packing or remove polar or charged groups that are not forming favorable hydrogen bond or electrostatic interactions. It is also possible to introduce modifications that introduce stabilizing electrostatic interactions or remove destabilizing interactions. Additional stabilizing modifications also may be used. In another preferred embodiment, one or more cysteine, lysine, histidine, or other reactive amino acids are added to or eliminated from variant BMPs in order to incorporate or remove sites that are susceptible to covalent modification. For example, see "Rational Chemical Modification," U.S. patent application Ser. No. 10/956,352, filed Sep. 30, 2004. As is known in the art, variant BMPs may be modified by adding an epitope tag (e.g., a poly-histidine (poly-His), c-myc, or FLAG-tag) or a fusion partner (e.g., an immunoglobulin, the Fc region of an immunoglobulin, albumin, other BMPs, other cytokine proteins, the extracellular domain of a BMP receptor protein, etc.). For further details see the descriptions of tags and fusion partners in "Optimized Fc Variants," U.S. patent application Ser. No. 60/627,774, filed Nov. 12, 2004.

BMP Forms

BMPs are naturally expressed as pro-proteins comprising a long pro-domain, one or more cleavage sites, and a mature domain. This pro-protein is then processed by the cellular machinery to yield a dimeric mature BMP molecule. In a preferred embodiment, the variants of the invention are produced in a similar manner. The pro-domain is believed to aid in the correct folding and processing of BMPs. Furthermore, in some but not all BMPs, the pro-domain may noncovalently bind the mature domain and may act as a chaperone, as well as an inhibitor (e.g., Thies et. al., (2001) Growth Factors 18: 251-259). In additional preferred embodiments, the variants of the invention are produced and/or administered therapeutically in this form. In alternative embodiments, BMPs may be produced in other forms, including, but not limited to, mature domain produced directly or refolded from inclusion bodies, or full-length intact pro-protein. The variants of the invention are expected to find use in these and other forms.

Generating the Variants

Variant BMP nucleic acids and proteins of the invention may be produced using a number of methods known in the art, as elaborated upon below.

Preparing Nucleic Acids Encoding the BMP Variants

In a preferred embodiment, nucleic acids encoding BMP variants are prepared by total gene synthesis, or by site-directed mutagenesis of a nucleic acid encoding wild type or variant BMP. Methods including template-directed ligation, recursive PCR, cassette mutagenesis, site-directed mutagenesis or other techniques that are well known in the art may be utilized (see for example Strizhov et. al., PNAS 93:15012-15017 (1996), Prodromou and Perl, Prot. Eng. 5: 827-829 (1992), Jayaraman and Puccini, Biotechniques 12: 392-398 (1992), and Chalmers et. at. Biotechniques 30: 249-252 (2001)).

Expression Vectors

In a preferred embodiment, an expression vector that comprises the components described below and a gene encoding a variant BMP is prepared. Numerous types of appropriate expression vectors and suitable regulatory sequences for a variety of host cells are known in the art. The expression vectors may contain transcriptional and translational regulatory sequences including but not limited to promoter sequences, ribosomal binding sites, transcriptional start and stop sequences, translational start and stop sequences, transcription terminator signals, polyadenylation signals, and enhancer or activator sequences. In a preferred embodiment, the regulatory sequences include a promoter and transcriptional start and stop sequences. In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences, which flank the expression construct. The integrating vector may be directed to a specific locus in the host cell by selecting the appropriate homologous sequence for inclusion in the vector. Constructs for integrating vectors are well known in the art. In addition, in a preferred embodiment, the expression vector contains a selectable marker gene to allow the selection of transformed host cells. Selection genes are well known in the art and will vary with the host cell used. The expression vectors may be either self-replicating extrachromosomal vectors or vectors which integrate into a host genome.

The expression vector may include a secretory leader sequence or signal peptide sequence that provides for secretion of the variant BMP from the host cell. Suitable secretory leader sequences that lead to the secretion of a protein are known in the art. The signal sequence typically encodes a signal peptide comprised of hydrophobic amino acids, which direct the secretion of the protein from the cell. The protein is either secreted into the growth media or, for prokaryotes, into the periplasmic space, located between the inner and outer membrane of the cell. For expression in bacteria, bacterial secretory leader sequences, operably linked to a variant BMP encoding nucleic acid, are usually preferred.

Transfection/Transformation

The variant BMP nucleic acids are introduced into the cells either alone or in combination with an expression vector in a manner suitable for subsequent expression of the nucleic acid. The method of introduction is largely dictated by the targeted cell type. Exemplary methods include $CaPO_4$ precipitation, liposome fusion (e.g., using the reagent Lipofectin® or FuGene), electroporation, viral infection (e.g., as outlined in PCT/US97101019,), dextran-mediated transfection, polybrene mediated transfection, protoplast fusion, direct microinjection, etc. The variant BMP nucleic acids may stably integrate into the genome of the host cell or may exist either transiently or stably in the cytoplasm.

Hosts for the Expression of BMP Variants

Appropriate host cells for the expression of BMP variants include yeast, bacteria, archaebacteria, fungi, and insect and animal cells, including mammalian cells. Of particular interest are fungi such as *Saccharomyces cerevisiae* and *Pichia pastoris* and mammalian cell lines including 293 (e.g., 293-T and 293-EBNA), BRK, CHO (e.g., CHOK1 and DG44), COS, Jurkat, NIH3T3, etc. (see the ATCC cell line catalog). BMP variants can also be produced in more complex organisms, including but not limited to plants (such as corn, tobacco, and algae) and animals (such as chickens, goats, cows); see for example Dove, Nature Biotechnol. 20: 777-779 (2002). In one embodiment, the cells may be additionally genetically engineered, that is, contain exogenous nucleic acid other than the expression vector comprising the variant BMP nucleic acid.

Expression Methods

The variant BMPs of the present invention are produced by culturing a host cell transformed with an expression vector containing nucleic acid encoding a variant BMP, under the appropriate conditions to induce or cause expression of the variant BMP. Either transient or stable transfection methods may be used. The conditions appropriate for variant BMP expression will vary with the choice of the expression vector and the host cell, and will be easily ascertained by one skilled in the art through routine experimentation.

Purification

In a preferred embodiment, the BMP variants are purified or isolated after expression. Standard purification methods include electrophoretic, molecular, immunological and chromatographic techniques, including ion exchange, hydrophobic, affinity, and reverse-phase HPLC chromatography, and chromatofocusing. For example, a BMP variant may be purified using a standard anti-recombinant protein antibody column. Ultrafiltration and diafiltration techniques, in conjunction with protein concentration, are also useful. For general guidance in suitable purification techniques, see Scopes, R., Protein Purification, Springer-Verlag, NY, 3d ed. (1994). The degree of purification necessary will vary depending on the desired use, and in some instances no purification will be necessary.

Posttranslational Modification and Derivatization

Once made, the variant BMP may be covalently modified. Covalent and non-covalent modifications of the protein are thus included within the scope of the present invention. Such modifications may be introduced into a variant BMP polypeptide by reacting targeted amino acid residues of the polypeptide with an organic derivatizing agent that is capable of reacting with selected side chains or terminal residues. Optimal sites for modification can be chosen using a variety of criteria, including but not limited to, visual inspection, structural analysis, sequence analysis and molecular simulation. Sites for modification may be located in the pro-domain or the mature domain.

In one embodiment, the variant BMP of the invention are labeled with at least one element, isotope or chemical compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Labels include but are not limited to biotin, tag (e.g., FLAG, Myc) and fluorescent labels (e.g., fluorescein). Derivatization with bifunctional agents is useful, for instance, for cross linking a variant BMP to a water-insoluble support matrix or surface for use in the method for purifying anti-variant BMP antibodies or screening assays, as is more fully described below. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains (T.E. Creighton, Proteins: Structure and Molecular Properties, W.H. Freeman & Co., San Francisco, pp. 79-86 (1983)), acetylation of the N-terminal amine, and amidation of any C-terminal carboxyl group. Such derivatization may improve the solubility, absorption, transport across the blood brain barrier, serum half-life, and the like. Modifications of variant BMP polypeptides may alternatively eliminate or attenuate any possible undesirable side effect of the protein. Moieties capable of mediating such effects are disclosed, for example, in Remington's Pharmaceutical Sciences, 16th ed., Mack Publishing Co., Easton, Pa. (1980).

Another type of covalent modification of variant BMP comprises linking the variant BMP polypeptide to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689;

4,301,144; 4,670,417; 4,791,192 or 4,179,337. A variety of coupling chemistries may be used to achieve PEG attachment, as is well known in the art. Examples, include but are not limited to, the technologies of Shearwater and Enzon, which allow modification at cysteine residues and primary amines, including but not limited to histidine groups, lysine groups and the N-terminus (see, Kinstler et al, Advanced Drug Deliveries Reviews, 54, 477-485 (2002) and M J Roberts et al, Advanced Drug Delivery Reviews, 54, 459-476 (2002)). Both labile and non-labile PEG linkages may be used. An additional form of covalent modification includes coupling of the variant BMP polypeptide with one or more molecules of a polymer comprised of a lipophililic and a hydrophilic moiety. Such composition may enhance resistance to hydrolytic or enzymatic degradation of the BMP. Polymers utilized may incorporate, for example, fatty acids for the lipophilic moiety and linear polyalkylene glycols for the hydrophilic moiety. The polymers may additionally incorporate acceptable sugar moieties as well as spacers used for BMP attachment. Polymer compositions and methods for covalent conjugation are described, for example, in U.S. Pat. Nos. 5,681,811; 5,359,030.

Another type of modification is chemical or enzymatic coupling of glycosides to the variant BMP. Such methods are described in the art, e.g., in WO 87/05330 published 11 Sep. 1987, and in Aplin and Wriston, CRC Crit. Rev. Biochem., pp. 259-306 (1981). Alternatively, removal of carbohydrate moieties present on the variant BMP polypeptide may be accomplished chemically or enzymatically. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Assaying the Expression Yield of the Variants

A primary object of the current invention is the identification of variant BMPs with increased expression yield. Accordingly, the yield, using one or more set of expression conditions, of the variant and wild type BMPs is determined. In one embodiment, expression yields are determined using ELISA. One limitation of this technique is that some variants may confer increased or decreased antibody binding affinity. Accordingly, in a preferred embodiment ELISAs are performed using at least two monoclonal antibodies that recognize distinct epitopes. It is also possible to derive ELISA correction factors for selected variants by purifying said variants and determining their concentration through orthogonal methods, such as UV absorption or BCA assay. Alternatively, the BMPs may be engineered to contain a tag, such as a FLAG tag or His tag, and anti-tag antibodies may be used in the ELISA. In another embodiment, expression yields are determined using Western blotting. As with ELISA, a limitation is that some mutations may confer increased or decreased antibody binding affinity.

Assaying the Solubility of the Variants

In a preferred embodiment, the variant BMPs are assayed for solubility using methods including but not limited to those described below. In all preferred embodiments, the variant and wild type proteins are compared directly in the same assay system and under the same conditions in order to evaluate the solubility of each variant. The solubility of the BMP variants may be determined under a number of solution conditions. A variety of excipients, including solubilizing and stabilizing agents, may be tested for their ability to promote the highest soluble BMP concentration. In addition, different salt concentrations and varying pH may be tested. In a preferred embodiment, solubility is assayed under pharmaceutically acceptable conditions.

Differential light scattering (DLS) may be used to determine oligomerization state. DLS determines diffusion coefficients based on signal correlation from fluctuation of laser light scattered from Brownian motion of particles in solution (Heimenz, Chapter 10 in Polymer Chemistry, Marcel Dekker, Inc., NY, 1984, pp. 659-701). Commercially available instruments provide graphical or table readouts of particle population(s) by size(s) after transforming the diffusion coefficient(s) measured by deconvolution/autocorrelation of laser light scattering data using the Stokes-Einstein equation. The size is therefore the hydrodynamic radius. The distribution of particle sizes within a population(s) is the dispersity, and this factor provides data on the uniformity of the particle population(s). Both dispersity and the appearance of aggregates over time may be monitored to test for solubility. Aggregated protein may be easily resolved by DLS, and readily detected at low levels due to the physical property of aggregates: they scatter more laser light per unit due to the greater target surface area. The sample may be directly introduced into the cuvette (i.e., it is not necessary to perform a chromatographic step first). A relative ratio of monodisperse to aggregate particle population may be determined. Optionally, this ratio may be weighted by mass or by light scattering intensity. Thus, DLS is a preferred technique to monitor formation of aggregates, and holds the advantage in that it is a non-intrusive technique.

In another preferred embodiment analytical ultracentrifugation (AUC) is used to determine the oligomerization state of the variant BMPs. AUC can be performed in two different 'modes', either velocity or equilibrium. Equilibrium AUC is the most preferred method for determining protein molecular weight and oligomeric state measurement.

A further preferred embodiment is to use size-exclusion chromatography (SEC) to determine the oligomerization state of the BMP variants. Utilizing high performance liquid chromatography, sample may be introduced to an isocratic mobile phase and separated on a gel permeation matrix designed to exclude protein on the basis of size. Thus, the samples will be "sieved" such that the aggregated protein will elute first with the shortest retention time, and will be easily separated from the remainder. This can identify aggregates and allow a relative quantification by peak integration using the peak analysis software provided with the instrument.

In an alternate embodiment, protein concentration is monitored as a function of time. In the case of poor solubility, aggregates will form over time in the protein solution, and eventually precipitate entirely. This may be performed following centrifugation and sampling of the solution phase, in which case insolubility can be measured as a drop in solution protein concentration over time will be observed following centrifugation.

In an alternate embodiment, the oligomerization state is determined by monitoring relative mobility on native gel electrophoresis.

In another embodiment, the amount of protein that is expressed solubly is determined. While factors other than the solubility of the native protein can impact levels of soluble expression, improvements in soluble expression may correlate with improvements in solubility. Any of a number of methods may be used; for example, following expression, SDS-polyacrylamide gel electrophoresis and/or western blots can be done on the soluble fraction of crude cell lysates or the expression media.

Furthermore, any of a number of high throughput screens for soluble expression may be used. In one embodiment, the protein of interest is fused to a fluorescent protein such as GFP, and the cells monitored for fluorescence (Waldo et. al., Nat. Biotechnol. 17: 691 (1999)). In an alternate embodiment, the protein of interest is fused to the antibiotic resistance enzyme chloramphenicol transferase. If the protein expresses solubly, the enzyme will be functional, thereby allowing growth on media with increased concentration of the antibiotic chloramphenicol (Maxwell et. al., Protein Sci. 8: 1908 (1999)). In another embodiment, the protein of interest is expressed as a fusion with the alpha domain of the enzyme beta-galactosidase. If the protein expresses in soluble form, the alpha domain will complement the omega domain to yield a functional enzyme. This may be detected as blue rather than white colony formation when the cells are plated on media containing the indicator X-gal (Wigley et. al., Nat. Biotechnol. 19: 131 (2001)).

Assaying the Activity of the Variants

In a preferred embodiment, the activity of the wild-type and variant proteins are analyzed using in vitro receptor binding assays, cell-based activity assays, or in vivo activity assays.

Receptor Binding Assays

In a preferred embodiment, the affinity of the variant BMPs for one or more BMP receptors is determined. In an especially preferred embodiment, affinities for ALK-2, ALK-3, ALK-6, ActRII, ActRIIb, and BMPRII are determined. Suitable binding assays include, but are not limited to, ELISA, fluorescence anisotropy and intensity, scintillation proximity assays (SPA) Biacore (Pearce et al., Biochemistry 38: 81-89 (1999)), DELFIA assays, and AlphaScreen™ (commercially available from PerkinElmer; Bosse R., Illy C., and Chelsky D (2002)).

In a preferred embodiment, Biacore or surface plasmon resonance assays (see for example McDonnell (2001) Curr. Opin. Chem. Biol. 5: 572-577) are used to determine the affinity of one or more BMP variants for one or more BMP receptors. Biacore experiments may be performed, for example, by binding BMP receptor-Fc fusion proteins to a protein A derivitized chip or an NTA chip and testing each BMP variant as an analyte. It is also possible to bind an anti-BMP antibody to the chip, or to bind the BMP variant to the chip and test soluble receptor or Fc-receptor fusion proteins as analytes. Biacore experiments have been used previously to characterize binding of TGF-β isoforms to their receptors (De Crescenzo et. al., (2001) J. Biol. Chem. 276: 29632-29643, De Crescenzo et. al., (2003) J. Mol. Biol. 328: 1173-1183).

In an alternate preferred embodiment, a plate-based Direct Binding Assay is used to determine the affinity of one or more BMP variants for one or more BMP receptors. This method is a modified sandwich ELISA in which BMP is captured using an anti-BMP monoclonal antibody and then detected using a BMP receptor/Fc fusion protein.

In another preferred embodiment, AlphaScreen™ assays (Bosse R., Illy C., and Chelsky D (2002). Principles of AlphaScreen™ PerkinElmer Literaure Aplication Note Ref# s4069. http://lifesciences.perkinelmer.com/Notes/S4069-0802.pdf) are used to characterize receptor and inhibitor binding. AlphaScreen™ is a bead-based non-radioactive luminescent proximity assay where the donor beads are excited by a laser at 680 nm to release singlet oxygen. The singlet oxygen diffuses and reacts with the thioxene derivative on the surface of acceptor beads leading to fluorescence emission at ~600 nm. The fluorescence emission occurs only when the donor and acceptor beads are brought into close proximity by molecular interactions occurring when each is linked to ligand and receptor (or ligand and inhibitor) respectively. This interaction may be competed away by adding an appropriate amount of unlabeled BMP variant that binds the relevant receptor or inhibitor.

In one embodiment, AlphaScreen™ assays are performed using 1) BMP modified by the addition of a suitable tag or label; 2) donor beads capable of binding the tag or label used to modify the BMP; 3) a BMP receptor or inhibitor modified by the addition of a suitable tag or label; 4) acceptor beads capable of binding the tag or label used to modify the BMP receptor, and 5) varying amounts of an unlabeled variant BMP-7 molecule, which acts as a competitor. It is also possible to coat the donor or acceptor beads with antibodies that specifically recognize the native BMP or BMP receptor, or to bind the receptor to the donor beads and the ligand to the acceptor beads. In an alternate embodiment, AlphaScreen™ assays are performed using 1) a type I BMP receptor modified by the addition of a suitable tag or label; 2) donor beads capable of binding the tag or label used to modify the type I BMP receptor; 3) a type II BMP receptor modified by the addition of a suitable tag or label; 4) acceptor beads capable of binding the tag or label used to modify the type II BMP receptor; 5) BMP, and 6) varying amounts of an unlabeled variant BMP-7 molecule, which acts as a competitor. It is also possible to bind the type I BMP receptor to the acceptor beads and the type II BMP receptor to the donor beads.

In another embodiment, fluorescence assays are used. Either BMP-7 or a BMP-7 receptor or inhibitor may be labeled with a fluorescent dye (for examples of suitable dyes, see the Molecular Probes catalog). As is known in the art, the fluorescence intensity or anisotropy of a labeled molecule may change upon binding to another molecule. Fluorescence assays may be performed using 1) fluorescently labeled BMP-7, 2) a BMP receptor or inhibitor, and 3) varying amounts of an unlabeled variant BMP-7 protein, which acts as a competitor.

In an additional embodiment, scintillation proximity assays (SPA) are used to determine receptor binding affinity. For example, BMP receptor-Fc fusions may be bound to protein A coated SPA beads or flash-plate and treated with S35-labeled BMP; the binding event results in production of light.

Cell-Based Activity Assays

BMPs promote the growth and differentiation of a number of types of cells. BMP activity may be monitored, for example, by measuring BMP-induced differentiation of MC3T3-E1 (an osteoblast-like cell derived from murine calvaria), C3H10T½ (a mouse mesenchymal stem cell line derived from embryonic connective tissue), ATDC5 (a mouse embryonal carcinoma cell), L-6 (a rat myoblast cell line) or C2C12 (a mouse myoblastic cell line) cells. Differentiation may be monitored using, for example, luminescence reporters for alkaline phosphatase or colorimetric reagents such as Alcian Blue or PNPP (Asahina et. al., (1996) Exp. Cell Res. 222: 38-47; Inada et. al., (1996) Biochem. Biophys. Res. Commun. 222: 317-322; Jortikka et. al. (1998) Life Sci. 62: 2359-2368; Cheng et. al., (2003) J. Bone Joint Surgery 95A: 1544-1552). The rat limb bud cartilage differentiation assay may also be used to monitor activity in primary cells. In an alternate embodiment, reporter gene or kinase assays may be used. BMPs activate the JAK-STAT signal transduction pathway. Accordingly, a BMP responsive cell line containing a STAT-responsive reporter such as GFP or luciferase may be used (Kusanagi et. al., (2000) Mol. Biol. Cell. 11: 555-565).

In a preferred embodiment, BMP activity in kidney cells is determined using cell-based assays; see for example Wang and Hirschberg (2004) J. Biol. Chem. 279: 23200-23206.

Animal Models of BMP Activity

In the simplest embodiment, BMP activity in an animal is measured as bone induction following subcutaneous injection. In a preferred embodiment, the activity of one or more BMP variants is determined in an animal model of a BMP-responsive disease or condition. Animal models of renal disease include, but are not limited to, the rat nephrotoxic serum nephritis model (Zeisberg et. al., 2003)), the rat chronic cyclosporine A-induced nephropathy model (Li et. al. (2004) Am. J. Physiol. Renal Physiol. 286: F46-57), the mouse unilateral uretreral obstruction model (Schanstra et. al., (2003) Thromb. Haemost. 89: 735-740), streptozotocin-induced diabetic nephropathy (Taneda et. al., (2003). J. Am. Soc. Nephrol. 14: 968-980), the anti-thy 1.1 mAb and Habu snake venom induced glomerulonephritis models (Dimmler et. al., (2003) Diagn. Mol. Pathol. 12: 108-117), and the rat 5/6 remnant kidney model (Romero et. al., (1999) Kidney Int. 55: 945-955). Animal models of liver disease include, but are not limited to, rat bile duct ligation/scission model (Park et. al., (2000) Pharmacol. Toxicol. 87: 261-268), $CCl_4$ plus ethanol-induced liver damage (Hall et. al., (1991) Hepatology 12: 815-819), dimethylnitrosamine-induced liver cirrhosis (Kondou et. al., (2003) J. Hepatol. 39: 742-748), and thioacetamide-induced liver damage (Muller et. al., (1988) Exp. Pathol. 34: 229-236). Animal models of lung disease include, but are not limited to, ovalbumin-induced airway fibrosis (Kenyon et. al., (2003) Toxicol. Appl. Pharmacol. 186: 90-100), bleomycin-induced lung fibrosis (Izbicki et. al., (2002) Int. J. Exp. Pathol. 83: 111-119), monocrotaline-induced pulmonary fibrosis (Hayashi et. al., (1995) Toxicol. Pathol. 23: 63-71), and selective irradiation (Pauluhn et. al., (2001) Toxicology 161: 153-163). Animal models of neurological disease include, but are not limited to, animal models for Parkinson's disease such as the 6-hydroxydopamine (6-OHDA) hemilesioned rat model and MPTP-induced Parkinson's disease, animal models of ALS such as rats or mice expressing mutant SOD1 (Shibata et. al., (2002) Neuropathology 22: 337-349), and animal models of stroke induced by intracortical microinjection of endothelin or quinolinic acid (Gilmour et. al., (2004) Behav. Brain Res. 150: 171-183) or cerebral artery occlusion (Merchenthaler et. al., (2003) Ann. NY Acad. Sci. 1007: 89-100).

Administration and Treatment Using BMP Variants

Once made, the BMP variants of the invention may be administered to a patient to treat a BMP related disorder. The BMP variants may be administered in a variety of ways, including, but not limited to orally, parenterally, subcutaneously, intravenously, intranasally, transdermally, intraperitoneally, intramuscularly, intrapulmonarally, vaginally, rectally, intranasally or intraocularly. In some instances, the variant BMP may be directly applied as a solution or spray.

The pharmaceutical compositions of the present invention comprise a BMP variant in a form suitable for administration to a patient. In the preferred embodiment, the pharmaceutical compositions are in a sterile, water-soluble form and may include pharmaceutically acceptable acid addition salts or pharmaceutically acceptable base addition salts. The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives that are "generally recognized as safe" (GRAS) are well known in the art, and are used in a variety of formulations.

Any of a number of drug delivery devices or sustained release formulations may be used. For example, a variant BMP may be administered as a pro-protein comprising a BMP pro-domain and a BMP mature domain. BMPs may also be administered as BMP-impregnated matrix material (for example Geiger et. al., Adv. Drug Deliv. Rev. (2003) 55: 1613-1629; Hu et. al. J. Biomed. Mater. Res. (2003) 67A: 591-598; Peel et. al., J. Craniofac Surg. (2003) 14: 284-291); such a method of administration is especially preferred for promoting bone healing and growth. Furthermore, implants for bone repair may be coated with BMPs to promote bone healing and improve bone strength (Schmidmaier et. al., Bone (2002) 30: 816-822). In a further embodiment, the variant BMPs are added in a micellular formulation (U.S. Pat. No. 5,833,948), liposomes (Matsuo et. al., J. Biomed. Mater. Res. (2003) 66A: 747-754), biodegradable polymers (Saito and Takaoka, Biomaterials (2003) 24: 2287-2293; Saito et. al. Bone (2003) 32: 381-386; Weber et. al., Int. J. Oral Maxillofac. Surg. (2002) 31: 60-65; Saito et. al. J. Bone Joint Surg. Am. (2001) 83-A: S92-S98), hydrogels (Yamamoto et. al., Biomaterials (2003) 24: 4375-4383), or the like.

Combinations of pharmaceutical compositions may be administered. Moreover, the compositions may be administered in combination with other therapeutics.

Nucleic acid encoding the variant BMPs may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Any of a variety of techniques known in the art may be used to introduce nucleic acids to the relevant cells. The oligonucleotides may be modified to enhance their uptake, e.g., by substituting their negatively charged phosphodiester groups by uncharged groups. For review of gene marking and gene therapy protocols see Anderson et. al., Science 256:808-813 (1992).

EXAMPLES

Example 1

Structural Modeling

Hexameric complexes comprising a BMP-7 dimer or a BMP-2 dimer bound to two ALK-3 receptors and two ActRIIa receptors was constructed using the structure of BMP-7 bound to ActRIIa (PDB code 1LX5) and the structure of BMP-2 bound to ALK-3 (PDB code 1ES7). Using InsightII (Accelrys), the BMP structures were superimposed as follows: BMP-2 residues 22-32 superimposed with BMP-7 residues 47-56, BMP-2 residues 49-71 superimposed with BMP-7 residues 73-95, and BMP-2 residues 101-106 superimposed with BMP-7 residues 126-131. This yielded a backbone atom RMSB of 0.77 Å. The superposition was repeated so that chain A in the BMP-7 structure was superimposed onto chains A and C of the BMP-2 structure. The sequence alignment between BMP-2 and BMP-7 is shown in FIG. 3 and the structure of the hexameric complex is shown in FIG. 2.

Figure 5:
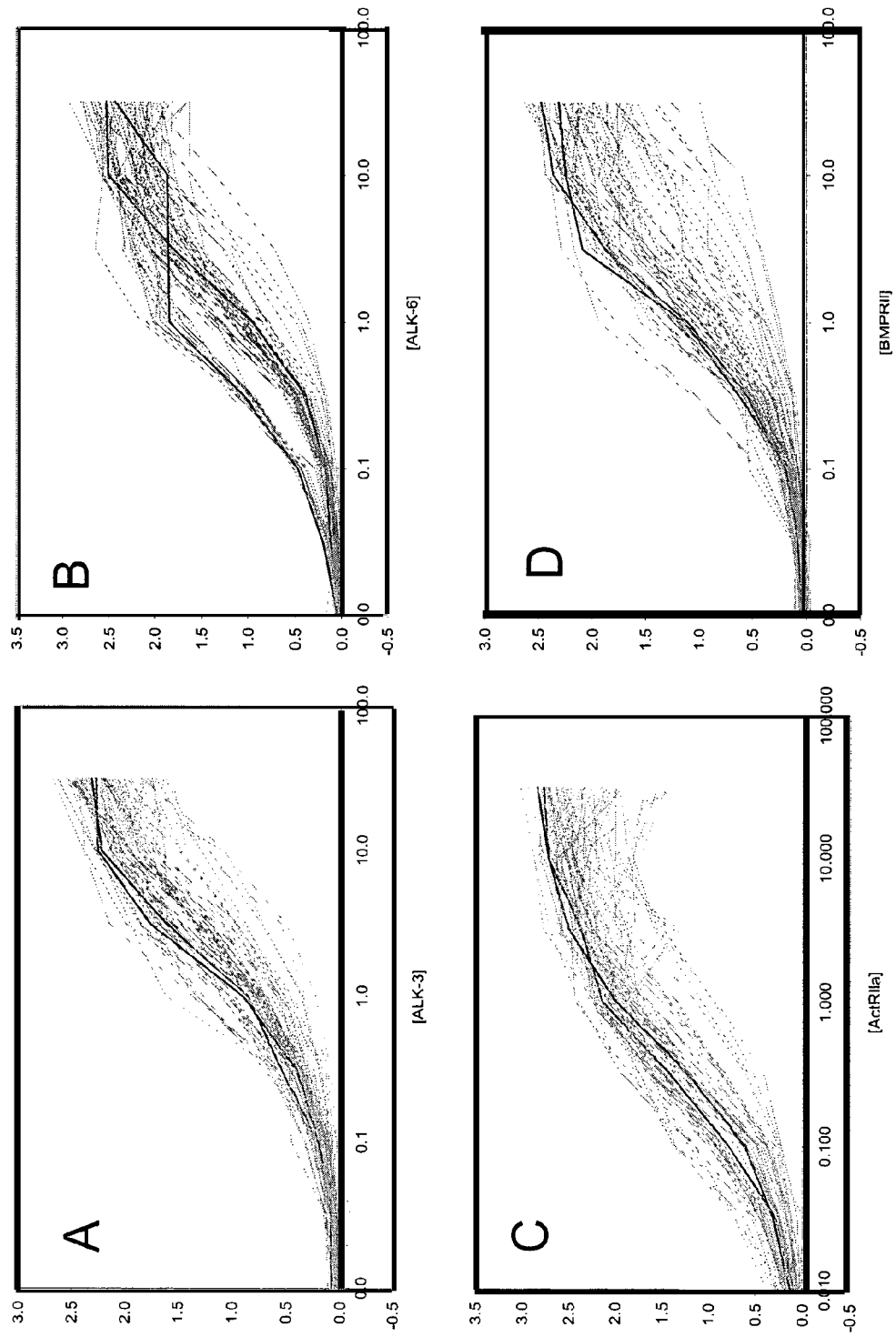
FIG. 5 shows 12-point binding curves for (A) BMPRIa (ALK-3), (B) BMPRIb (ALK-6), (C) ActRIIa, and (D) BMPRII. The thick black lines are wild type BMP-7 (Image clone). The thin gray lines correspond to variants.
Figure 6:
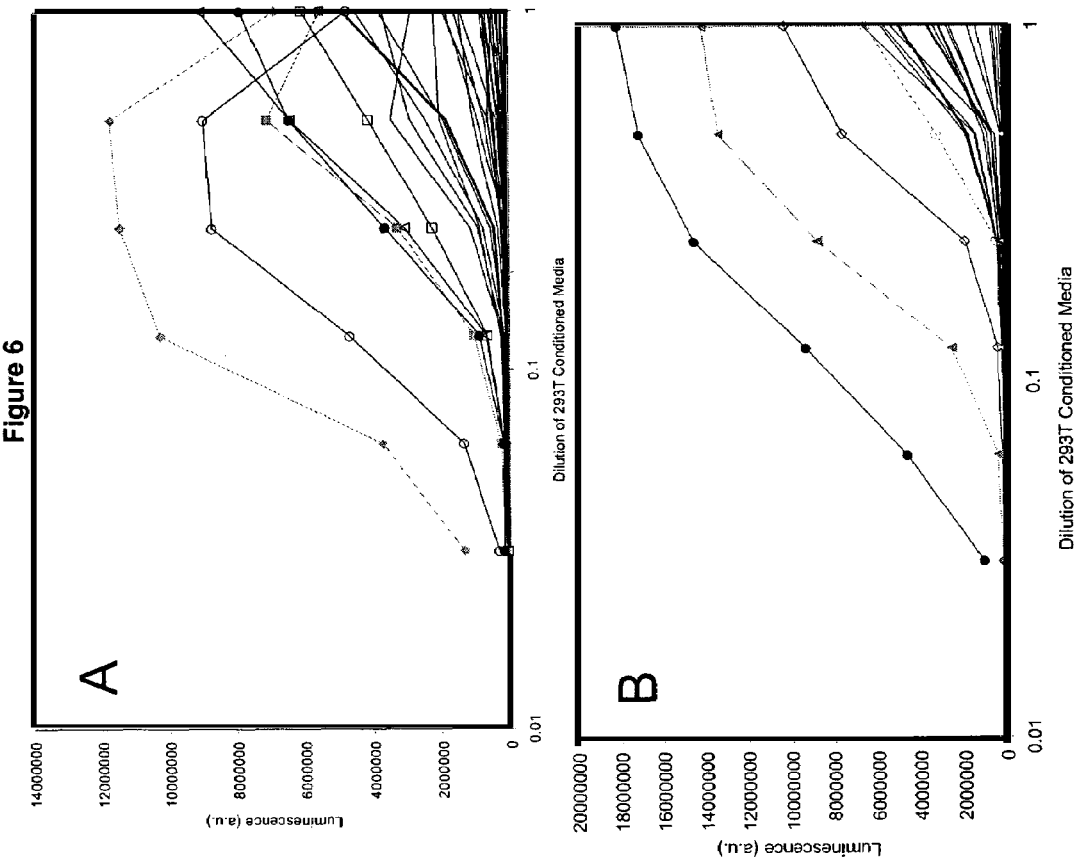
FIG. 6 shows dose-response C2C12 biassay data for selected Library 1 variants. Highlighted variants in (A) include: F93Q (black hollow circles), F93S (gray filled diamonds), N110D (gray filled squares), S120D (black hollow squares), A135E (black hollow triangles), A135S (black filled circles) and wild type (thick black line, no markers). Additional variants are shown in (A) and (B)
Figure 7:
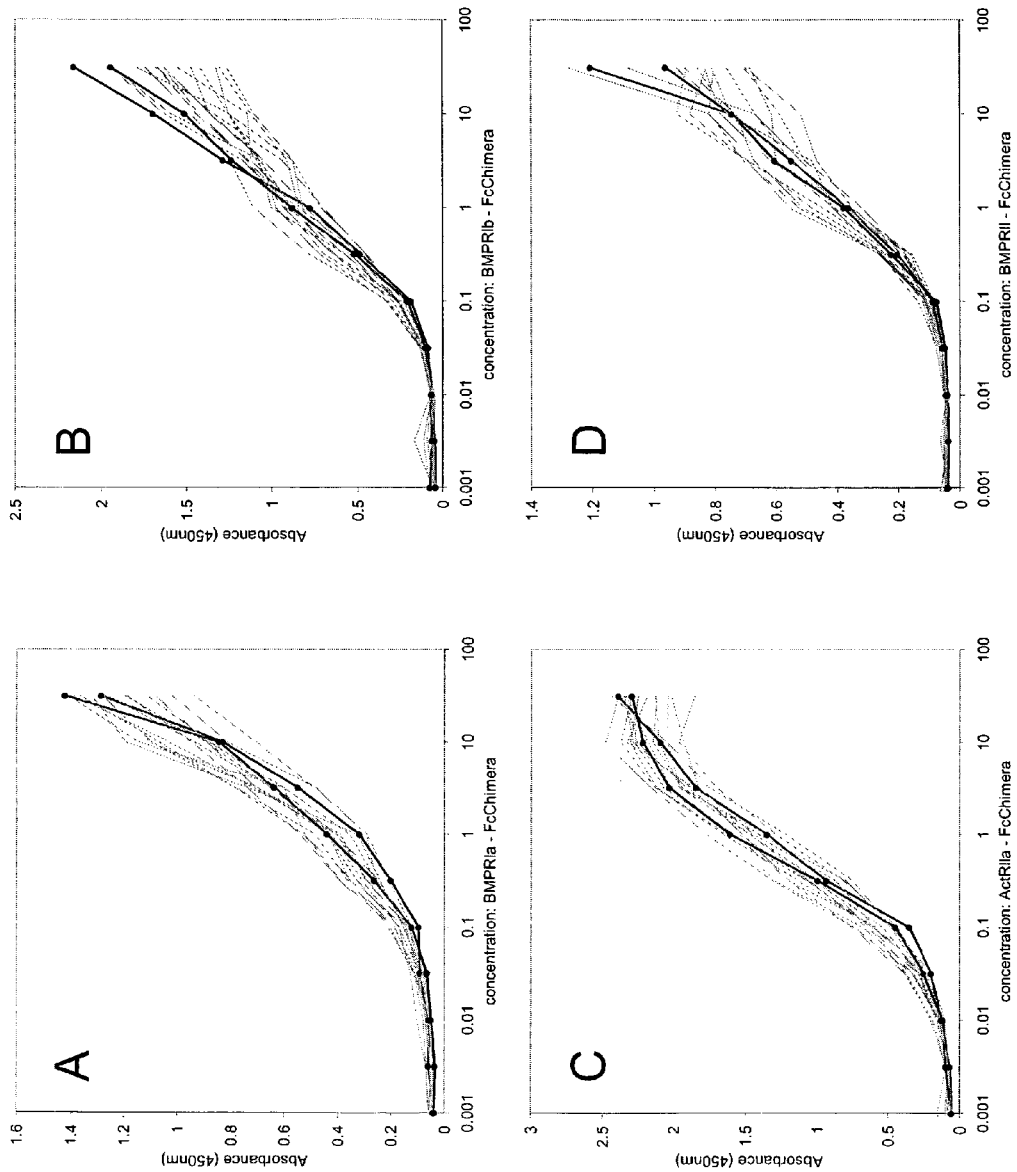
FIG. 7 shows 12-point binding curves for (A) BMPRIa (ALK-3), (B) BMPRIb (ALK-6), (C) ActRIIa, and (D) BMPRII. Two replicates of wild type (Image clone) are shown (thick black line, filled black circles). Variants are shown in thin gray lines, no markers.
Figure 8:
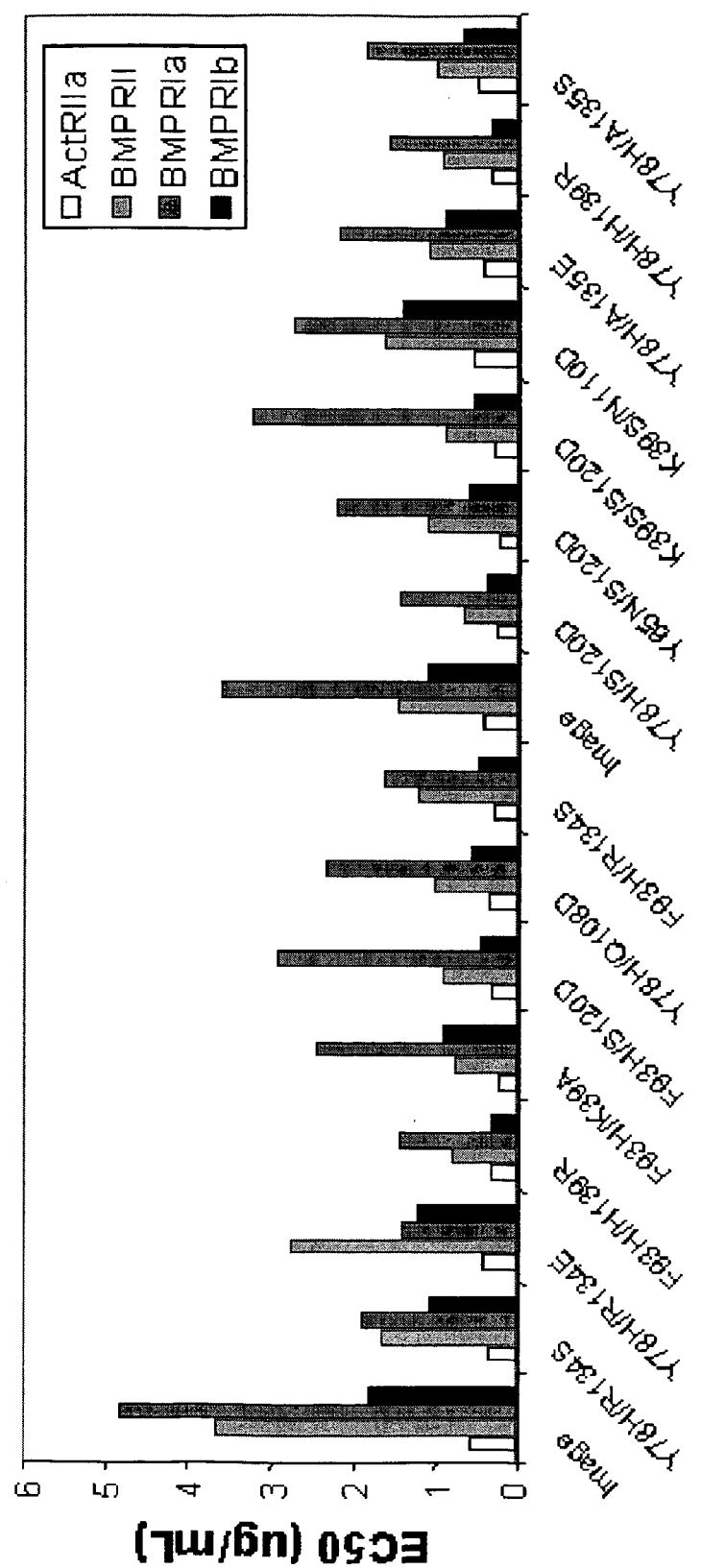
FIG. 8 shows a summary of 12-point receptor binding curves for wild type human BMP-7 (Image clone) and variants.
Figure 9:
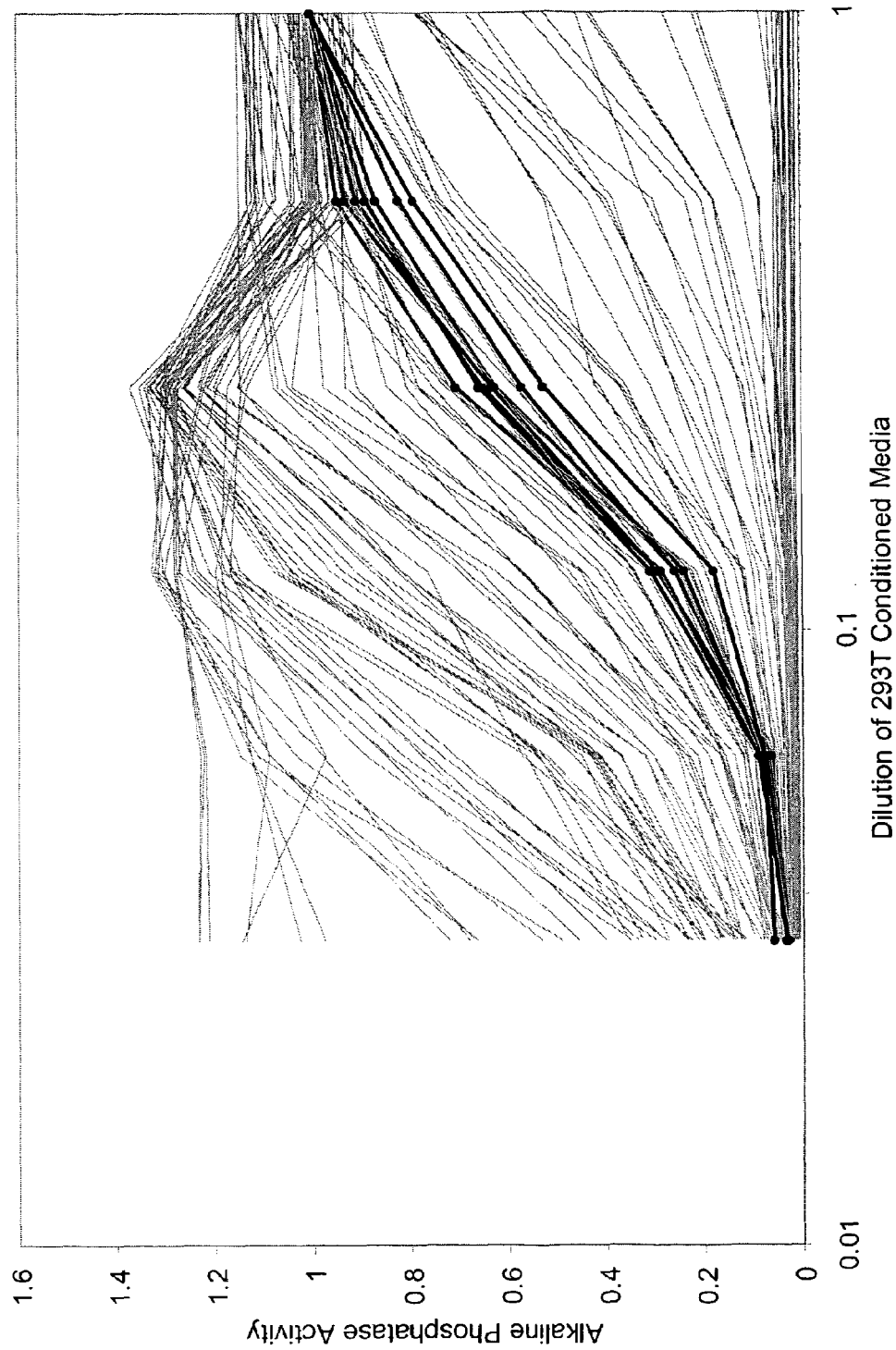
FIG. 9 shows dose-response C2C12 biassay data for selected Library 2 variants.
Figure 10:
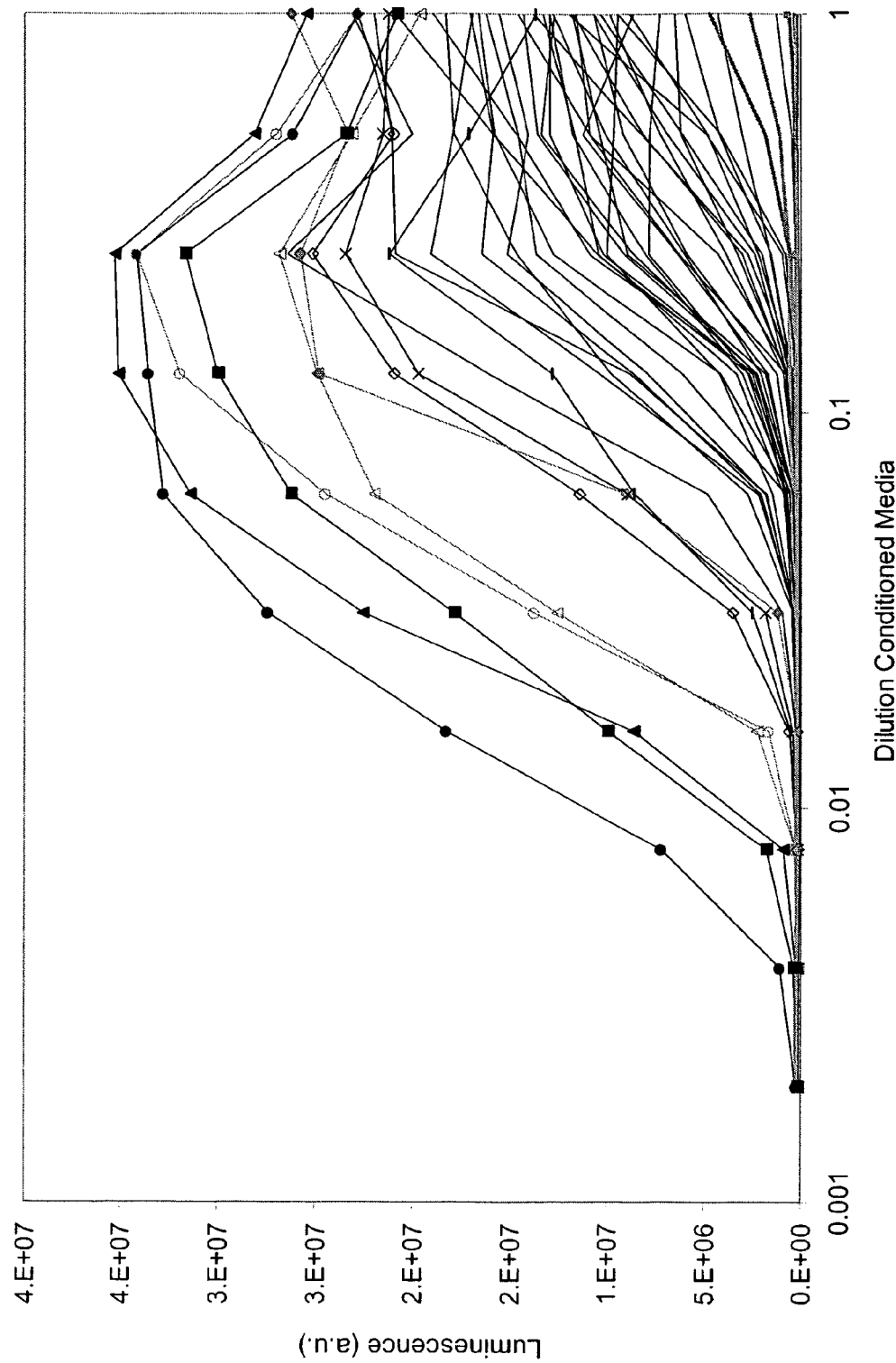
FIG. 10 shows dose-response C2C12 biassay data for selected Library 3 variants, Library 1 variants (thick gray lines, no markers), and wild type (thick black line, no markers).
Figure 11:
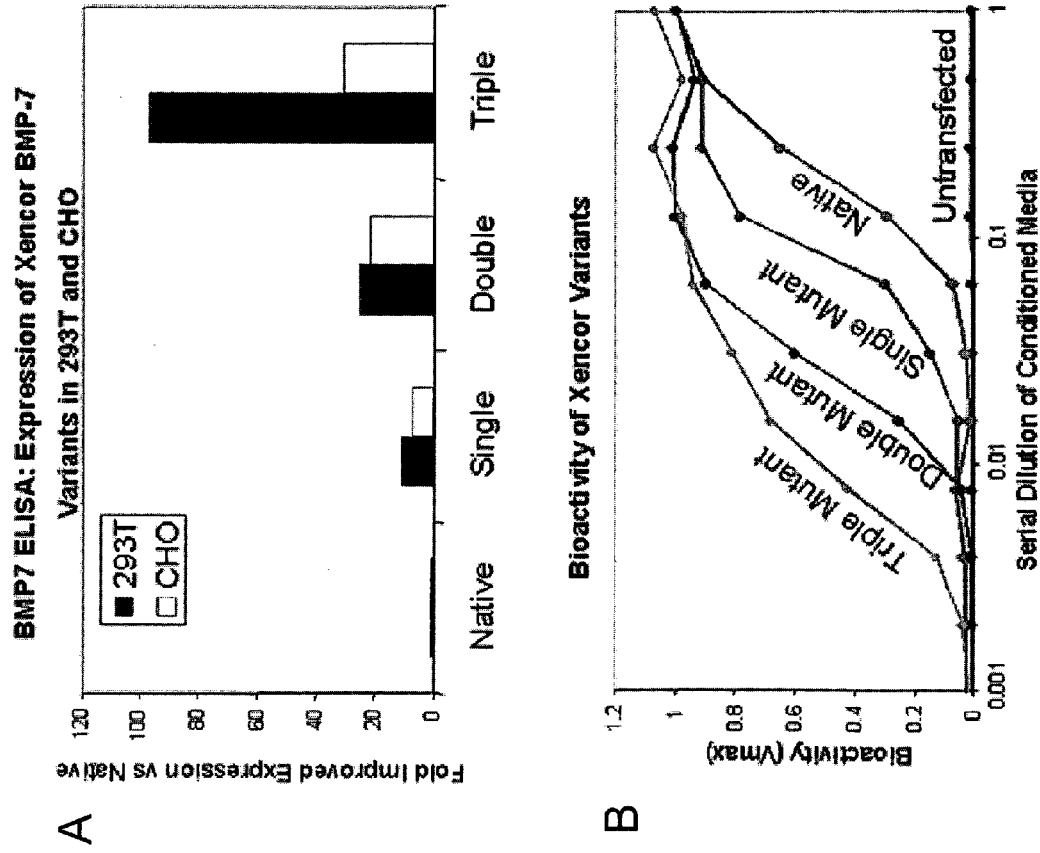
FIG. 11 shows (A) ELISA quantitation of the expression yield of the best single, double, and triple variants in 293T cells (black bars) and CHO cells (white bars) and (B) that enhanced expression yield of the best-expressing single, double, and triple mutant variants results in increased C2C12 bioactivity from serially diluted conditioned media.
Figure 12:
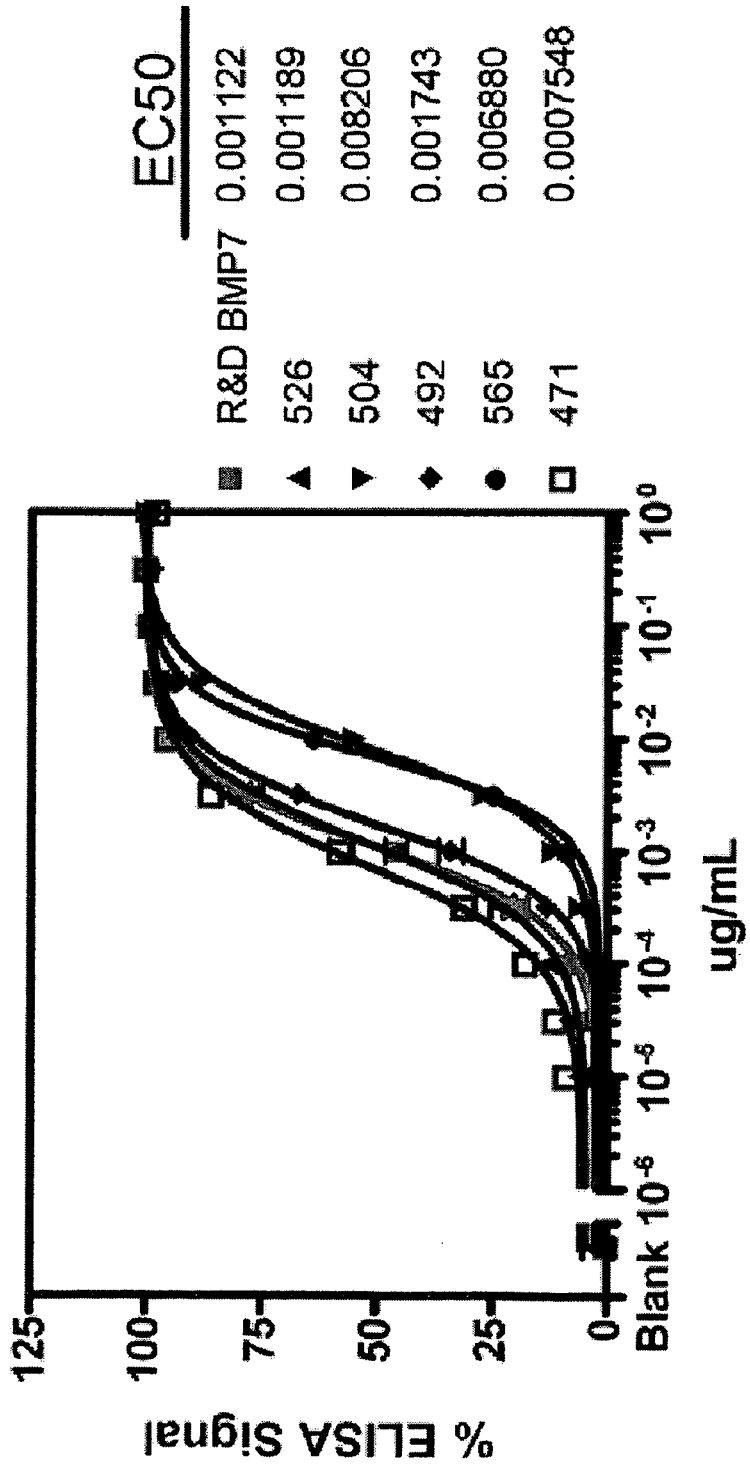
FIG. 12 shows appropriate correction factors when using a commercial ELISA (R&D Systems) to determine the concentration of selected BMP-7 variants.
Figure 13:
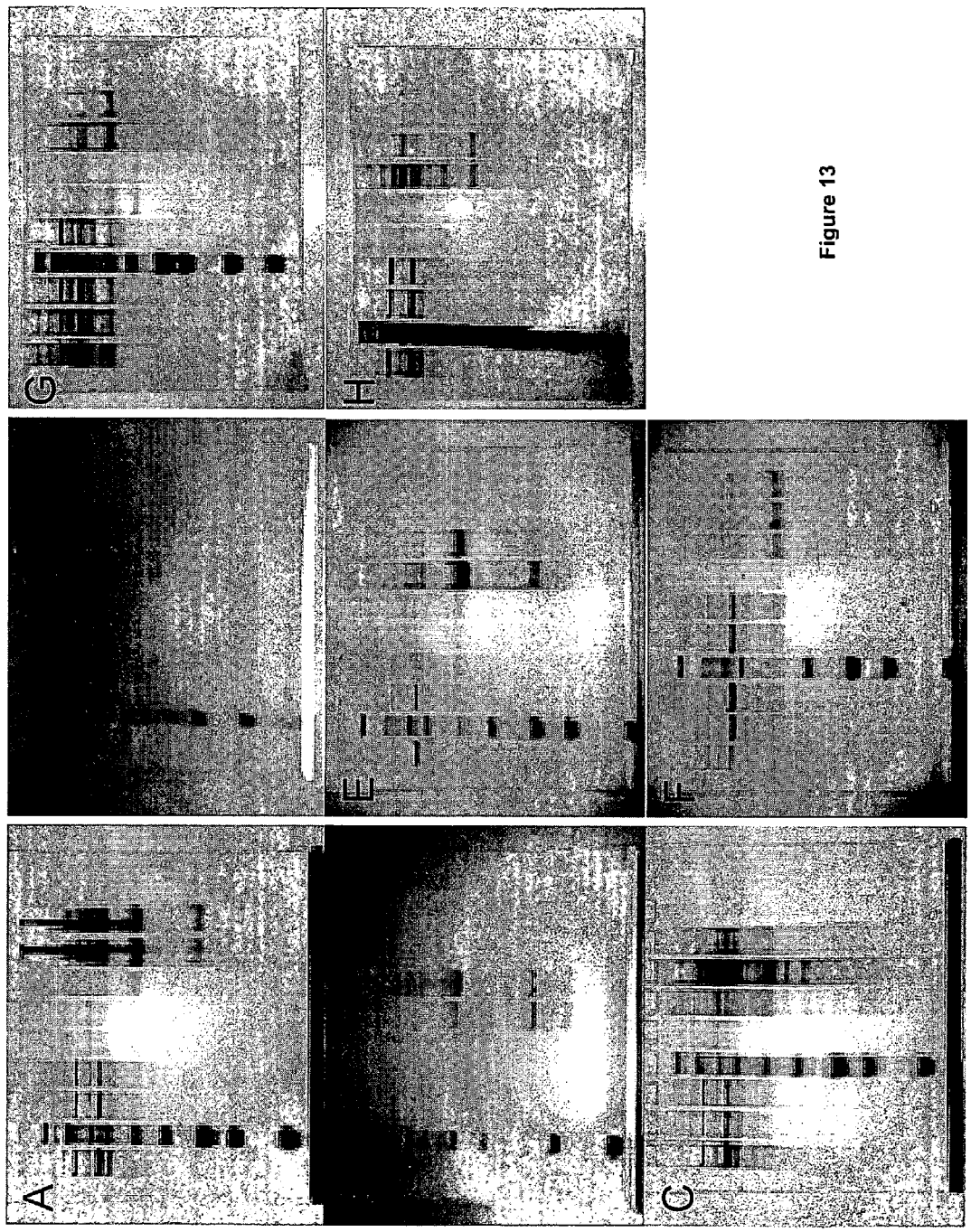
FIG. 13 shows purification of selected BMP-7 variants.
Figure 14:
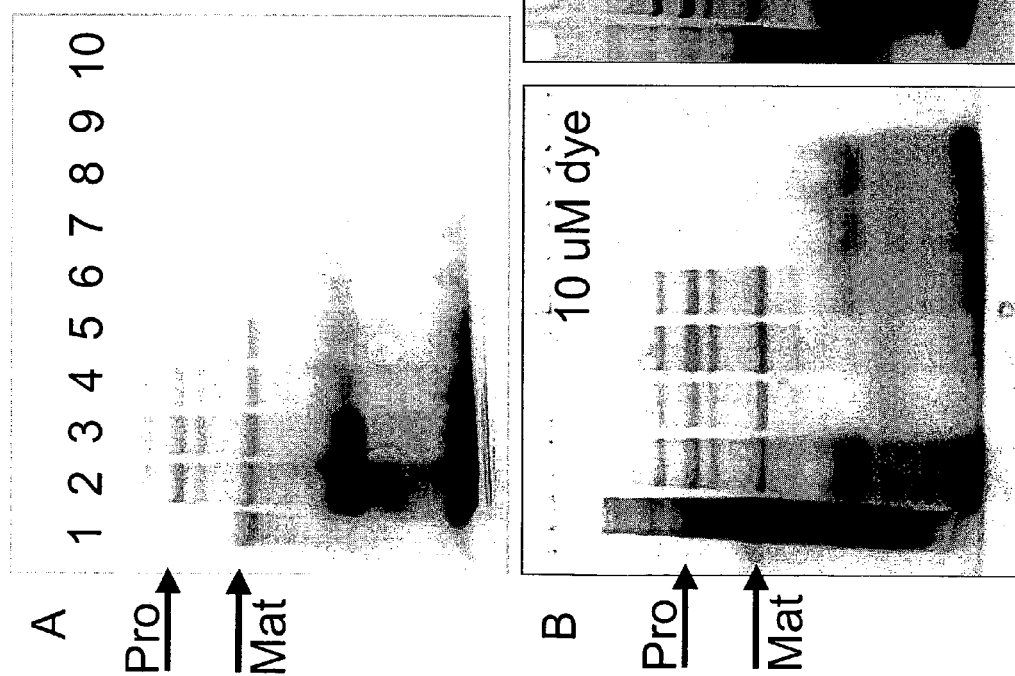
FIG. 14 shows fluorescence images of SDS-PAGE gels showing (A) Alexa 568 labeling of BMP-7 variant Y65N/S120D as a function of dye concentration; and (B) scale-up of Alexa-568 labeled Y65N/S120D BMP-7.
Figure 15:
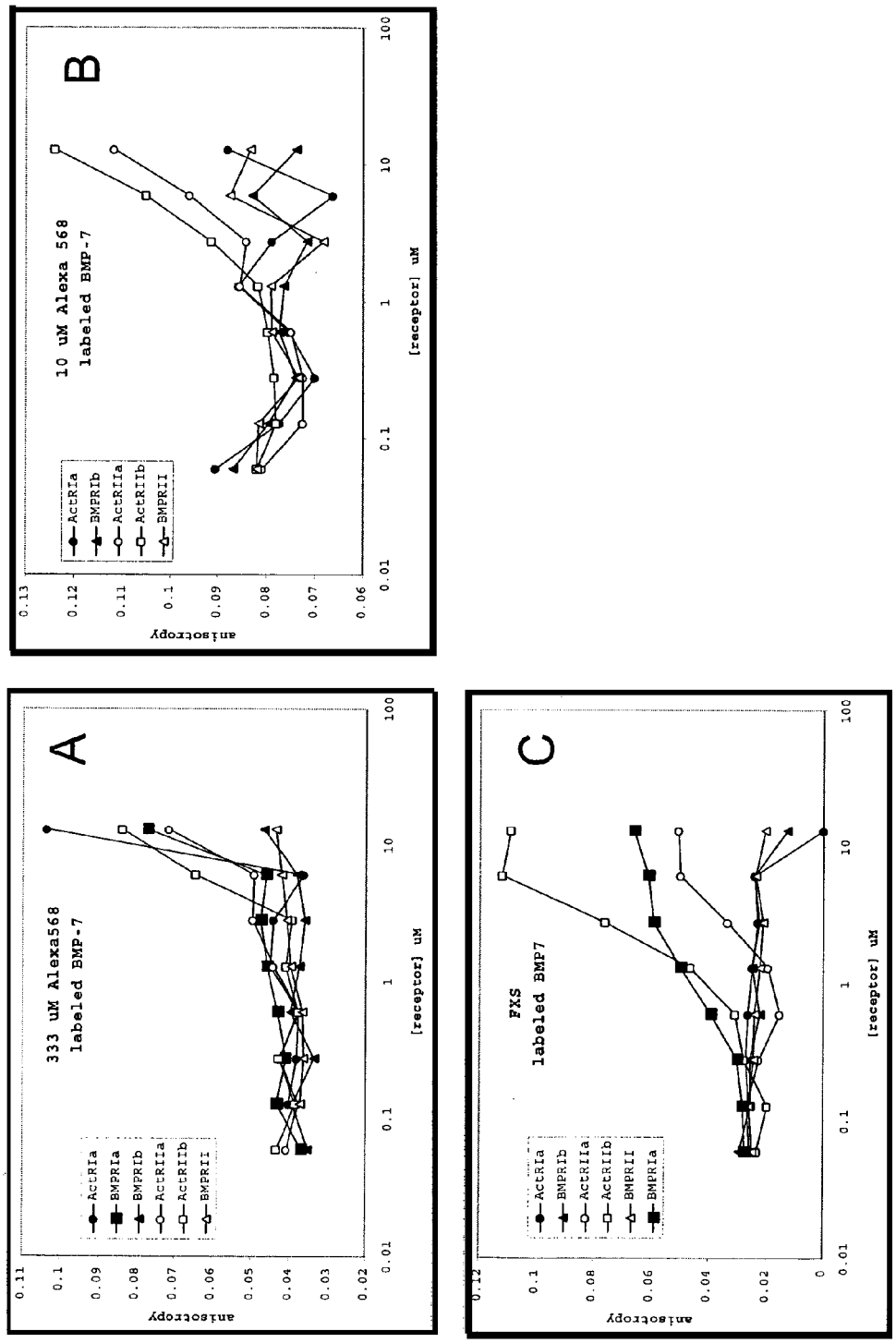
FIG. 15 shows fluorescence anisotropy as a function of receptor concentration.
Figure 16:
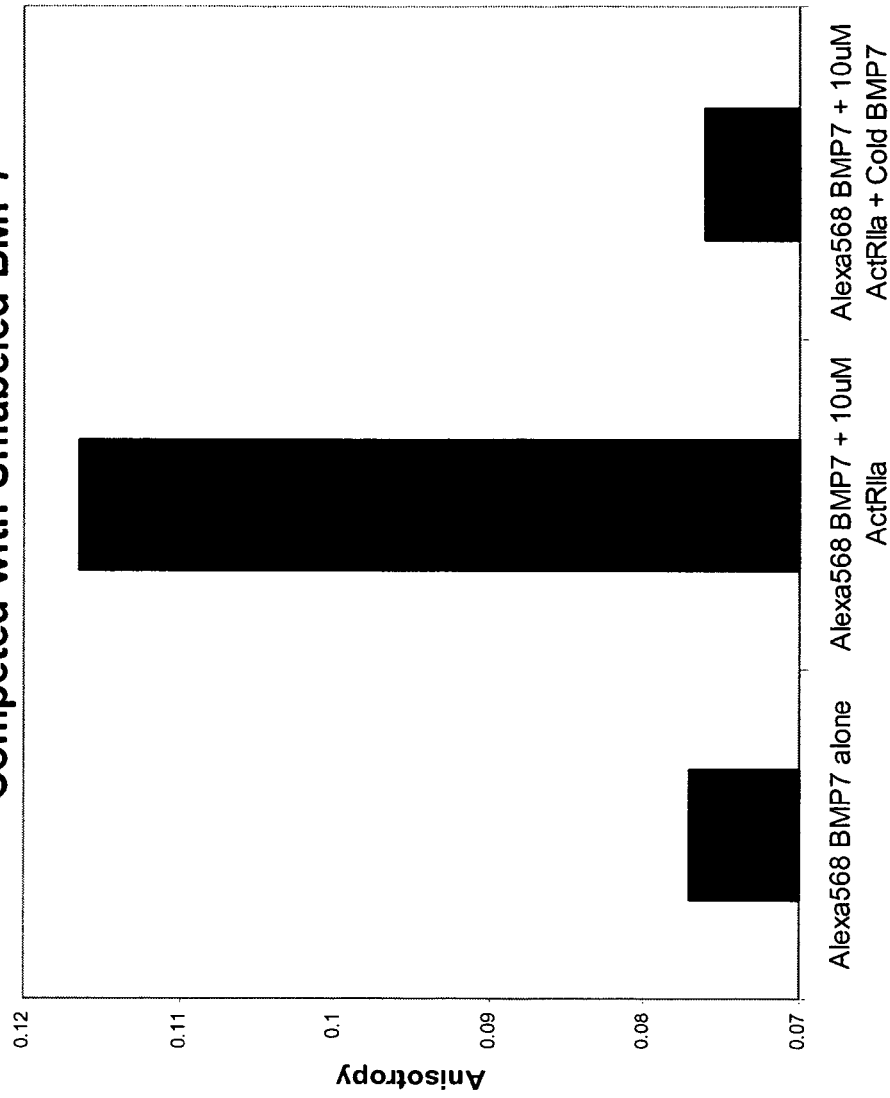
FIG. 16 shows that binding of Alexa568-labeled Y65N/S120D BMP-7 to the receptor ActRIIa can be competed with unlabeled BMP-7.
Figure 17:
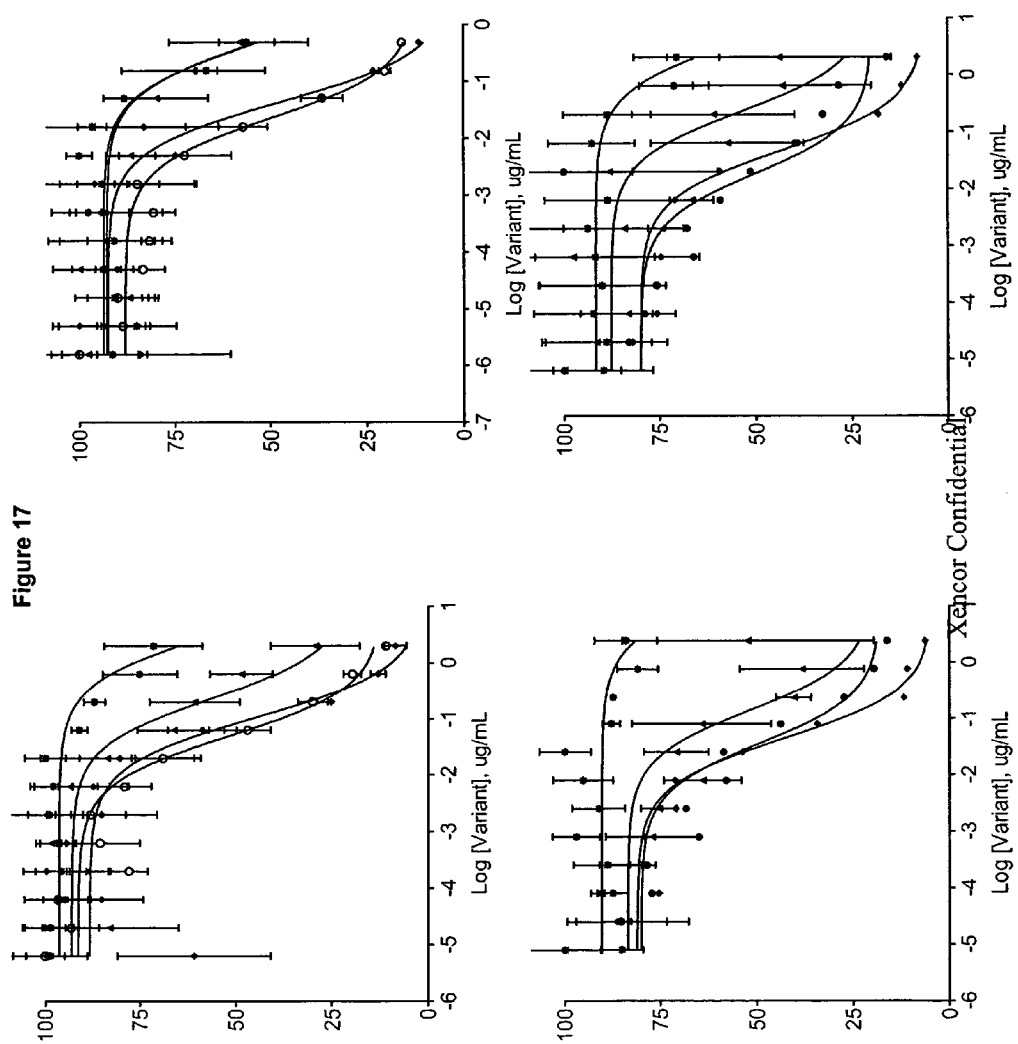
FIG. 17 shows competitive binding of (A) recombinant human BMP-7 (R&D Systems), (B) BMP-7 variant 565 (Y65N/F93T/R129D), (C) BMP-7 variant 526 (K39S/S120D/R134E), and (D) BMP-7 variant 504 (Y65N/S120D) to the BMP receptors and inhibitors BMPRIb (open circles), ActRIIa (closed diamonds), BMPRII (closed triangles), and Noggin (stars) determined using AlphaScreen.
Figure 18:
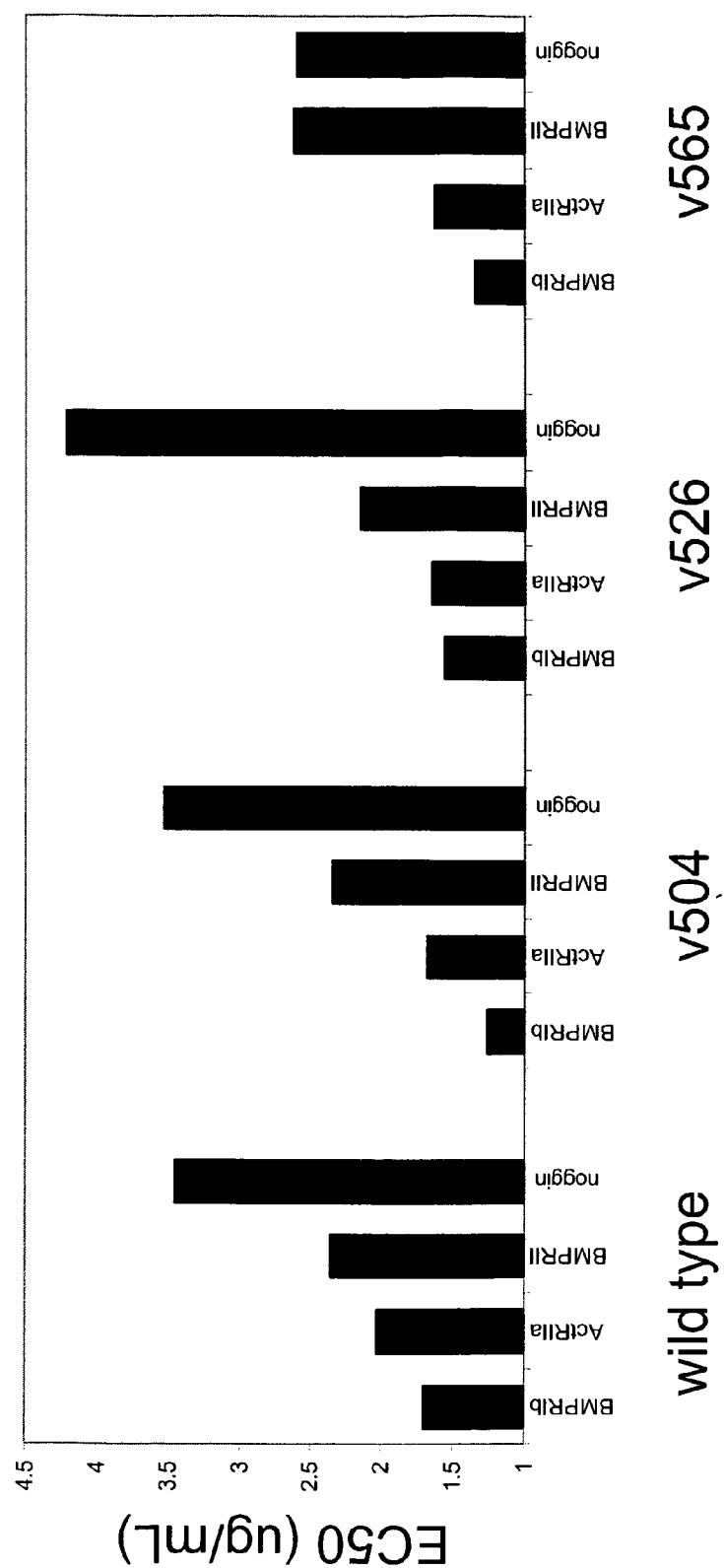
FIG. 18 shows a bar graph indicating the EC50 of binding for four BMP-7 variants to three receptors and one inhibitor.

Homology modeling was used to generate structures of additional BMP receptors bound to BMP-2 and BMP-7. As shown in FIG. 5, the sequences of ALK-2 and ALK-6 were aligned with ALK-3, and the sequences of ActRIIb and BMPRII were aligned with ActRIIa. The Modeler tool in InsightiII (Accelrys) was used to generate the homology models. Disulfide pairs were manually constrained as follows (using the crystallographic numbering from 1LX5 and 1ES7): Alk3: 238-259, 240-244, 253-277, 287-301, 302-307; ActRIIa: 11-41, 31-59, 66-85, 72-84, and 86-91. Three models were generated for each molecule; the model with the best energy and -lnPDF score was selected for subsequent PDA® technology calculations. Homology modeling was also used to generate structures of BMP-4, BMP-5, BMP-6, and BMP-8. BMP-4 was modeled using the BMP-2 structure while BMP-5, BMP-6, and BMP-8 were modeled using the BMP-7 structure. The BMP sequences were aligned as shown in FIG. 3 (SEQ ID NOS:7-12). PDA® technology calculations were used to model the BMP-4, BMP-5, BMP-6, and BMP-8 structures.

Example 2

Identification of Exposed Hydrophobic Residues in BMPs

Structures of BMP-7 dimer ("dimer") and BMP-7 dimer bound to ALK-3 and ActRIIa ("hexamer") were analyzed to identify solvent-exposed hydrophobic residues. The absolute and fractional solvent-exposed hydrophobic surface area of each residue was calculated using the method of Lee and Richards (J. Mol. Biol. 55: 379-400 (1971)) using an add-on radius of 1.4 Å (Angstroms). Each residue was also classified as core, boundary, or surface (see Dahiyat and Mayo Science 278: 82-87 (1997)).

Solvent exposed hydrophobic residues in BMP-7 were defined to be hydrophobic with at least 50 Å$^2$ (square Angstroms) exposed hydrophobic surface area in the BMP-7 dimer (PDB code 1LX5, chain A, plus symmetry-related BMP-7 molecule). Exposed hydrophobic surface area was also measured in the context of the BMP-7/ALK-2/ActRIIa hexamer and RESCLASS was run to categorize each position as core, boundary, or surface.

TABLE 1

Exposed hydrophobic residues in BMP-7.

| # | wt | dimer RC | hexamer RC | dimer expH | hexamer expH |
|---|-----|----------|------------|------------|--------------|
| 44 | TYR | surface | surface | 85.5 | 95.5 |
| 52 | TRP | boundary | core | 82.9 | 5.9 |
| 55 | TRP | boundary | boundary | 168.4 | 125.5 |
| 57 | ILE | boundary | core | 70.3 | 29.8 |
| 73 | PHE | surface | core | 70.5 | 64.6 |
| 78 | TYR | surface | core | 107.9 | 71.2 |
| 86 | ILE | surface | core | 60.7 | 4.3 |
| 90 | LEU | boundary | core | 51.7 | 10.6 |
| 93 | PHE | boundary | core | 113.1 | 10.9 |
| 94 | ILE | boundary | core | 79.0 | 37.3 |
| 115 | LEU | surface | core | 56.9 | 0.0 |
| 116 | TYR | boundary | core | 51.5 | 51.6 |
| 117 | PHE | surface | boundary | 97.5 | 25.4 |
| 123 | VAL | surface | core | 86.0 | 14.4 |
| 125 | LEU | surface | core | 88.4 | 60.9 |
| 128 | TYR | boundary | core | 64.9 | 17.4 |

Example 3

Identification of Receptor and Inhibitor Interface Residues in BMP-7

Potential sites of interactions between BMP-7 and ALK-3, BMP-7 and ActRIIa, and BMP-7 and noggin were identified by examining the structure of the hexameric structure described in Example 1 and the co-crystal structure of BMP-7 and noggin (PDB code 1M4U). Next, distance measurements were used to identify residues that may participate in intermolecular interactions. Residues in BMP-7 that are within 5 Å (Angstroms) of the ALK-3, ActRIIa, or noggin interfaces (as measured by CA-CA distances) are shown below, along with the receptor or inhibitor positions that are contacted. Next, the receptor sequence alignments used for homology modeling were analyzed for polymorphisms. Information about receptor polymorphisms was used to design receptor-specific variants, described below. If the receptor positions are polymorphic, it is noted in Table 2; "na" indicates that the receptor positions were not sufficiently well-aligned to unambiguously identify the polymorphisms. However, receptor-specific BMP variants may be identified that contact such unaligned regions of the receptors.

TABLE 2

BMP-7 receptor and inhibitor contacts

| # | Wt | Contacts: A, B = ALK-3; D, F = ActRIIa; and N = noggin | receptor polymorphisms |
|---|-----|------------|------------|
| 39 | LYS | ASP A 246 | 246 (ALK6 = E, ALK3 = D, ALK2 na) |
| 44 | TYR | ASN D 65, ILE D 64, ASP D 63 | 65(ActRIIa, ActRIIb N, BMPRII na), 64(ActRIIb = F, ActRIIa = I, BMPRII na), 63(ActRIIa, ActRIIb D, BMPRII na) |
| 47 | PHE | PHE B 285 | 285(ALK6, ALK3 = F, ALK2 = M) |
| 48 | ARG | LYS D 76, GLN N 208, ARG N 209, ARG N 210 | 76(ActRIIb = E, ActRIIa = K, BMPRII = T) |
| 49 | ASP | LYS B 292 | na |
| 50 | LEU | SER B 290, PHE B 285 | 290(ALK6 = T, ALK3 = S, ALK2 = P), 285(ALK6, ALK3 = F, ALK2 = M) |
| 51 | GLY | PRO B 291, SER B 290, LYS B 292 | 291 P conserved, 290(ALK6 = T, ALK3 = S, ALK2 = P), 292 na |
| 52 | TRP | PHE B 285, LYS B 288, SER B 290, PRO B 291, ILE N 33, ARG N 34, PRO N 35 | 285(ALK6, ALK3 = F, ALK2 = M), 288(ALK6 = R, ALK3, ALK2 = K), 290(ALK6 = T, ALK3 = S, ALK2 = P), 291 P conserved |

TABLE 2-continued

BMP-7 receptor and inhibitor contacts

| # | Wt | Contacts: A, B = ALK-3; D, F = ActRIIa; and N = noggin | receptor polymorphisms |
|---|----|---------------------------------------------------------|------------------------|
| 53 | GLN | LYS D 76, ARG N 206 | 76 (ActRIIb = E, ActRIIa = K, BMPRII = T) |
| 54 | ASP | LYS B 288, GLU D 80, ARG N 206, GLN N 208 | 288(ALK6 = R, ALK3, ALK2 = K), 80(ActRIIb = Q, ActRIIa = E, BMPRII na) |
| 55 | TRP | LYS B 288, ARG N 34, PRO N 35 | 288(ALK6 = R, ALK3, ALK2 = K) |
| 56 | ILE | PHE B 285 | 285(ALK6, ALK3 = F, ALK2 = M) |
| 57 | ILE | PHE D 83, VAL D 81, THR D 44, ARG N 204, ARG N 206, ILE N 218 | 83 F conserved, 81(ActRIIa, ActRIIb V, BMPRII na), 44(ActRIIb = S, ActRIIa = T, BMPRII = L) |
| 58 | ALA | PHE D 83, TRP D 60, LEU N 46, GLU N 48, ARG N 204 | 60 W conserved, 83 F conserved |
| 59 | PRO | ASP D 63, ASN D 65, TRP D 60, PHE D 83, LEU N 46, ILE N 47 | 63(ActRIIa, ActRIIb D, BMPRII na), 65(ActRIIa, ActRIIb N, BMPRII na), 60 W conserved, 83 F conserved |
| 60 | GLU | LYS D 76, ASN D 65, GLU D 74, PHE N 54 | 76(ActRIIb = E, ActRIIa = K, BMPRII = T), 65(ActRIIa, ActRIIb N, BMPRII na), 74(ActRIIb = A, ActRIIa = E, BMPRII = V) |
| 61 | GLY | ASN D 65 | 65(ActRIIa, ActRIIb N, BMPRII na) |
| 62 | TYR | ASP D 63, ASN D 65, ILE D 64 | 63(ActRIIa, ActRIIb D, BMPRII na), 65(ActRIIa, ActRIIb N, BMPRII na), 64(ActRIIb = F, ActRIIa = I, BMPRII na) |
| 63 | ALA | ILE D 64 | 64(ActRIIb = F, ActRIIa = I, BMPRII na) |
| 73 | PHE | ARG A 297, GLU A 264, ILE N 33 | 297(ALK6, ALK3 = R, ALK2 = Q) 264(ALK6, ALK3 = E, ALK2 = S) |
| 74 | PRO | HIS A 243, ILE A 262, ILE A 299, PHE A 260, GLU A 264, GLN A 286, MET A 278, LEU N 31, ILE N 33 | 243(ALK3, ALK6 H, ALK2 na), 262(ALK6 = M, ALK3 = I, ALK2 = S), 299(ALK6, ALK3 = I ALK2 = V), 260 F conserved, 264(ALK6, ALK3 = E, ALK2 = S), 286(ALK6, ALK3 = Q ALK2 = T), 278(ALK6 = L, ALK3 = M, ALK2 = F) |
| 75 | LEU | GLN A 286, TYR N 30, LEU N 31, HIS N 32, ILE N 33 | 286(ALK6, ALK3 = Q ALK2 = T) |
| 76 | ASN | HIS A 243, PHE A 260, GLY A 276, MET A 278, PRO A 245, CYS A 277, TYR N 30, LEU N 31, HIS N 32 | 243(ALK3, ALK6 H, ALK2 na), 260 F conserved, 276 G conserved, 278(ALK6 = L, ALK3 = M, ALK2 = F), 245(ALK3, ALK6 P, ALK2 na), 277 C conserved |
| 77 | SER | CYS A 277, CYS A 253, THR A 255, PHE A 260, LYS A 279, GLY A 276, MET A 278, PRO A 245, MET N 27, HIS N 29, TYR N 30, HIS N 32 | 277 C conserved, 253 C conserved, 255(ALK3, ALK6 T, ALK2 na), 260 F conserved, 279(ALK6 = G, ALK3 = K, ALK2 na), 276 G conserved, 278(ALK6 = L, ALK3 = M, ALK2 = F), 245(ALK3, ALK6 P, ALK2 na) |
| 78 | TYR | ASP A 246, PRO A 245, ASP A 247 | 246(ALK6 = E, ALK3 = D, ALK2 na), 245(ALK3, ALK6 P, ALK2 na), 247(ALK3, ALK6 D, ALK2 na) |
| 80 | ASN | LYS A 279 | 279(ALK6 = G, ALK3 = K, ALK2 na) |
| 83 | ASN | GLU A 281, GLY A 282, PHE A 285, ARG N 34, PRO N 35, ALA N 36 | 281(ALK3, ALK6, 282 ALK2 na), 282(ALK3, ALK6 G, ALK2 na), 285(ALK6, ALK3 = F ALK2 = M) |
| 86 | ILE | GLN A 286, GLY A 282, PHE A 285, HIS N 32, ILE N 33, ARG N 34, PRO N 35 | 286(ALK6, ALK3 = Q ALK2 = T), 282(ALK3, ALK6 G, ALK2 na), 285(ALK6, ALK3 = F ALK2 = M) |
| 87 | VAL | PRO N 35 | |
| 90 | LEU | ASP A 289, SER A 290, PHE A 285, ARG A 297, GLN A 286, ILE N 33 | 289(ALK6, ALK3 = D ALK2 = T), 290(ALK6 = T ALK3 = S ALK2 = P), 285(ALK6, ALK3 = F ALK2 = M), 297(ALK6, ALK3 = R ALK2 = Q), 296(ALK3, ALK6 R, ALK2 na) |
| 93 | PHE | ALA A 293, ARG A 297, ASP A 289, LEU A 295, SER A 290, GLN A 294, GLU A 264 | 293(na), 295(na), 294(na), 297(ALK6, ALK3 = R ALK2 = Q), 289(ALK6, ALK3 = D ALK2 = T), 290(ALK6 = T ALK3 = S ALK2 = P), 264(ALK6, ALK3 = E ALK2 = S) |
| 94 | ILE | SER A 290, LYS A 292, ALA A 293 | 290(ALK6 = T ALK3 = S ALK2 = P), 292(na), 293(na) |

TABLE 2-continued

BMP-7 receptor and inhibitor contacts

| # | Wt | Contacts: A, B = ALK-3; D, F = ActRIIa; and N = noggin | receptor polymorphisms |
|---|---|---|---|
| 108 | GLN | ASP D 36 | 36(ActRII, ActRIIb D, BMPRII N) |
| 110 | ASN | LYS D 37, ASP D 62, ASP D 36 | 36(ActRII, ActRIIb D, BMPRII N), 37(ActRII, ActRIIa K, BMPRII na), 62 D conserved |
| 111 | ALA | LEU D 61, LYS D 37 | 61(ActRIIa, ActRIIb L, BMPRII G), 37(ActRII, ActRIIa K, BMPRII na) |
| 112 | ILE | LEU D 61 | 61(ActRIIa, ActRIIb L, BMPRII G) |
| 113 | SER | LEU D 61, TRP D 60, LEU N 43, VAL N 44, ASP N 45, LEU N 46 | 61(ActRIIa, ActRIIb L, BMPRII G), 60 W conserved |
| 114 | VAL | TRP D 60, LEU N 46 | 60 W conserved |
| 115 | LEU | PHE D 83, TRP D 60, PHE D 42, THR D 44, LYS D 56, LEU N 46, PHE N 168, ARG N 204, ILE N 220 | 83 F conserved, 60 W conserved, 56 K conserved, 42(ActRIIb, BMPRII = Y, ActRIIa = F), 44(ActRIIb = S, ActRIIa = T, BMPRII = L) |
| 116 | TYR | ASP B 284, PRO N 37 | 284(ALK6, ALK3 = D ALK2 = K) |
| 117 | PHE | VAL D 81, GLU D 80, ARG N 206, ILE N 218 | 81(ActRIIa, ActRIIb V, BMPRII na), 80(ActRIIb = Q, ActRIIa = E, BMPRII na) |
| 119 | ASP | HIS N 29 | |
| 122 | ASN | ARG D 20, ASN D 17, GLN N 221 | 20(ActRIIb = L, ActRIIa = K, BMPRII na), 17(ActRIIa, ActRIIb N, BMPRII na) |
| 123 | VAL | VAL D 81, VAL D 55, LYS D 56, THR D 44, LYS D 46, ILE N 218, PRO N 219, ILE N 220, GLN N 221 | 81(ActRIIa, ActRIIb V, BMPRII na), 55 V conserved, 56 K conserved, 44(ActRIIb = S, ActRIIa = T, BMPRII = L), 46(ActRIIb = A, ActRIIa = K, BMPRII = E), |
| 124 | ILE | HIS N 199, GLN N 221 | |
| 125 | LEU | TRP D 60, PHE D 42, LYS D 56, LEU N 43, ASP N 45, LEU N 46, GLN N 221, TYR N 222, PRO N 223 | 60 W conserved, 56 K conserved, 42(ActRIIb, BMPRII = Y, ActRIIa = F) |
| 126 | LYS | TYR B 280, GLU B 281, ASP B 284, PRO N 37, SER N 38, ASP N 39, LEU N 43, HIS N 199 | 280(ALK6 = L ALK3 = Y ALK2 na), 281(ALK2 na), 284(ALK6, ALK3 = D ALK2 = K) |
| 127 | LYS | LEU D 61, LYS D 37, ALA N 36, PRO N 37, SER N 38, ASN N 40, LEU N 41, PRO N 42, LEU N 43 | 37(ActRII, ActRIIa K, BMPRII na), 61(ActRIIa, ActRIIb L, BMPRII G), 36(ActRII, ActRIIb D, BMPRII N) |
| 128 | TYR | ASP B 284, PHE B 285, PRO N 35, ALA N 36, PRO N 37, SER N 38 | 284(ALK6, ALK3 = D ALK2 = K), 285(ALK6, ALK3 = F ALK2 = M) |
| 129 | ARG | GLU B 281, ASN E 83, ALA N 36, SER N 38, ASN N 40 | 281(ALK3, ALK6 E, ALK2 na) |
| 130 | ASN | GLU B 281 | 281(ALK3, ALK6 E, ALK2 na) |
| 131 | MET | PHE B 285, PRO N 35 | 285(ALK6, ALK3 = F ALK2 = M) |
| 134 | ARG | ASP D 36 | 36(ActRII, ActRIIb D, BMPRII N) |

Example 4

Identification of Regions of High Electrostatic Potential in BMP-7

The electrostatic potential at each position in BMP-7 was determined using the Debye-Huckel equation in the context of the BMP-7 dimer. Positions with electrostatic potential greater than 0.5 or less than −0.5 are listed in the table below; modifications at these positions may confer increased stability or receptor binding specificity.

TABLE 3

Regions of high electrostatic potential in BMP-7

| Residue number | Residue name | Electrostatic potential |
|---|---|---|
| 46 | SER | −0.72 |
| 67 | CYS | 0.73 |
| 68 | GLU | 0.50 |
| 69 | GLY | 0.58 |
| 70 | GLU | 0.55 |

TABLE 3-continued

Regions of high electrostatic potential in BMP-7

| Residue number | Residue name | Electrostatic potential |
|---|---|---|
| 71 | CYS | 0.50 |
| 72 | ALA | 0.62 |
| 82 | THR | 0.57 |
| 105 | ALA | 0.54 |
| 106 | PRO | 0.67 |
| 107 | THR | 0.65 |
| 108 | GLN | 0.68 |
| 109 | LEU | 0.79 |
| 110 | ASN | 1.00 |
| 111 | ALA | 1.51 |
| 113 | SER | 0.68 |
| 122 | ASN | −0.64 |
| 133 | VAL | 0.68 |
| 135 | ALA | 0.53 |
| 136 | CYS | 0.62 |

Example 5

Identification of Preferred Substitutions to BMPs

Analogous contact environment (ACE) calculations, were performed on BMP-7 using complete PFAM alignment for BMP-7. ACE calculations identify alternate residues for each position that are observed in structurally similar contexts in homologous proteins. The calculations were performed using a low stringency threshold of 0.8 and a high stringency threshold of 0.5.

TABLE 4

Residues observed in analogous structural contexts in BMP-7 homologs

| residue | Wt | ACE, low stringency | ACE, high stringency |
|---|---|---|---|
| 36 | GLN | E Q T | Q T |
| 37 | ALA | A G S V | A G |
| 38 | CYS | C | C |
| 39 | LYS | K R | K |
| 40 | LYS | K R T | K |
| 41 | HIS | H K R | H |
| 42 | GLU | E S | E |
| 43 | LEU | F L M P | L P |
| 44 | TYR | F Y | F Y |
| 45 | VAL | I R V | V |
| 46 | SER | D E N S | S |
| 47 | PHE | F L S | F |
| 48 | ARG | K Q R | K Q R |
| 49 | ASP | A D E Q | D |
| 50 | LEU | F I L M V | L V |
| 51 | GLY | D G N | G N |
| 52 | TRP | W | W |
| 53 | GLN | D H L N Q R S | D H L N Q S |
| 54 | ASP | D N R | D N |
| 55 | TRP | W | W |
| 56 | ILE | I V | I |
| 57 | ILE | I V | I |
| 58 | ALA | A K Q S Y | A |
| 59 | PRO | P | P |
| 60 | GLU | A E G H K M P Q R S T | A E K M P Q R S |
| 61 | GLY | G | G |
| 62 | TYR | F Y | Y |
| 63 | ALA | A D E G H M N Q S | A M Q S |
| 64 | ALA | A G | A |
| 65 | TYR | F N Y | F N Y |
| 66 | TYR | F Y | Y |
| 67 | CYS | C | C |
| 68 | GLU | A D E H K Q R | D E |
| 69 | GLY | G | G |
| 70 | GLU | E | E |
| 71 | CYS | C | C |
| 72 | ALA | A D N P S V | A N S V |
| 73 | PHE | F | F |
| 74 | PRO | P | P |
| 75 | LEU | L | L |
| 76 | ASN | A D N S | N |
| 77 | SER | A S | A S |
| 78 | TYR | C F H Y | C F H Y |
| 79 | MET | A M | M |
| 80 | ASN | N | N |
| 81 | ALA | A F G P S T | A |
| 82 | THR | T | T |
| 83 | ASN | K N S | N |
| 84 | HIS | H | H |
| 85 | ALA | A | A |
| 86 | ILE | I L V | I |
| 87 | VAL | I L M V | V |
| 88 | GLN | K Q | Q |
| 89 | THR | L T | T |
| 90 | LEU | L | L |
| 91 | VAL | V | V |
| 92 | HIS | H N | H |
| 93 | PHE | A F L S | F S |
| 94 | ILE | F I | I |
| 95 | ASN | N | N |
| 96 | PRO | P | P |
| 97 | GLU | A D E G K N Q R S | D E |
| 98 | THR | A K R T | T Y |
| 99 | VAL | T V | V |
| 100 | PRO | G P | P |
| 101 | LYS | K L Q | K Q |
| 102 | PRO | A P S T V W | P |
| 103 | CYS | C K | C |
| 104 | CYS | C W | C |
| 105 | ALA | A G H I Q R S T V | A |
| 106 | PRO | N P | P |
| 107 | THR | T | T |
| 108 | GLN | K Q | K Q |
| 109 | LEU | L | L |
| 110 | ASN | H N | N |
| 111 | ALA | A G S | A |
| 112 | ILE | I L T | I |
| 113 | SER | P S T | P S |
| 114 | VAL | I L M V | L M V |
| 115 | LEU | L | L |
| 116 | TYR | F Y | Y |
| 117 | PHE | F I K L Q Y | F Y |
| 118 | ASP | D | D |
| 119 | ASP | D E N S | D E N S |
| 120 | SER | D E G H N S | N S |
| 121 | SER | A D E H K N R S | A D S |
| 122 | ASN | A N S | N |
| 123 | VAL | I L V | V |
| 124 | ILE | I V | I V |
| 125 | LEU | I K L Y | L Y |
| 126 | LYS | K N R Y | K R |
| 127 | LYS | K R | K |
| 128 | TYR | F Y | Y |
| 129 | ARG | R | R |
| 130 | ASN | D N | N |
| 131 | MET | M | M |
| 132 | VAL | V | V |
| 133 | VAL | A V | V |

TABLE 4-continued

Residues observed in analogous structural contexts in BMP-7 homologs

| residue | Wt | ACE, low stringency | ACE, high stringency |
|---|---|---|---|
| 134 | ARG | Q R | Q R |
| 135 | ALA | A G S | A |
| 136 | CYS | C | C |
| 137 | GLY | A G | G |
| 138 | CYS | C | C |
| 139 | HIS | G H K L Q R | H L |

PDA® technology calculations were performed to identify alternate residues that are compatible with the structure and function of BMP-7. At each variable position, energies were calculated for the wild type residue and alternate residues with decreased hydrophobic or increased polar character. First, point mutation calculations were run for each template. The energy of each alternate amino acid in its most favorable rotameric conformation was compared to the energy of the wild type residue in the crystallographically observed rotameric conformation; all reported energies in the table below are [E(wild type)-E(variant)]. For residues that are within 5 Å of at least one atom in the type I or type II receptor, calculations were also performed using templates consisting of the BMP-7 dimer bound to receptor.

TABLE 5

Energies of most favorable alternate residues in each variable position in BMP-7

| # | Wt | dimer | ALK2 | ALK3 | ALK6 | ActRIIa | ActRIIb |
|---|---|---|---|---|---|---|---|
| 36 | GLN | N: −4.8 | | N: 0.4 | | N: −6.6 | |
| | | D: −3.7 | | Q: 0.8 | | Q: −5.6 | |
| | | S: −3.0 | | D: 0.8 | | D: −5.2 | |
| 39 | LYS | E: −11.9 | T: 0.0 | T: 1.4 | S: 2.7 | E TABLE 5-continued Energies of most favorable alternate residues in each variable position in BMP-7

| # | Wt | dimer | ALK2 | ALK3 | ALK6 | ActRIIa | ActRIIb |
|---|---|---|---|---|---|---|---|
| 78 | TYR | N: −15.6 | S: 3.2 | S: 3.2 | S: 3.2 | N: −13.2 | R: −12.8 |
|  |  | D: −14.6 | D: 6.4 | A: 6.4 | T: 6.4 | D: −12.8 | N: −12.4 |
|  |  | S: −13.9 | Q: 6.5 | H: 6.5 | A: 6.5 | S: −11.6 | D: −12.1 |
| 86 | ILE | K: −5.0 | T: 9.9 | T: 9.9 | D: 9.9 | E: −3.6 | K: −5.1 |
|  |  | E: −4.3 | D: 10.9 | D: 10.9 | A: 10.9 | K: −2.2 | E: −3.6 |
|  |  | Q: −4.0 | A: 11.6 | A: 11.6 | T: 11.6 | Q: −1.9 | Q: −2.1 |
| 88 | GLN | E: −0.1 |  |  |  |  |  |
|  |  | T: 1.6 |  |  |  |  |  |
|  |  | Q: 2.4 |  |  |  |  |  |
| 90 | LEU | K: −3.3 | E: 6.3 | E: 6.3 | E: 6.3 | E: −0.8 | E: −2.2 |
|  |  | E: −0.6 | D: 9.4 | T: 9.4 | T: 9.4 | Q: −0.7 | Q: −2.1 |
|  |  | Q: 0.5 | T: 9.5 | D: 9.5 | D: 9.5 | R: −0.6 | R: −0.1 |
| 93 | PHE | S: −18.0 | E: 0.3 | S: 0.3 | E: 0.3 | D: −15.3 | D: −15.1 |
|  |  | D: −17.4 | T: 2.3 | D: 2.3 | D: 2.3 | S: −15.1 | S: −14.8 |
|  |  | R: −17.4 | D: 3.0 | E: 3.0 | Q: 3.0 | N: −13.8 | N: −13.6 |
| 94 | ILE | K: −2.7 | E: 4.1 | T: 4.1 | H: 4.1 | E: −2.0 | K: −2.0 |
|  |  | E: −2.0 | D: 4.3 | N: 4.3 | D: 4.7 | Q: −.06 | E: −1.9 |
|  |  | Q: −0.8 | A: 4.7 | D: 4.7 | E: 5.9 | K: −0.4 | Q: −0.4 |
| 95 | ASN | Q: 3.4 |  | N: 5.9 |  | Q: −2.6 |  |
|  |  | D: 3.9 |  | D: 6.6 |  | N: 0.3 |  |
|  |  | S: 4.4 |  | Q: 7.3 |  | D: 0.4 |  |
| 97 | GLU | N: −5.8 |  | — |  | N: −3.6 |  |
|  |  | D: −4.9 |  |  |  | D: −2.6 |  |
|  |  | S: −4.1 |  |  |  | S: −2.6 |  |
| 98 | THR | D: −0.8 |  | N: −2.1 |  | Q: −9.3 |  |
|  |  | E: −0.7 |  | D: −1.4 |  | R: −8.3 |  |
|  |  | K: −0.3 |  | Q: −1.1 |  | E: −8.0 |  |
| 108 | GLN | N: −5.7 |  | Q: −2.6 |  | S: −6.8 |  |
|  |  | D: −5.2 |  | D: −0.7 |  | N: −5.8 |  |
|  |  | Q: −5.1 |  | S: 0.4 |  | D: −4.8 |  |
| 110 | ASN | E: 1.0 |  |  |  | A: −7.1 | Q: −8.1 |
|  |  | Q: 4.0 |  |  |  | E: −5.7 | E: −6.7 |
|  |  | S: 8.3 |  |  |  | D: −4.6 | A: −4.6 |
| 111 | ALA | A: 0.0 |  |  |  | A: −4.7 | A: −6.4 |
|  |  | S: 1.7 |  |  |  | S: −2.1 | S: −3.3 |
|  |  | H: 9.2 |  |  |  | T: 26.2 | D: 46.3 |
| 115 | LEU | K: −3.4 | K: −3.8 | E: −3.8 | K: −3.8 | E: 8.9 | E: 6.7 |
|  |  | E: −3.2 | E: −3.3 | K: −3.3 | E: −3.3 | T: 11.5 | A: 10.1 |
|  |  | D: −1.3 | D: −1.5 | D: −1.5 | D: −1.5 | D: 12.1 | Q: 10.4 |
| 116 | TYR | H: 4.5 | H: 4.6 | H: 4.6 | H: 4.6 | H: 1.7 | H: 1.5 |
|  |  | S: 6.0 | T: 8.8 | T: 8.8 | A: 8.8 | T: 4.3 | T: 4.6 |
|  |  | T: 7.5 | A: 9.3 | A: 9.3 | S: 9.3 | S: 6.4 | S: 6.7 |
| 117 | PHE | Q: −7.3 | K: −4.1 | R: −4.1 | R: −4.1 | K: 6.7 | H: 7.1 |
|  |  | R: −7.2 | Q: −3.9 | K: −3.9 | Q: −3.9 | E: 9.1 | K: 8.0 |
|  |  | E: −6.9 | R: −3.7 | Q: −3.7 | K: −3.7 | H: 10.3 | E: 8.1 |
| 119 | ASP | R: −2.5 |  | N: −0.4 |  | N: −5.2 |  |
|  |  | Q: −2.3 |  | S: 0.7 |  | S: −4.1 |  |
|  |  | N: −1.9 |  | D: 0.8 |  | D: −3.8 |  |
| 120 | SER | N: −5.8 |  | S: −1.7 |  | N: −7.4 |  |
|  |  | S: −4.6 |  | N: −1.6 |  | Q: −6.6 |  |
|  |  | D: −4.4 |  | D: −0.1 |  | S: −5.9 |  |
| 121 | SER | N: −4.7 |  | N: −4.8 |  | Q: −7.0 |  |
|  |  | Q: −4.0 |  | D: −3.4 |  | E: −6.2 |  |
|  |  | S: −3.7 |  | Q: −3.2 |  | K: −5.9 |  |
| 122 | ASN | R: −2.6 |  | N: 5.3 |  | Q: −6.0 | R: 0.0 |
|  |  | N: −2.5 |  | Q: 6.3 |  | E: −5.7 | Q: 0.6 |
|  |  | Q: −2.4 |  | D: 7.6 |  | R: −5.6 | N: 0.7 |
| 123 | VAL | Q: −5.4 | T: −9.2 | T: −9.2 | T: −9.2 | D: 4.8 | T: 4.8 |
|  |  | E: −4.5 | R: −8.6 | R: −8.6 | R: −8.6 | T: 5.1 | A: 6.0 |
|  |  | S: −4.1 | E: −8.3 | E: −8.3 | E: −8.3 | A: 6.4 | D: 7.6 |
| 125 | LEU | Q: −10.7 | Q: −9.0 | Q: −9.0 | Q: −9.0 | H: −1.0 | H: −0.6 |
|  |  | E: −9.8 | E: −8.4 | E: −8.4 | E: −8.4 | A: 3.8 | E: 3.2 |
|  |  | S: −9.3 | S: −7.3 | S: −7.3 | S: −7.3 | D: 3.8 | K: 3.2 |
| 126 | LYS | T: −1.2 | D: −10.8 | Q: −2.2 | D: −4.6 | Q: −9.9 | Q: −9.2 |
|  |  | D: 1.0 | S: −7.4 | R: −1.5 | E: −4.6 | E: −9.3 | E: −8.5 |
|  |  | E: 1.0 | N: −5.9 | D: −1.3 | K: −4.2 | R: −7.9 | R: −7.3 |
| 127 | LYS | Q: −13.7 | N: −17.3 | Q: −7.9 | N: −17.8 | D: −12.5 | T: −5.2 |
|  |  | E: −12.8 | D: −16.7 | E: −7.2 | D: −17.5 | T: −11.7 | S: −2.5 |
|  |  | R: −12.0 | Q: −13.7 | S: −5.9 | Q: −13.5 | S: −10.2 | D: −0.9 |
| 128 | TYR | K: 1.2 | E: 4.9 | H: 4.9 | H: 4.9 | E: 2.5 | E: 0.7 |
|  |  | E: 2.3 | A: 7.1 | D: 9.9 | K: 9.9 | D: 3.9 | D: 3.6 |
|  |  | Q: 4.1 | H: 9.9 | K: 10.5 | D: 10.5 | K: 5.9 | K: 5.2 |
| 129 | ARG | Q: −21.5 | D: −8.3 | D: −4.3 | D: −6.6 | N: −10.3 | E: −9.9 |
|  |  | E: −21.1 | E: −6.6 | S: −4.1 | S: −6.6 | D: −9.7 | N: −8.9 |
|  |  | N: −19.1 | N: −6.0 | Q: −2.9 | Q: −6.1 | E: −9.4 | Q: −8.3 |

TABLE 5-continued

Energies of most favorable alternate residues in each variable position in BMP-7

| # | Wt | dimer | ALK2 | ALK3 | ALK6 | ActRIIa | ActRIIb |
|---|---|---|---|---|---|---|---|
| 130 | ASN | E: −0.9 | D: −4.3 | D: −2.1 | D: −2.0 | | |
| | | Q: −0.7 | E: −3.5 | R: −1.7 | R: −1.7 | | |
| | | R: −0.4 | Q: −3.3 | E: −1.7 | Q: −0.9 | | |
| 134 | ARG | Q: −7.6 | Q: −6.7 | Q: −4.0 | S: −1.1 | R: −0.8 | R: −1.0 |
| | | E: −7.1 | E: −6.0 | D: −3.8 | D: −1.0 | S: 0.0 | S: 0.5 |
| | | R: −6.5 | R: −5.2 | S: −3.7 | Q: −1.0 | D: 1.3 | D: 1.7 |
| 135 | ALA | E: −3.4 | | | | | |
| | | D: −3.4 | | | | | |
| | | Q: −3.0 | | | | | |

Next, combinatorial calculations were performed in which multiple variable positions located close in space were allowed to vary. The most favorable amino acid sequence was first identified with DEE, and then Monte Carlo calculations were performed to identify 10,000 favorable energies. All residues that were selected for a given position in at least 500 of the top 10,000 sequences were noted, and the number of occurrences is given in the table below. For residues that are within 5 Å of at least one atom in the type I or type II receptor, calculations were also performed using templates consisting of the BMP-7 dimer bound to receptor.

TABLE 6

Preferred alternate residues identified using combinatorial PDA ® calculations

| # | wt | dimer | ALK2 | ALK3 | ALK6 | ActRII | ActRIIb |
|---|---|---|---|---|---|---|---|
| 36 | GLN | Q: 7809 | | M: 9996 | | Q: 10000 | |
| | | N: 1884 | | | | | |
| 39 | LYS | S: 9842 | S: 8163 | S: 9997 | D: 5917 | S: 10000 | S: 10000 |
| | | | D: 1118 | | M: 3085 | | |
| | | | | | T: 572 | | |
| 42 | GLU | D: 4594 | | D: 4405 | | L: 9999 | |
| | | N: 4513 | | F: 3105 | | | |
| | | L: 893 | | N: 2490 | | | |
| 48 | ARG | H: 9950 | R: 9994 | Q: 7431 | R: 10000 | E: 9274 | R: 6089 |
| | | | | E: 2530 | | Q: 649 | Q: 1849 |
| | | | | | | | N: 1072 |
| | | | | | | | K: 936 |
| 49 | ASP | S: 5123 | | R: 10000 | | N: 8591 | |
| | | N: 4554 | | | | M: 766 | |
| | | | | | | R: 589 | |
| 52 | TRP | W: 9937 | W: 10000 | W: 10000 | W: 10000 | W: 10000 | W: 10000 |
| 53 | GLN | Q: 5056 | D: 9292 | W: 6190 | D: 9673 | S: 9247 | R: 9596 |
| | | E: 4894 | Q: 695 | D: 3771 | | Q: 753 | |
| 54 | ASP | D: 9422 | | N: 7578 | | N: 9326 | |
| | | S: 578 | | D: 1217 | | S: 606 | |
| | | | | S: 1205 | | | |
| 55 | TRP | F: 9234 | W: 10000 | W: 10000 | W: 10000 | K: 7426 | Q: 4838 |
| | | | | | | Q: 2063 | K: 2656 |
| | | | | | | | N: 1596 |
| 57 | ILE | Q: 4803 | V: 7154 | V: 9029 | T: 6435 | I: 10000 | I: 10000 |
| | | E: 4362 | T: 1771 | E: 940 | V: 2518 | | |
| | | | | | Q: 928 | | |
| 60 | GLU | K: 4894 | Q: 6658 | R: 6190 | Q: 8619 | E: 10000 | E: 9727 |
| | | Q: 4752 | E: 1911 | Q: 3243 | E: 878 | | |
| | | | N: 1072 | | | | |
| 70 | GLU | E: 10000 | | M: 7656 | | E: 10000 | |
| | | | | E: 1051 | | | |
| | | | | T: 840 | | | |
| 73 | PHE | M: 9998 | F: 9569 | F: 10000 | F: 9968 | | |
| 76 | ASN | N: 7622 | A: 9496 | A: 10000 | A: 9309 | D: 8520 | D: 9528 |
| | | D: 2269 | S: 504 | | S: 658 | K: 1480 | |
| 77 | SER | N: 9226 | A: 9989 | D: 10000 | D: 10000 | N: 4869 | N: 5705 |
| | | | | | | S: 2426 | D: 2067 |
| | | | | | | D: 2247 | S: 1703 |
| 86 | ILE | L: 5322 | V: 3799 | I: 10000 | D: 4757 | | |
| | | F: 4678 | M: 2956 | | I: 3625 | | |
| | | | I: 2197 | | H: 737 | | |
| | | | D: 757 | | V: 548 | | |
| 90 | LEU | I: 7320 | L: 7909 | I: 10000 | L: 8453 | | |
| | | L: 1971 | I: 2091 | | I: 1547 | | |
| 93 | PHE | R: 10000 | M: 9971 | F: 10000 | F: 9422 | | |

TABLE 6-continued

Preferred alternate residues identified using combinatorial PDA ® calculations

| # | wt | dimer | ALK2 | ALK3 | ALK6 | ActRII | ActRIIb |
|---|---|---|---|---|---|---|---|
| 94 | ILE | K: 6521<br>I: 3472 | I: 10000 | I: 8908<br>V: 705 | I: 5328<br>V: 3624<br>H: 636 | | |
| 95 | ASN | N: 10000 | | N: 10000 | | E: 6756<br>M: 2423<br>R: 821 | |
| 97 | GLU | E: 8909<br>N: 565 | | | | R: 6746<br>W: 1317<br>F: 968<br>E: 681 | |
| 98 | THR | K: 9813 | | E: 9849 | | R: 8142<br>K: 1037<br>Q: 659 | |
| 108 | GLN | W: 10000 | | W: 5051<br>L: 4949 | | E: 8219<br>M: 1368 | |
| 115 | LEU | E: 9073 | E: 5297<br>K: 1647<br>D: 857<br>Q: 682<br>L: 611 | E: 9835 | E: 5464<br>K: 2112<br>D: 1598 | I: 9494<br>L: 506 | I: 8877<br>L: 865 |
| 116 | TYR | S: 7525<br>H: 1972 | T: 8380<br>S: 734 | Y: 10000 | Y: 10000 | Y: 9428 | Y: 6205<br>F: 3186<br>T: 577 |
| 117 | PHE | K: 10000 | R: 5996<br>S: 734 | K: 5592<br>Q: 2504<br>E: 1856 | K: 5038<br>E: 4955 | F: 10000 | F: 9956 |
| 119 | ASP | N: 3258<br>R: 2589<br>Q: 1910<br>D: 1614 | | N: 4613<br>D: 4434<br>S: 665 | | N: 9068<br>D: 842 | |
| 120 | SER | R: 9814 | | Q: 9548 | | E: 10000 | |
| 121 | SER | N: 8165<br>Q: 1581 | | N: 8910<br>Q: 791 | | W: 10000 | |
| 122 | ASN | Q: 9767 | | R: 7212<br>Q: 2768 | | Q: 10000 | |
| 123 | VAL | R: 4692<br>N: 4665 | Q: 3725<br>K: 3427<br>E: 2351 | R: 10000 | K: 4955<br>Q: 2595<br>E: 1252<br>R: 999 | V: 10000 | V: 9965 |
| 125 | LEU | Q: 2247<br>E: 2234<br>N: 2103<br>D: 1840 | Q: 2148<br>E: 2024<br>D: 1558<br>N: 925<br>R: 854<br>T: 681<br>S: 553 | Q: 2688<br>E: 2252<br>D: 1815<br>R: 1215<br>N: 828 | Q: 2618<br>E: 1838<br>T: 1591<br>D: 1522<br>R: 897 | L: 10000 | E: 7583<br>L: 1122<br>Q: 540 |
| 126 | LYS | E: 10000 | D: 10000 | E: 7981<br>Q: 2019 | E: 10000 | Q: 8882<br>E: 904 | Q: 7360<br>R: 2587 |
| 127 | LYS | Q: 10000 | Q: 7702<br>N: 2120 | Q: 10000 | Q: 7301<br>N: 1850<br>D: 849 | T: 8654<br>D: 1346 | Q: 10000 |
| 128 | TYR | K: 7798<br>M: 2139 | M: 10000 | M: 10000 | M: 10000 | W: 10000 | W: 10000 |
| 129 | ARG | D: 9142<br>N: 858 | E: 7628<br>D: 1971 | E: 10000 | E: 7301<br>R: 2699 | N: 8799<br>D: 1201 | N: 7847<br>Q: 1495<br>D: 541 |
| 134 | ARG | M: 6832<br>E: 3143 | E: 9900 | E: 10000 | E: 9997 | E: 9996 | Q: 5893<br>Y: 2281<br>E: 1787 |

PDA® technology calculations were also performed to identify mutations that are likely to either increase or substantially eliminate binding to the BMP inhibitor protein Noggin. At each position in BMP-7 that is within 5 Å of at least one atom in Noggin (see table above), energies were calculated for alternate residues using a template comprising (1) BMP-7 only, and (2) BMP-7 bound to Noggin. Preferred substitutions include, but are not limited to, those listed in the tables below.

TABLE 7

Preferred substitutions to substantially eliminate Noggin binding

| Residue number | Alternate amino acid | Energy (BMP-7 only) | Energy (BMP-7-noggin) | Δ(Energy) |
|---|---|---|---|---|
| 55 | ILE | 5.38 | 109.30 | 103.91 |
| 55 | LEU | 4.01 | 421.61 | 417.60 |
| 55 | LYS | 0.94 | 2576.09 | 2575.15 |
| 55 | ARG | -1.82 | 1012.10 | 1013.92 |
| 57 | MET | 4.30 | 219.47 | 215.17 |
| 57 | TYR | 7.74 | 42890.27 | 42882.53 |
| 57 | GLU | -3.05 | 119.37 | 122.42 |
| 57 | HIS | 6.53 | 2905.10 | 2898.57 |
| 57 | HSP | 5.72 | 3035.01 | 3029.29 |
| 57 | LYS | 0.40 | 114.98 | 114.58 |
| 57 | GLN | -4.66 | 150.57 | 155.23 |
| 57 | ARG | -3.67 | 4086.31 | 4089.97 |
| 58 | ILE | 9.42 | 322.50 | 313.09 |
| 58 | LEU | 9.30 | 84822.06 | 84812.76 |
| 58 | MET | 8.88 | 754.69 | 745.81 |
| 58 | TYR | 4.94 | 1105.51 | 1100.57 |
| 58 | VAL | 6.66 | 226.71 | 220.05 |
| 58 | GLU | -1.90 | 199.69 | 201.59 |
| 58 | HIS | 5.03 | 1385.50 | 1380.47 |
| 58 | HSP | 4.31 | 1951.88 | 1947.58 |
| 58 | LYS | 3.52 | 987.81 | 984.28 |
| 58 | GLN | -3.02 | 181.68 | 184.70 |
| 58 | ARG | -3.00 | 221.94 | 224.94 |
| 59 | TYR | 9.57 | 15040.62 | 15031.05 |
| 76 | GLU | 3.88 | 210.29 | 206.41 |
| 76 | GLN | 2.78 | 304.90 | 302.12 |
| 76 | ARG | 8.02 | 9204.62 | 9196.60 |
| 77 | GLU | 9.73 | 5019.33 | 5009.59 |
| 77 | GLN | 8.40 | 4804.74 | 4796.34 |
| 83 | PHE | 3.55 | 2730.52 | 2726.97 |
| 83 | TRP | 1.99 | 4103.04 | 4101.05 |
| 83 | TYR | -3.56 | 1606.78 | 1610.35 |
| 83 | HSP | -1.42 | 110.31 | 111.73 |
| 83 | LYS | 0.82 | 275.49 | 274.67 |
| 83 | ARG | -4.14 | 114.90 | 119.04 |
| 86 | LEU | 6.41 | 177.93 | 171.52 |
| 86 | MET | 3.76 | 182.42 | 178.66 |
| 86 | PHE | 4.06 | 510.92 | 506.87 |
| 86 | TYR | 0.29 | 486.51 | 486.22 |
| 86 | ARG | -1.29 | 360.80 | 362.09 |
| 87 | HIS | 4.35 | 722.22 | 717.87 |
| 87 | HSP | 9.18 | 650.44 | 641.27 |
| 113 | ILE | 9.08 | 220.54 | 211.47 |
| 113 | LEU | 4.06 | 1142.97 | 1138.91 |
| 113 | MET | 6.10 | 1203.71 | 1197.61 |
| 113 | PHE | 5.50 | ***** | |
| 113 | TYR | 5.35 | ***** | |
| 113 | GLU | -2.87 | 199.31 | 202.17 |
| 113 | HIS | -0.15 | 219.95 | 220.09 |
| 113 | HSP | 2.62 | 294.44 | 291.82 |
| 113 | LYS | 2.39 | 219.74 | 217.35 |
| 113 | GLN | -3.68 | 419.42 | 423.10 |
| 113 | ARG | -0.22 | 31582.79 | 31583.01 |
| 115 | MET | 0.59 | 433.33 | 432.74 |
| 115 | LYS | -4.58 | 104.47 | 109.05 |
| 115 | ARG | -2.89 | 629.82 | 632.71 |
| 123 | MET | 2.17 | 186.71 | 184.54 |
| 123 | TYR | 7.81 | ***** | |
| 123 | HIS | 6.31 | 2238.61 | 2232.29 |
| 123 | HSP | 5.63 | 11040.76 | 11035.13 |
| 127 | ILE | 7.26 | 270.14 | 262.88 |
| 127 | VAL | 5.22 | 223.61 | 218.39 |
| 127 | HIS | 8.31 | 1012.09 | 1003.79 |
| 127 | HSP | 8.00 | 1708.17 | 1700.17 |
| 128 | ILE | 0.25 | 401.32 | 401.07 |
| 128 | ARG | -3.86 | 124.31 | 128.17 |

TABLE 8

Preferred substitutions to increase Noggin binding affinity

| Residue number | Alternate amino acid | Energy (BMP-7 only) | Energy (BMP-7-noggin) | Δ(Energy) |
|---|---|---|---|---|
| 48 | MET | 8.38 | -3.60 | -11.99 |
| 57 | VAL | -3.57 | -14.50 | -10.92 |
| 59 | MET | 7.34 | -7.13 | -14.47 |
| 60 | ILE | 14.56 | -0.05 | -14.61 |
| 60 | LEU | 13.50 | 2.97 | -10.52 |
| 60 | MET | 15.34 | 2.70 | -12.64 |
| 60 | VAL | 13.08 | 0.51 | -12.58 |
| 74 | MET | 13.88 | 1.04 | -12.84 |
| 76 | ILE | 13.60 | -1.47 | -15.07 |
| 76 | VAL | 11.19 | -6.60 | -17.79 |
| 76 | ALA | 9.97 | -3.48 | -13.45 |
| 77 | ALA | 13.76 | -2.23 | -15.99 |
| 77 | HIS | 16.02 | 2.66 | -13.36 |
| 77 | THR | 12.53 | -7.56 | -20.09 |
| 86 | VAL | 4.41 | -10.60 | -15.02 |
| 113 | ALA | 2.89 | -7.70 | -10.58 |
| 119 | ILE | 28.27 | 18.21 | -10.06 |
| 119 | LEU | 29.23 | 17.25 | -11.99 |
| 124 | VAL | -4.30 | -14.52 | -10.22 |
| 125 | ILE | 247.94 | 228.79 | -19.16 |
| 125 | MET | 10.73 | -17.18 | -27.91 |
| 125 | ALA | 4.10 | -7.22 | -11.32 |
| 126 | MET | 8.64 | -9.57 | -18.21 |
| 126 | TRP | 64.98 | 35.09 | -29.89 |
| 126 | HIS | 49.02 | 38.84 | -10.18 |
| 126 | HSP | 47.75 | 37.16 | -10.59 |
| 126 | THR | 6.31 | -5.14 | -11.45 |
| 127 | MET | 7.52 | -11.44 | -18.95 |
| 127 | ALA | 3.79 | -6.37 | -10.16 |

A number of alternate residues were selected for each variable position. In all cases, the alternate residues are predicted to be compatible with the structure of BMP-7 dimer. The alternate residues are predicted to interact with the receptors in a diverse manner, encompassing competitive inhibitor variants, receptor specific variants, and high affinity variants. The table shown below indicates preferred substitutions that were identified using sequence alignment data, ACE calculations, and PDA® technology calculations. Note that "X" indicates a one-residue deletion.

TABLE 9

BMP-7 variants in Library 1.

| Residue | wt | calculation | Library 1.1 | Library 1.2 | Library 1.3 | # variants |
|---|---|---|---|---|---|---|
| 21 | LEU | expH | DKS | | | 3 |
| 23 | MET | expH | DKS | | | 3 |
| 26 | VAL | expH | DKS | | | 3 |
| 36 | GLN | adtl. surf | | | ENR | 3 |
| 39 | LYS | specificity | | DERST | | 5 |
| 42 | GLU | adtl. surf | | | DQRT | 4 |
| 44 | TYR | expH | AEHKQR | | | 6 |
| 48 | ARG | specificity | | EKNQ | | 4 |
| 49 | ASP | adtl. surf | | | ES | 2 |
| 52 | TRP | expH | AEKQ | | | 4 |
| 53 | GLN | specificity | | ADERS | H | 6 |
| 54 | ASP | adtl. surf | | | KNRS | 4 |
| 55 | TRP | expH | AEHKNQ | | R | 7 |
| 57 | ILE | expH | AEHKTV | D | | 7 |
| 60 | GLU | specificity | | KQRST | | 5 |
| 63 | ALA | adtl. surf | | | EQRS | 4 |
| 65 | TYR | electrostatic | | | DEN | 3 |
| 70 | GLU | adtl. surf | | | AQ | 2 |
| 73 | PHE | expH | AEHQRS | D | | 7 |
| 76 | ASN | specificity | | ADST | | 4 |

TABLE 9-continued

BMP-7 variants in Library 1.

| Residue | wt | calculation | Library 1.1 | Library 1.2 | Library 1.3 | # variants |
|---|---|---|---|---|---|---|
| 77 | SER | specificity | | | ADKQT | 5 |
| 78 | TYR | expH | DGHNST | | | 6 |
| 80 | ASN | glycosylation | DQST | | | 4 |
| 82 | THR | glycosylation | V | | | 1 |
| 83 | ASN | glycosylation | P | | | 1 |
| 86 | ILE | expH | EKQT | AD | | 6 |
| 88 | GLN | electrostatic | | | E | 1 |
| 90 | LEU | expH | EKNQRST | | | 7 |
| 93 | PHE | expH | ADEQRST | | | 7 |
| 94 | ILE | expH | AEKQRT | H | | 7 |
| 95 | ASN | adtl. surf | | | DKQR | 4 |
| 97 | GLU | adtl. surf | | | DKR | 3 |
| 98 | THR | adtl. surf | | | AEKRX | 5 |
| 108 | GLN | adtl. surf | | | DKS | 3 |
| 110 | ASN | electrostatic | | | DEH | 3 |
| 111 | ALA | electrostatic | | | DS | 2 |
| 115 | LEU | expH | EKT | | | 3 |
| 116 | TYR | expH | DEHKST | A | | 7 |
| 117 | PHE | expH | ADEKQR | H | | 7 |
| 119 | ASP | adtl. surf | | | ENST | 4 |
| 120 | SER | adtl. surf | | | DERN | 4 |
| 121 | SER | adtl. surf | | | DEKNT | 5 |
| 122 | ASN | adtl. surf | | | EQR | 3 |
| 123 | VAL | expH | ADNRT | | | 5 |
| 125 | LEU | expH | AEKQ | | Y | 5 |
| 126 | LYS | specificity | | DEQR | | 4 |
| 127 | LYS | specificity | | DQST | E | 5 |
| 128 | TYR | expH | DEHKQ | | | 5 |
| 129 | ARG | specificity | | DES | | 3 |
| 130 | ASN | electrostatic | | | D | 1 |
| 134 | ARG | specificity | | EKQS | D | 5 |
| 135 | ALA | electrostatic | | | DES | 3 |

As may easily be appreciated, many of these preferred substitutions may easily be incorporated into the analogous positions in other BMPs and TGF-β family members. A sequence alignment of human BMPs is given in FIG. 3 (SEQ ID NOS:7-12). In order to identify which substitutions may be incorporated into BMP-2, BMP-4, BMP-5, BMP-6, and BMP-8, the energy of each of the above substitutions was calculated in the context of each dimer structure. Substitutions with similar energies in two different structures are likely to produce similar effects in the two proteins.

TABLE 10

Energies of library mutations in the context of the BMP-2, 4, 5, 6, 7, and 8 structures.

| Residue | substitution | BMP2 E(tot) | BMP4 E(tot) | BMP5 E(tot) | BMP6 E(tot) | BMP-7 E(tot) | BMP8 E(tot) |
|---|---|---|---|---|---|---|---|
| Q 36 | GLU | 5.6 | 3.4 | 6.0 | 6.4 | 5.8 | 5.6 |
| Q 36 | ASN | 4.2 | 5.1 | 2.5 | 3.0 | 2.4 | 2.2 |
| Q 36 | ARG | 8.0 | 5.2 | 5.4 | 5.7 | 5.3 | 5.0 |
| A 37 | ASP | −3.0 | −3.1 | −0.2 | 1.7 | −0.3 | −3.4 |
| A 37 | GLU | −1.8 | −2.4 | 5.0 | 3.5 | 2.9 | 1.3 |
| A 37 | HIS | 2.3 | 2.5 | 10.6 | 7.1 | 8.5 | 5.1 |
| A 37 | LYS | 2.5 | 2.7 | 2.9 | 1.1 | 2.7 | −0.8 |
| A 37 | ARG | 1.0 | 1.1 | 4.2 | 2.8 | 4.1 | 4.7 |
| K 39 | ASP | 1.7 | 1.7 | 3.6 | 1.7 | 2.2 | 3.9 |
| K 39 | GLU | 0.7 | 0.6 | −0.7 | −2.7 | −0.4 | 0.9 |
| K 39 | ARG | 2.5 | 2.5 | 1.8 | 0.0 | 3.2 | 2.1 |
| K 39 | SER | −0.2 | −0.3 | 2.0 | 0.0 | 1.8 | 2.9 |
| K 39 | THR | −0.7 | −0.7 | 1.2 | 1.2 | 2.3 | 1.6 |
| E 42 | ASP | 4.2 | 1.3 | 2.7 | 3.4 | 2.7 | 2.5 |
| E 42 | GLN | 1.3 | 0.0 | −0.8 | 1.4 | −0.7 | 0.0 |
| E 42 | ARG | 1.9 | 1.3 | 2.2 | 4.6 | 1.9 | 1.5 |
| E 42 | THR | 4.4 | 3.3 | 4.2 | 5.0 | 4.1 | 3.7 |
| Y 44 | ALA | 2.6 | 2.0 | 7.3 | 7.3 | 7.3 | 8.3 |
| Y 44 | GLU | −3.5 | −4.1 | −0.2 | −0.2 | −0.1 | 1.3 |
| Y 44 | HIS | −2.4 | −2.6 | 3.0 | 2.9 | 3.0 | 3.9 |
| Y 44 | LYS | −2.6 | −2.9 | 3.3 | 3.4 | 3.2 | 5.5 |
| Y 44 | GLN | −4.4 | −4.9 | −1.1 | −1.1 | −1.0 | 0.4 |
| Y 44 | ARG | −2.8 | −2.9 | 2.6 | 2.7 | 2.6 | 4.5 |
| R 48 | GLU | 2.0 | 2.0 | −1.5 | −1.7 | −1.5 | 1.2 |
| R 48 | LYS | 7.0 | 7.0 | 2.2 | 2.9 | 2.2 | 7.0 |
| R 48 | ASN | −0.6 | −0.6 | −0.1 | −0.1 | 0.1 | −1.7 |
| R 48 | GLN | 0.3 | 0.4 | −0.4 | −0.4 | −0.4 | −0.2 |
| D 49 | GLU | 4.3 | 4.3 | 2.2 | 2.2 | 2.1 | 1.8 |
| D 49 | SER | 4.3 | 4.3 | −0.7 | −0.7 | −0.9 | −1.0 |
| W 52 | ALA | −4.1 | −4.0 | 2.7 | 2.7 | 2.4 | 2.1 |
| W 52 | GLU | −6.4 | −6.4 | −2.3 | −2.3 | −2.5 | −3.4 |
| W 52 | LYS | −5.1 | −5.0 | −2.6 | −2.6 | −2.8 | −5.0 |
| W 52 | GLN | −5.2 | −5.0 | −3.5 | −3.5 | −3.7 | −4.8 |
| Q 53 | ALA | 2.0 | 1.9 | 0.1 | −1.4 | 0.1 | −3.9 |
| Q 53 | ASP | −1.2 | −1.2 | −0.3 | −2.0 | −0.3 | −5.3 |
| Q 53 | GLU | 0.3 | 0.3 | 9.1 | −1.5 | 9.1 | −6.8 |
| Q 53 | HIS | 2.8 | 2.8 | 1.4 | 0.5 | 1.4 | 1.6 |
| Q 53 | ARG | −1.6 | −1.5 | 3.5 | 0.7 | 3.3 | −3.6 |
| Q 53 | SER | 0.2 | 0.2 | 0.2 | −1.8 | 0.2 | −3.4 |
| D 54 | LYS | 12.3 | 12.4 | 4.3 | 4.4 | 5.5 | 6.0 |
| D 54 | ASN | 4.5 | 4.4 | −1.9 | −1.9 | 0.1 | −1.6 |
| D 54 | ARG | 8.6 | 8.7 | −0.3 | −0.3 | 1.6 | 1.2 |
| D 54 | SER | 6.1 | 6.1 | −0.2 | −0.2 | −0.3 | 0.1 |
| W 55 | ALA | 1.9 | 2.0 | 1.9 | 1.9 | 1.8 | 2.2 |
| W 55 | GLU | −2.5 | −2.4 | −1.8 | −1.8 | −1.8 | −1.7 |
| W 55 | HIS | 0.6 | 1.4 | 4.0 | 4.0 | 3.7 | 4.4 |
| W 55 | LYS | 0.2 | 0.3 | 2.7 | 2.7 | 2.6 | 3.0 |
| W 55 | ASN | −4.0 | −3.9 | −3.9 | −3.9 | −3.9 | −3.6 |
| W 55 | GLN | −3.7 | −3.7 | −2.7 | −2.7 | −2.8 | −2.5 |
| W 55 | ARG | −5.0 | −4.8 | −3.6 | −3.6 | −3.7 | −3.2 |
| I 57 | VAL | −3.9 | −3.6 | −2.7 | −3.9 | −2.8 | −2.2 |
| I 57 | ALA | 1.1 | 1.5 | −0.5 | −1.3 | −0.6 | −0.7 |
| I 57 | ASP | −2.8 | −2.7 | −4.2 | −5.3 | −4.2 | −4.3 |
| I 57 | GLU | −4.8 | −4.5 | −6.2 | −7.1 | −6.1 | −5.4 |
| I 57 | HIS | 2.7 | 2.9 | 4.2 | 2.8 | 4.3 | 3.5 |
| I 57 | LYS | −1.0 | −0.9 | −5.8 | −6.5 | −6.1 | −2.0 |
| I 57 | THR | −7.3 | −7.1 | −1.2 | −2.0 | −1.2 | −0.7 |
| E 60 | LYS | 5.3 | 5.1 | 5.9 | 6.1 | 5.4 | 6.1 |
| E 60 | GLN | 0.3 | 0.2 | 2.8 | 2.5 | 0.7 | 1.3 |
| E 60 | ARG | 2.0 | 1.9 | 3.6 | 3.7 | 1.3 | 5.1 |
| E 60 | SER | 2.2 | 2.1 | 3.5 | 2.7 | 2.9 | 3.2 |
| E 60 | THR | 3.2 | 3.1 | 5.2 | 5.1 | 2.7 | 5.7 |
| A 63 | GLU | −2.0 | −2.0 | −0.9 | −0.6 | −2.2 | −4.5 |
| A 63 | GLN | −2.7 | −2.7 | −1.7 | −1.5 | −3.1 | −4.7 |
| A 63 | ARG | −2.3 | −2.3 | −1.0 | −0.3 | −3.4 | −1.4 |
| A 63 | SER | −0.4 | −0.4 | 0.5 | 1.1 | 1.4 | 1.4 |
| Y 65 | ASP | −4.1 | −6.0 | −3.4 | −3.5 | −3.4 | −3.7 |
| Y 65 | GLU | 21.7 | 19.5 | −3.7 | −3.8 | −3.9 | 73.9 |
| Y 65 | ASN | −0.7 | −2.4 | −0.3 | −0.3 | −0.4 | −0.7 |
| E 70 | ALA | 4.3 | 2.2 | 2.6 | 4.6 | 2.6 | 1.9 |
| E 70 | GLN | −0.7 | −0.9 | 0.4 | 1.1 | −0.3 | −0.3 |
| A 72 | ASP | 10.7 | −1.8 | −1.3 | −1.3 | −1.1 | −1.7 |
| A 72 | GLU | −0.1 | −3.6 | −1.3 | −1.2 | −3.1 | −1.5 |
| A 72 | HIS | 3.7 | −0.6 | 2.9 | 2.9 | 2.4 | 2.6 |
| A 72 | LYS | 1.9 | −2.4 | 1.1 | 1.1 | 0.5 | 0.8 |
| A 72 | ASN | 9.0 | −0.3 | 2.3 | 2.3 | 2.4 | 1.9 |
| A 72 | ARG | −4.4 | −2.2 | −2.9 | −2.9 | −3.1 | −3.1 |
| A 72 | SER | 2.0 | −1.0 | −4.3 | −4.3 | −4.4 | −4.6 |
| F 73 | ALA | 0.2 | 0.3 | 4.0 | 4.0 | 6.0 | 4.0 |
| F 73 | ASP | −1.9 | −1.8 | 3.4 | 3.4 | 4.0 | 3.6 |
| F 73 | GLU | −3.2 | −3.0 | 1.1 | 1.1 | 1.2 | 1.3 |
| F 73 | HIS | −0.7 | −0.6 | 3.7 | 3.7 | 5.6 | 2.7 |
| F 73 | GLN | −4.0 | −3.9 | 0.3 | 0.3 | 0.6 | 0.6 |
| F 73 | ARG | −4.7 | −4.5 | −1.2 | −1.2 | −0.8 | −1.0 |
| F 73 | SER | −1.2 | −1.1 | 1.8 | 1.8 | 1.2 | 1.8 |
| N 76 | ALA | 4.1 | 4.0 | 6.2 | 6.2 | 5.9 | 4.8 |
| N 76 | ASP | −0.3 | −0.3 | 1.1 | 1.1 | 0.9 | 0.1 |
| N 76 | SER | 0.4 | 0.4 | 2.5 | 2.5 | 2.3 | 1.1 |

TABLE 10-continued

Energies of library mutations in the context of the BMP-2, 4, 5, 6, 7, and 8 structures.

| Residue | substitution | BMP2 E(tot) | BMP4 E(tot) | BMP5 E(tot) | BMP6 E(tot) | BMP-7 E(tot) | BMP8 E(tot) |
|---|---|---|---|---|---|---|---|
| N 76 | THR | 8.2 | 7.8 | 5.9 | 5.9 | 5.4 | 4.0 |
| S 77 | ALA | 13.7 | 13.7 | 15.1 | 15.1 | 15.1 | 14.7 |
| S 77 | ASP | 6.3 | 6.4 | 7.8 | 7.8 | 7.9 | 7.5 |
| S 77 | LYS | 18.2 | 18.2 | 19.4 | 19.4 | 19.3 | 18.8 |
| S 77 | GLN | 8.9 | 9.0 | 9.8 | 9.8 | 9.8 | 9.3 |
| S 77 | THR | 12.6 | 12.8 | 13.7 | 13.7 | 13.6 | 12.0 |
| Y 78 | ASP | 3.5 | 3.7 | 3.4 | 3.4 | 5.0 | 5.7 |
| Y 78 | HIS | 11.4 | 10.4 | 11.7 | 11.7 | 12.5 | 11.2 |
| Y 78 | ASN | 2.2 | 2.4 | 2.6 | 2.6 | 4.0 | 4.8 |
| Y 78 | SER | 4.2 | 4.3 | 4.5 | 4.5 | 5.7 | 6.3 |
| Y 78 | THR | 8.1 | 8.2 | 8.2 | 8.2 | 9.3 | 9.1 |
| I 86 | ALA | 1.0 | 0.9 | 0.2 | 0.2 | −0.1 | −0.4 |
| I 86 | ASP | −1.1 | −1.4 | −4.8 | −4.8 | −4.9 | −5.5 |
| I 86 | GLU | −4.2 | −4.1 | −6.5 | −6.5 | −6.5 | −6.6 |
| I 86 | LYS | −0.8 | −0.8 | −7.0 | −7.0 | −7.2 | −7.7 |
| I 86 | GLN | −2.7 | −2.4 | −6.2 | −6.2 | −6.3 | −6.6 |
| I 86 | THR | 2.2 | 2.3 | −1.0 | −1.0 | −1.1 | −1.4 |
| Q 88 | GLU | −11.9 | −9.9 | −10.8 | −10.8 | −10.9 | −9.9 |
| L 90 | GLU | −7.9 | −7.8 | −6.4 | −6.4 | −7.1 | −8.4 |
| L 90 | LYS | −4.4 | −4.2 | −7.0 | −6.9 | −9.8 | −8.5 |
| L 90 | ASN | −1.7 | −1.6 | −3.6 | −3.6 | −2.1 | −1.7 |
| L 90 | GLN | −6.0 | −5.9 | −5.4 | −5.4 | −6.0 | −7.0 |
| L 90 | ARG | −1.4 | −1.2 | −4.7 | −4.7 | −5.6 | −5.5 |
| L 90 | SER | −5.4 | −5.4 | −2.4 | −2.4 | −2.6 | −2.7 |
| L 90 | THR | −4.0 | −3.9 | −1.5 | −1.5 | −2.6 | −3.8 |
| F 93 | ALA | 1.9 | 2.1 | 1.3 | 1.3 | 1.2 | 1.2 |
| F 93 | ASP | −2.1 | −2.0 | −2.9 | −2.8 | −3.0 | −3.2 |
| F 93 | GLU | −4.5 | −4.4 | 0.7 | 0.8 | 0.4 | 0.2 |
| F 93 | GLN | −4.9 | −4.8 | −0.6 | −0.6 | −0.9 | −1.1 |
| F 93 | ARG | −3.4 | −3.2 | −2.6 | −2.6 | −3.0 | −2.9 |
| F 93 | SER | −2.9 | −2.8 | −3.7 | −3.7 | −3.6 | −3.6 |
| F 93 | THR | 3.9 | 4.0 | 6.7 | 6.7 | 6.3 | 6.2 |
| I 94 | ALA | 1.8 | 1.9 | −1.9 | 0.5 | 0.6 | −2.4 |
| I 94 | GLU | −4.9 | −4.8 | −7.6 | −5.2 | −5.0 | −7.8 |
| I 94 | HIS | −1.7 | −1.6 | 6.1 | −0.2 | 2.9 | 5.8 |
| I 94 | LYS | −5.0 | −5.0 | −8.4 | −5.2 | −5.7 | −8.4 |
| I 94 | GLN | −3.7 | −3.6 | −6.1 | −4.0 | −3.8 | −6.2 |
| I 94 | ARG | −0.4 | −0.2 | −5.9 | −3.4 | −3.5 | −4.2 |
| I 94 | THR | 0.4 | 0.4 | −1.7 | 0.5 | 1.0 | −1.1 |
| N 95 | ASP | 0.8 | 2.8 | −4.1 | 2986.4 | −1.7 | −2.1 |
| N 95 | LYS | 3.8 | 9.2 | −1.2 | 4982.8 | 3.9 | 2.7 |
| N 95 | GLN | 0.6 | 3.4 | −4.9 | 3497.0 | −2.2 | 0.0 |
| N 95 | ARG | 2.6 | 6.3 | −2.5 | 4116.5 | 3.7 | 2.4 |
| E 97 | ASP | 3.2 | 3.6 | 6.6 | 3.3 | 3.5 | 6.1 |
| E 97 | LYS | 3.7 | 3.9 | 15.6 | 12.9 | 13.1 | 15.9 |
| E 97 | ARG | 4.3 | 4.2 | 11.4 | 8.0 | 8.2 | 11.1 |
| T 98 | ALA | 8.5 | 8.2 | 0.4 | −0.4 | −0.4 | −0.6 |
| T 98 | GLU | 4.3 | 5.6 | −5.5 | −3.7 | −2.8 | −4.3 |
| T 98 | LYS | 9.5 | 11.1 | −5.8 | −3.4 | −2.4 | −2.2 |
| T 98 | ARG | 6.0 | 7.9 | 0.6 | 3.1 | 3.5 | 3.1 |
| A 105 | VAL | −11.4 | −14.8 | −4.2 | −4.2 | 0.4 | −4.2 |
| Q 108 | ASP | −1.6 | −1.6 | −3.3 | −3.4 | −3.3 | −2.2 |
| Q 108 | LYS | 4.4 | 4.4 | 2.8 | 3.0 | 2.8 | 3.3 |
| Q 108 | SER | −0.6 | −0.7 | −2.6 | −2.6 | −2.6 | −1.3 |
| N 110 | ASP | −0.9 | −0.7 | 7.5 | 7.5 | 12.8 | −0.5 |
| N 110 | GLU | −0.6 | −0.5 | −1.6 | −1.7 | −1.4 | 0.0 |
| N 110 | HIS | 10.3 | 10.8 | 11.8 | 11.8 | 12.4 | 8.9 |
| A 111 | ASP | 266.0 | 263.9 | 1199.6 | 1199.6 | 1155.7 | 1201.4 |
| A 111 | SER | 2.5 | 2.5 | 1.4 | 1.4 | 1.4 | 3.4 |
| L 115 | GLU | −7.9 | −7.9 | −7.8 | −7.9 | −7.7 | −7.8 |
| L 115 | LYS | −7.2 | −7.2 | −7.6 | −7.5 | −7.8 | −7.5 |
| L 115 | THR | −1.3 | −2.6 | −5.4 | −5.4 | −5.4 | −5.4 |
| Y 116 | ASP | 22.1 | 24.7 | 275.0 | 274.9 | 278.8 | 274.6 |
| Y 116 | GLU | 76.1 | 65.5 | 125.3 | 125.2 | 126.5 | 122.8 |
| Y 116 | HIS | −9.2 | −9.5 | −7.5 | −7.5 | −7.1 | −6.7 |
| Y 116 | LYS | 4301.8 | 3766.9 | 198.7 | 198.7 | 211.7 | 203.6 |
| Y 116 | SER | −2.3 | −2.3 | −5.6 | −5.6 | −5.6 | −4.3 |
| Y 116 | THR | −4.8 | −4.8 | −4.2 | −4.3 | −4.1 | −2.5 |
| F 117 | ALA | −3.5 | −2.5 | −0.1 | −0.1 | −2.0 | −2.7 |
| F 117 | ASP | −5.1 | −4.7 | −2.4 | −2.5 | −2.2 | −4.7 |
| F 117 | GLU | −7.2 | −7.1 | −4.6 | −4.7 | −4.4 | −6.8 |
| F 117 | LYS | −6.4 | −7.6 | −2.9 | −2.8 | −2.7 | −5.5 |
| F 117 | GLN | −8.1 | −8.0 | −4.7 | −4.7 | −4.8 | −8.0 |
| F 117 | ARG | −6.5 | −5.8 | −4.8 | −4.7 | −4.7 | −5.8 |
| D 119 | GLU | 10.2 | 12.8 | 6.8 | 5.6 | 6.9 | 6.7 |
| D 119 | ASN | 4.5 | 7.3 | 6.0 | 4.9 | 6.1 | 6.0 |
| D 119 | SER | 6.5 | 9.3 | 8.0 | 6.9 | 8.0 | 7.9 |
| D 119 | THR | 12.2 | 14.3 | 10.4 | 10.3 | 10.5 | 10.4 |
| S 120 | ASP | 1.9 | 1.8 | 1.5 | 1.5 | 1.6 | 1.0 |
| S 120 | GLU | 1.1 | 1.0 | 3.5 | 3.5 | 3.6 | 2.9 |
| S 120 | ASN | 0.5 | 0.3 | 0.1 | 0.1 | 0.2 | 0.0 |
| S 120 | ARG | 1.6 | 1.4 | 5.3 | 5.3 | 5.4 | 5.0 |
| S 121 | ASP | 3.2 | 3.4 | 3.2 | 3.2 | 3.2 | 2.5 |
| S 121 | GLU | 4.2 | 4.4 | 3.9 | 3.8 | 3.9 | 3.2 |
| S 121 | LYS | 9.7 | 9.8 | 7.9 | 8.0 | 7.8 | 8.1 |
| S 121 | ASN | 1.8 | 1.9 | 1.7 | 1.7 | 1.7 | 1.1 |
| S 121 | THR | 8.2 | 8.4 | 6.5 | 6.5 | 6.4 | 5.7 |
| N 122 | GLU | −0.3 | −0.1 | −1.0 | −1.1 | 2.9 | −1.1 |
| N 122 | GLN | −2.0 | −1.8 | −2.6 | −2.6 | 1.4 | −2.6 |
| N 122 | ARG | −0.8 | −0.5 | −2.6 | −2.9 | 1.2 | −2.6 |
| V 123 | ALA | 0.7 | 0.9 | 1.9 | 1.9 | 1.7 | 1.7 |
| V 123 | ASP | −1.8 | −1.8 | −1.0 | −1.1 | −0.8 | −1.2 |
| V 123 | ASN | −2.9 | −2.8 | 0.1 | 0.1 | 0.3 | 0.0 |
| V 123 | ARG | −3.3 | −2.9 | −2.7 | −2.6 | −2.4 | −3.0 |
| V 123 | THR | −2.6 | −2.3 | −2.2 | −2.2 | −2.4 | −3.2 |
| L 125 | ALA | 5.0 | 5.2 | 4.7 | 4.7 | 4.5 | 4.7 |
| L 125 | GLU | −0.8 | −0.8 | −1.2 | −1.3 | −1.3 | −1.2 |
| L 125 | LYS | 4.2 | 4.2 | 3.6 | 3.7 | 3.4 | 3.7 |
| L 125 | GLN | −1.8 | −1.7 | −2.2 | −2.2 | −2.3 | −2.2 |
| K 126 | ASP | −1.6 | −3.4 | −5.5 | −5.5 | −5.5 | −5.2 |
| K 126 | GLU | −1.4 | −3.0 | −3.3 | −3.4 | −5.4 | −2.7 |
| K 126 | GLN | −2.4 | −4.3 | −1.4 | −1.4 | −3.6 | −3.3 |
| K 126 | ARG | −2.7 | −5.7 | 0.5 | 0.5 | −0.7 | 9.9 |
| K 127 | ASP | 5.9 | 4.0 | 0.7 | 0.7 | 0.6 | 0.9 |
| K 127 | GLN | 2.0 | 0.2 | −2.5 | −2.5 | −3.1 | −2.3 |
| K 127 | SER | 3.0 | 1.2 | 0.1 | 0.1 | −0.1 | 0.1 |
| K 127 | THR | 5.6 | 3.7 | 1.5 | 1.5 | −0.5 | 1.7 |
| Y 128 | ASP | −6.4 | −6.6 | −5.5 | −5.5 | −5.6 | −5.3 |
| Y 128 | GLU | −3.3 | −3.0 | −7.4 | −7.5 | −7.6 | −8.9 |
| Y 128 | HIS | −10.0 | −9.8 | −4.3 | −4.3 | −4.4 | −7.3 |
| Y 128 | LYS | 8.1 | 10.0 | −8.7 | −8.6 | −8.8 | −5.9 |
| Y 128 | GLN | 3.6 | 3.6 | −5.7 | −5.7 | −5.8 | −4.6 |
| R 129 | ASP | −0.5 | −0.5 | 0.1 | 0.0 | 0.1 | 0.1 |
| R 129 | GLU | −0.3 | 1.6 | −2.0 | −2.0 | −2.0 | −1.9 |
| R 129 | SER | −0.4 | 1.5 | 1.5 | 1.5 | 1.5 | 1.5 |
| N 130 | ASP | −6.6 | −4.6 | −2.8 | −2.8 | −2.6 | −2.7 |
| R 134 | GLU | −6.9 | −6.9 | −7.1 | −7.1 | −6.9 | −6.9 |
| R 134 | LYS | 12.3 | 18.6 | −4.3 | −4.1 | −2.2 | −4.1 |
| R 134 | GLN | −4.3 | −4.2 | −7.5 | −7.4 | −7.4 | −6.6 |
| R 134 | SER | −2.4 | −2.4 | −3.8 | −3.8 | −3.9 | −3.2 |
| A 135 | ASP | 1.6 | 1.2 | −5.1 | −5.1 | −5.9 | −1.7 |
| A 135 | GLU | 2.2 | 1.2 | −4.8 | −4.8 | −5.9 | −2.6 |
| A 135 | SER | 3.7 | 2.4 | −4.0 | −4.0 | −5.2 | −2.1 |
| H 139 | ARG | −4.4 | −4.4 | −0.6 | −0.6 | −2.6 | −0.6 |

Correlation coefficients ($R^2$) for energies calculated using the BMP-2 template versus other BMP templates are as follows: BMP2 vs BMP4=0.93, BMP2 vs BMP5=0.52, BMP2 vs BMP6=0.44, BMP2 vs BMP-7=0.64, and BMP2 vs BMP8=0.52. Correlation coefficients ($R^2$) for energies calculated using the BMP-7 template versus other BMP templates are as follows: BMP-7 vs BMP2=0.54, BMP-7 vs BMP4=0.54, BMP-7 vs BMP5=0.95, BMP-7 vs. BMP6=0.71, and BMP-7 vs BMP8=0.76. These trends correlate with the sequence similarity of the pair. Modifications to BMP-7 have substantially similar effects on other BMPs if the energy difference between the modification in the BMP-7 template and another BMP template are less than 1 kcal/mol, or if both energies are higher than 50 kcal/mol. The following BMP-7 modifications have substantially similar effects in BMP-2: Q36E, A37K, K39D, E42R, E42T, R48N, R48Q, Q53D, Q53S, W55A, W55E, W55N, W55Q, E60K, E60Q, E60R, E60S, E60T, A63E, A63Q, Y65D, Y65N, E70Q, S77Q, S77T, Q88E, L90E, L90N, L90Q, F93A, F93D, F93R, F93S, I94E, I94K, I94Q, I94T, N95K, E97D, N110E, A111D, L115E, L115K, Y116D, Y116E, Y116K, Y116T, S120D, S120N, S121D, S121E, S121N, V123A, V123D, V123R, V123T, L125A, L125E, L125K, L125Q, Y128D, R129D, and R134E. The following BMP-7 modifications have substantially similar effects in BMP-4: Q36R, A37K, K39D, K39E, E42Q, E42R, E42T, R48N, R48Q, Q53D, Q53S, W55A, W55E, W55N, W55Q, I57V, E60K, E60Q, E60R, E60S, E60T, A63E, A63Q, E70A, E70Q, A72D, A72E, A72R, S77Q, S77T, Q88E, L90E, L90N, L90Q, F93A, F93D, F93R, F93S, I94E, I94K, I94Q, I94T, E97D, N110E, A111D, L115E, L115K, Y116D, Y116E, Y116K, Y116T, F117A, S120D, S120N, S121D, S121E, S121N, V123A, V123D, V123R, V123T, L125A, L125E, L125K, L125Q, K126Q, Y128D, R129D, R129S, and R134E. The following BMP-7 modifications have substantially similar effects in BMP-5: Q36E, Q36N, Q36R, A37D, A37K, A37R, K39E, K39S, E42D, E42Q, E42R, E42T, Y44A, Y44E, Y44H, Y44K, Y44Q, Y44R, R48E, R48K, R48N, R48Q, D49E, D49S, W52A, W52E, W52K, W52Q, Q53A, Q53E, Q53H, Q53R, Q53S, D54S, W55A, W55E, W55H, W55K, W55N, W55Q, W55R, I57V, I57A, I57D, I57E, I57H, I57K, I57T, E60K, E60S, A63S, Y65D, Y65E, Y65N, E70A, E70Q, A72D, A72H, A72K, A72N, A72R, A72S, F73D, F73E, F73Q, F73R, F73S, N76A, N76D, N76S, N76T, S77A, S77D, S77K, S77Q, S77T, Y78H, I86A, I86D, I86E, I86K, I86T, Q88E, L90E, L90Q, L90R, L90S, F93A, F93D, F93E, F93Q, F93R, F93S, F93T, T98A, Q108D, Q108K, Q108S, N110E, N110H, A111D, A111S, L115E, L115K, L115T, Y116D, Y116H, Y116K, Y116S, Y116T, F117D, F117E, F117K, F117Q, F117R, D119E, D119N, D119S, D119T, S120D, S120E, S120N, S120R, S121D, S121E, S121K, S121N, S121T, V123A, V123D, V123N, V123R, V123T, L125A, L125E, L125K, L125Q, K126D, K127D, K127Q, K127S, Y128D, Y128E, Y128H, Y128K, Y128Q, R129D, R129E, R129S, N130D, R134E, R134Q, R134S, and A135D. The following BMP-7 modifications have substantially similar effects in BMP-6: Q36E, Q36N, Q36R, A37E, K39D, E42D, E42T, Y44A, Y44E, Y44H, Y44K, Y44Q, Y44R, R48E, R48K, R48N, R48Q, D49E, D49S, W52A, W52E, W52K, W52Q, Q53H, D54S, W55A, W55E, W55H, W55K, W55N, W55Q, W55R, I57A, I57E, I57K, I57T, E60K, E60S, Y65D, Y65E, Y65N, A72D, A72H, A72K, A72N, A72R, A72S, F73D, F73E, F73Q, F73R, F73S, N76A, N76D, N76S, N76T, S77A, S77D, S77K, S77Q, S77T, Y78H, I86A, I86D, I86E, I86K, I86T, I86T, Q88E, L90E, L90Q, L90R, L90S, F93A, F93D, F93E, F93Q, F93R, F93S, F93T, I94A, I94E, I94K, I94Q, I94R, I94T, E97D, E97K, E97R, T98A, T98E, T98K, T98R, Q108D, Q108K, Q108S, N110E, N110H, A111D, A111S, L115E, L115K, L115T, Y116D, Y116E, Y116H, Y116K, Y116S, Y116T, F117D, F117E, F117K, F117Q, F117R, D119T, S120D, S120E, S120N, S120R, S121D, S121E, S121K, S121N, S121T, V123A, V123D, V123N, V123R, V123T, L125A, L125E, L125K, L125Q, K126D, K127D, K127Q, K127S, Y128D, Y128E, Y128H, Y128K, Y128Q, R129D, R129E, R129S, N130D, R134E, R134Q, R134S, and A135D. The following BMP-7 modifications have substantially similar effects in BMP-8: Q36E, Q36N, Q36R, A37R, K39T, E42D, E42Q, E42R, E42T, Y44A, Y44H, R48Q, D49E, D49S, W52A, W52E, Q53H, D54K, D54R, D54S, W55A, W55E, W55H, W55K, W55N, W55Q, W55R, I57V, I57A, I57D, I57E, I57H, I57T, E60K, E60Q, E60S, A63S, Y65D, Y65N, E70A, E70Q, A72D, A72H, A72K, A72N, A72R, A72S, F73D, F73E, F73Q, F73R, F73S, N76D, S77A, S77D, S77K, S77Q, Y78D, Y78N, Y78S, Y78T, I86A, I86D, I86E, I86K, I86T, I86T, Q88E, L90N, L90Q, L90R, L90S, F93A, F93D, F93E, F93Q, F93R, F93S, F93T, I94R, N95D, T98A, T98K, T98R, Q108K, A111D, L115E, L115K, L115T, Y116D, Y116E, Y116H, Y116K, F117A, D119E, D119N, D119S, D119T, S120D, S120E, S120N, S120R, S121D, S121E, S121K, S121N, S121T, V123A, V123D, V123N, V123R, V123T, L125A, L125E, L125K, L125Q, K126D, K126Q, K127D, K127Q, K127S, Y128D, R129D, R129E, R129S, N130D, R134E, R134Q, and R134S.

ACE calculations were also performed to assess the similarity of the structural environment at each variable position in BMP-7 vs. BMP-2, BMP-4, BMP-5, BMP-6, and BMP-8. At positions with an ACE similarity score of 0.4 or higher in the table below, mutations will have similar effects in BMP-7 vs. the other BMP. ACE similarity scores between 0.6 and 0.8 indicate that the effects of mutations are highly likely to have similar effects, and ACE similarity scores greater than 0.8 indicate that the effects of mutations should be substantially identical.

TABLE 11

ACE similarity scores for BMP-7 versus selected additional human TGF-β proteins

| | BMP-2 | BMP-3 | BMP-3B | BMP-4 | BMP-5 | BMP-6 | BMP-8 | BMP-9 | BMP-10 |
|---|---|---|---|---|---|---|---|---|---|
| 36 | 0.58 | 0.11 | 0.14 | 0.23 | 0.85 | 0.81 | 0.60 | 0.10 | 0.10 |
| 37 | 0.12 | 0.02 | 0.02 | 0.07 | 0.72 | 0.27 | 0.30 | 0.02 | 0.05 |
| 39 | 0.35 | 0.03 | 0.04 | 0.24 | 0.75 | 0.67 | 0.38 | 0.02 | 0.02 |
| 42 | 0.30 | 0.37 | 0.37 | 0.33 | 0.56 | 0.27 | 0.69 | 0.36 | 0.36 |
| 44 | 0.19 | 0.04 | 0.04 | 0.22 | 0.95 | 0.82 | 0.59 | 0.04 | 0.21 |
| 48 | 0.17 | 0.17 | 0.17 | 0.17 | 1.00 | 0.74 | 0.26 | 0.19 | 0.16 |
| 49 | 0.11 | 0.09 | 0.09 | 0.12 | 0.56 | 0.50 | 0.40 | 0.07 | 0.07 |
| 52 | 0.37 | 0.32 | 0.34 | 0.37 | 0.98 | 0.98 | 0.46 | 0.41 | 0.39 |
| 53 | 0.28 | 0.11 | 0.11 | 0.28 | 1.00 | 0.49 | 0.48 | 0.09 | 0.12 |
| 54 | 0.29 | 0.30 | 0.29 | 0.29 | 1.00 | 0.96 | 0.19 | 0.29 | 0.30 |
| 55 | 0.59 | 0.30 | 0.26 | 0.58 | 1.00 | 0.99 | 0.52 | 0.26 | 0.17 |
| 57 | 0.20 | 0.45 | 0.11 | 0.20 | 1.00 | 0.96 | 0.43 | 0.05 | 0.08 |
| 60 | 0.48 | 0.18 | 0.18 | 0.48 | 1.00 | 0.74 | 0.65 | 0.21 | 0.61 |
| 63 | 0.19 | 0.04 | 0.03 | 0.21 | 0.35 | 0.10 | 0.81 | 0.06 | 0.31 |
| 65 | 0.04 | 0.01 | 0.01 | 0.05 | 0.96 | 0.99 | 0.20 | 0.03 | 0.02 |
| 70 | 0.04 | 0.02 | 0.02 | 0.04 | 0.38 | 0.12 | 0.22 | 0.03 | 0.02 |
| 72 | 0.23 | 0.01 | 0.01 | 0.08 | 0.93 | 0.80 | 0.23 | 0.03 | 0.01 |

TABLE 11-continued

| | | | | | | | | | |
|---|---|---|---|---|---|---|---|---|---|
| 73 | 0.18 | 0.02 | 0.02 | 0.17 | 0.41 | 0.41 | 0.12 | 0.18 | 0.05 |
| 76 | 0.21 | 0.12 | 0.11 | 0.17 | 0.58 | 0.58 | 0.50 | 0.10 | 0.15 |
| 77 | 0.26 | 0.12 | 0.12 | 0.26 | 0.76 | 0.76 | 0.37 | 0.12 | 0.16 |
| 78 | 0.34 | 0.13 | 0.13 | 0.28 | 0.77 | 0.75 | 0.61 | 0.14 | 0.17 |
| 80 | 0.09 | 0.01 | 0.01 | 0.09 | 0.32 | 0.46 | 0.37 | 0.04 | 0.07 |
| 82 | 0.02 | 0.01 | 0.01 | 0.01 | 0.99 | 0.99 | 0.68 | 0.00 | 0.00 |
| 83 | 0.41 | 0.14 | 0.14 | 0.36 | 1.00 | 1.00 | 0.44 | 0.26 | 0.25 |
| 86 | 0.36 | 0.09 | 0.09 | 0.36 | 0.97 | 0.97 | 0.39 | 0.10 | 0.04 |
| 88 | 0.04 | 0.15 | 0.15 | 0.04 | 0.82 | 0.82 | 0.05 | 0.01 | 0.00 |
| 90 | 0.18 | 0.11 | 0.11 | 0.18 | 0.33 | 0.33 | 0.18 | 0.11 | 0.04 |
| 93 | 0.37 | 0.39 | 0.39 | 0.38 | 0.59 | 0.63 | 0.54 | 0.32 | 0.14 |
| 94 | 0.11 | 0.07 | 0.07 | 0.12 | 0.18 | 0.34 | 0.22 | 0.15 | 0.16 |
| 95 | 0.00 | 0.01 | 0.01 | 0.00 | 0.05 | 0.11 | 0.05 | 0.02 | 0.00 |
| 97 | 0.02 | 0.05 | 0.05 | 0.02 | 0.06 | 0.59 | 0.15 | 0.06 | 0.02 |
| 98 | 0.20 | 0.02 | 0.02 | 0.20 | 0.05 | 0.88 | 0.11 | 0.02 | 0.07 |
| 105 | 0.03 | 0.01 | 0.01 | 0.03 | 0.95 | 0.98 | 0.69 | 0.03 | 0.03 |
| 108 | 0.09 | 0.03 | 0.02 | 0.09 | 0.37 | 0.98 | 0.45 | 0.05 | 0.04 |
| 110 | 0.11 | 0.03 | 0.01 | 0.10 | 0.69 | 0.70 | 0.30 | 0.01 | 0.02 |
| 111 | 0.02 | 0.00 | 0.00 | 0.01 | 1.00 | 1.00 | 0.23 | 0.00 | 0.03 |
| 115 | 0.45 | 0.39 | 0.30 | 0.45 | 1.00 | 0.99 | 0.82 | 0.08 | 0.07 |
| 116 | 0.38 | 0.65 | 0.55 | 0.38 | 1.00 | 0.98 | 0.38 | 0.09 | 0.04 |
| 117 | 0.36 | 0.43 | 0.37 | 0.35 | 1.00 | 0.98 | 0.61 | 0.20 | 0.14 |
| 119 | 0.53 | 0.58 | 0.54 | 0.37 | 1.00 | 0.69 | 0.89 | 0.38 | 0.41 |
| 120 | 0.07 | 0.37 | 0.32 | 0.07 | 1.00 | 1.00 | 0.33 | 0.04 | 0.01 |
| 121 | 0.13 | 0.62 | 0.25 | 0.10 | 1.00 | 0.72 | 0.53 | 0.05 | 0.07 |
| 122 | 0.21 | 0.22 | 0.18 | 0.09 | 1.00 | 0.42 | 0.62 | 0.08 | 0.07 |
| 123 | 0.16 | 0.64 | 0.21 | 0.15 | 1.00 | 0.99 | 0.52 | 0.07 | 0.09 |
| 125 | 0.69 | 0.62 | 0.27 | 0.69 | 1.00 | 1.00 | 0.84 | 0.50 | 0.43 |
| 126 | 0.60 | 0.33 | 0.29 | 0.60 | 1.00 | 1.00 | 0.28 | 0.46 | 0.38 |
| 127 | 0.37 | 0.07 | 0.03 | 0.37 | 1.00 | 1.00 | 0.61 | 0.04 | 0.03 |
| 128 | 0.55 | 0.38 | 0.38 | 0.55 | 1.00 | 1.00 | 0.30 | 0.07 | 0.05 |
| 129 | 0.10 | 0.05 | 0.06 | 0.09 | 0.99 | 0.99 | 0.61 | 0.01 | 0.03 |
| 130 | 0.26 | 0.02 | 0.03 | 0.26 | 0.98 | 0.98 | 0.77 | 0.06 | 0.07 |
| 134 | 0.07 | 0.05 | 0.12 | 0.07 | 0.36 | 0.38 | 0.12 | 0.04 | 0.03 |
| 135 | 0.10 | 0.00 | 0.00 | 0.10 | 0.23 | 0.22 | 0.10 | 0.04 | 0.03 |
| 139 | 0.19 | 0.01 | 0.00 | 0.18 | 0.94 | 0.97 | 0.80 | 0.10 | 0.10 |

| | BMP-15 | GDF-1 | GDF-3 | GDF-5 | GDF-8 | GDF-9 | TGF-$\beta$1 | TGF-$\beta$2 | TGF-$\beta$3 | TGF-$\beta$4 |
|---|---|---|---|---|---|---|---|---|---|---|
| 36 | 0.14 | 0.42 | 0.41 | 0.10 | 0.36 | 0.24 | 0.10 | 0.10 | 0.10 | 0.09 |
| 37 | 0.02 | 0.02 | 0.03 | 0.03 | 0.01 | 0.02 | 0.01 | 0.01 | 0.01 | 0.01 |
| 39 | 0.19 | 0.07 | 0.23 | 0.04 | 0.06 | 0.19 | 0.02 | 0.02 | 0.03 | 0.02 |
| 42 | 0.11 | 0.11 | 0.15 | 0.21 | 0.11 | 0.09 | 0.09 | 0.09 | 0.09 | 0.34 |
| 44 | 0.03 | 0.29 | 0.19 | 0.04 | 0.03 | 0.03 | 0.18 | 0.17 | 0.17 | 0.12 |
| 48 | 0.24 | 0.28 | 0.21 | 0.15 | 0.16 | 0.22 | 0.21 | 0.21 | 0.21 | 0.15 |
| 49 | 0.40 | 0.27 | 0.20 | 0.12 | 0.06 | 0.12 | 0.09 | 0.15 | 0.14 | 0.06 |
| 52 | 0.62 | 0.26 | 0.49 | 0.42 | 0.08 | 0.15 | 0.36 | 0.37 | 0.34 | 0.01 |
| 53 | 0.18 | 0.14 | 0.17 | 0.45 | 0.03 | 0.01 | 0.07 | 0.04 | 0.06 | 0.01 |
| 54 | 0.30 | 0.31 | 0.30 | 0.30 | 0.30 | 0.09 | 0.39 | 0.38 | 0.38 | 0.12 |
| 55 | 0.10 | 0.14 | 0.16 | 0.45 | 0.08 | 0.11 | 0.07 | 0.07 | 0.07 | 0.12 |
| 57 | 0.12 | 0.73 | 0.10 | 0.17 | 0.62 | 0.11 | 0.01 | 0.03 | 0.03 | 0.00 |
| 60 | 0.32 | 0.90 | 0.72 | 0.27 | 0.20 | 0.22 | 0.51 | 0.41 | 0.50 | 0.31 |
| 63 | 0.00 | 0.03 | 0.02 | 0.06 | 0.01 | 0.00 | 0.05 | 0.04 | 0.04 | 0.18 |
| 65 | 0.01 | 0.02 | 0.05 | 0.03 | 0.02 | 0.01 | 0.02 | 0.01 | 0.01 | 0.02 |
| 70 | 0.02 | 0.05 | 0.01 | 0.01 | 0.01 | 0.02 | 0.01 | 0.01 | 0.01 | 0.00 |
| 72 | 0.00 | 0.00 | 0.02 | 0.00 | 0.00 | 0.00 | 0.00 | 0.00 | 0.00 | 0.00 |
| 73 | 0.02 | 0.04 | 0.02 | 0.12 | 0.00 | 0.01 | 0.00 | 0.00 | 0.00 | 0.00 |
| 76 | 0.01 | 0.05 | 0.02 | 0.25 | 0.01 | 0.01 | 0.00 | 0.00 | 0.00 | 0.05 |
| 77 | 0.22 | 0.11 | 0.24 | 0.20 | 0.07 | 0.13 | 0.11 | 0.11 | 0.11 | 0.14 |
| 78 | 0.23 | 0.11 | 0.24 | 0.21 | 0.08 | 0.10 | 0.08 | 0.12 | 0.10 | 0.14 |
| 80 | 0.00 | 0.01 | 0.04 | 0.11 | 0.03 | 0.00 | 0.00 | 0.00 | 0.00 | 0.01 |
| 82 | 0.00 | 0.01 | 0.00 | 0.01 | 0.00 | 0.00 | 0.00 | 0.00 | 0.00 | 0.00 |
| 83 | 0.13 | 0.10 | 0.08 | 0.26 | 0.01 | 0.08 | 0.02 | 0.02 | 0.03 | 0.01 |
| 86 | 0.09 | 0.04 | 0.11 | 0.21 | 0.00 | 0.01 | 0.00 | 0.00 | 0.00 | 0.00 |
| 88 | 0.07 | 0.02 | 0.00 | 0.01 | 0.00 | 0.04 | 0.00 | 0.00 | 0.00 | 0.00 |
| 90 | 0.05 | 0.02 | 0.10 | 0.09 | 0.01 | 0.01 | 0.02 | 0.06 | 0.04 | 0.00 |
| 93 | 0.14 | 0.22 | 0.62 | 0.40 | 0.34 | 0.06 | 0.15 | 0.43 | 0.30 | 0.07 |
| 94 | 0.07 | 0.07 | 0.11 | 0.09 | 0.12 | 0.04 | 0.08 | 0.10 | 0.10 | 0.01 |
| 95 | 0.01 | 0.02 | 0.01 | 0.14 | 0.02 | 0.01 | 0.01 | 0.11 | 0.09 | 0.01 |
| 97 | 0.01 | 0.08 | 0.18 | 0.15 | 0.50 | 0.01 | 0.43 | 0.44 | 0.44 | 0.01 |
| 98 | 0.01 | 0.01 | 0.05 | 0.03 | 0.11 | 0.01 | 0.03 | 0.06 | 0.05 | 0.00 |
| 105 | 0.00 | 0.02 | 0.00 | 0.03 | 0.02 | 0.00 | 0.00 | 0.00 | 0.00 | 0.00 |
| 108 | 0.02 | 0.02 | 0.05 | 0.10 | 0.03 | 0.01 | 0.05 | 0.03 | 0.04 | 0.03 |
| 110 | 0.03 | 0.03 | 0.03 | 0.05 | 0.02 | 0.02 | 0.14 | 0.06 | 0.08 | 0.01 |
| 111 | 0.01 | 0.01 | 0.01 | 0.01 | 0.01 | 0.01 | 0.00 | 0.00 | 0.00 | 0.00 |
| 115 | 0.15 | 0.73 | 0.55 | 0.23 | 0.22 | 0.09 | 0.00 | 0.00 | 0.00 | 0.01 |
| 116 | 0.22 | 0.42 | 0.31 | 0.46 | 0.07 | 0.10 | 0.01 | 0.01 | 0.01 | 0.01 |
| 117 | 0.23 | 0.43 | 0.51 | 0.51 | 0.29 | 0.16 | 0.01 | 0.01 | 0.01 | 0.04 |

TABLE 11-continued

| | | | | | | | | | |
|---|---|---|---|---|---|---|---|---|---|
| 119 | 0.34 | 0.84 | 0.57 | 0.58 | 0.29 | 0.29 | 0.16 | 0.19 | 0.17 | 0.21 |
| 120 | 0.02 | 0.33 | 0.32 | 0.31 | 0.01 | 0.02 | 0.00 | 0.00 | 0.00 | 0.01 |
| 121 | 0.09 | 0.83 | 0.16 | 0.24 | 0.17 | 0.08 | 0.04 | 0.04 | 0.04 | 0.05 |
| 122 | 0.04 | 0.52 | 0.21 | 0.21 | 0.03 | 0.02 | 0.00 | 0.00 | 0.00 | 0.01 |
| 123 | 0.11 | 0.67 | 0.17 | 0.21 | 0.43 | 0.06 | 0.01 | 0.03 | 0.03 | 0.00 |
| 125 | 0.62 | 0.67 | 0.65 | 0.71 | 0.32 | 0.47 | 0.05 | 0.14 | 0.14 | 0.01 |
| 126 | 0.15 | 0.39 | 0.61 | 0.31 | 0.07 | 0.08 | 0.03 | 0.03 | 0.03 | 0.01 |
| 127 | 0.05 | 0.05 | 0.05 | 0.05 | 0.01 | 0.04 | 0.01 | 0.02 | 0.01 | 0.01 |
| 128 | 0.45 | 0.25 | 0.20 | 0.49 | 0.03 | 0.15 | 0.05 | 0.06 | 0.06 | 0.02 |
| 129 | 0.01 | 0.02 | 0.01 | 0.02 | 0.02 | 0.01 | 0.03 | 0.03 | 0.03 | 0.01 |
| 130 | 0.01 | 0.03 | 0.04 | 0.14 | 0.01 | 0.00 | 0.01 | 0.01 | 0.01 | 0.00 |
| 134 | 0.01 | 0.03 | 0.04 | 0.07 | 0.04 | 0.02 | 0.02 | 0.02 | 0.02 | 0.01 |
| 135 | 0.00 | 0.00 | 0.05 | 0.03 | 0.02 | 0.00 | 0.00 | 0.00 | 0.00 | 0.01 |
| 139 | 0.00 | 0.01 | 0.03 | 0.11 | 0.02 | 0.00 | 0.00 | 0.00 | 0.00 | 0.00 |

Based on the above ACE analysis, BMP-7 variants at the following positions are transferable to BMP-2: 36, 55, 60, 83, 115, 119, 125, 126, and 128. BMP-7 variants at the following positions are transferable to BMP-3: 57, 116, 117, 119, 121, 123, and 125. BMP-7 variants at the following positions are transferable to BMP-3b: 116 and 119. BMP-7 variants at the following positions are transferable to BMP-4: 55, 60, 115, 125, 126, and 128. BMP-7 variants at the following positions are transferable to BMP-5: 36, 37, 39, 42, 44, 48, 49, 52, 53, 54, 55, 57, 60, 65, 72, 73, 76, 77, 78, 82, 83, 86, 88, 93, 105, 110, 111, 115, 116, 117, 119, 120, 121, 122, 123, 125, 126, 127, 128, 129, 130, and 139. BMP-7 variants at the following positions are transferable to BMP-6: 36, 39, 44, 48, 49, 52, 53, 54, 55, 57, 60, 65, 72, 73, 76, 77, 78, 80, 82, 83, 86, 88, 93, 97, 98, 105, 108, 110, 111, 115, 116, 117, 119, 120, 121, 122, 123, 125, 126, 127, 128, 129, 130, and 139. BMP-7 variants at the following positions are transferable to BMP-9: 36, 42, 44, 49, 52, 53, 55, 57, 60, 63, 75, 78, 82, 83, 93, 105, 108, 115, 117, 119, 121, 122, 123, 125, 127, 129, 130, and 139. BMP-7 variants at the following positions are transferable to BMP-9: 52, 125, and 126. BMP-7 variants at the following positions are transferable to BMP-10: 60, 119, and 125. BMP-7 variants at the following positions are transferable to BMP-15: 49, 52, 125, and 128. BMP-7 variants at the following positions are transferable to GDF-1: 36, 57, 60, 115, 116, 117, 119, 121, 123, and 125. BMP-7 variants at the following positions are transferable to GDF-3: 36, 52, 60, 93, 115, 117, 119, 125, and 126. BMP-7 variants at the following positions are transferable to GDF-5: 52, 53, 55, 93, 116, 117, 119, 125, and 128. BMP-7 variants at the following positions are transferable to GDF-8: 57, 97, and 123. BMP-7 variants at the following positions are transferable to GDF-9: 125. BMP-7 variants at the following positions are transferable to TGF-β1: 60 and 97. BMP-7 variants at the following positions are transferable to TGF-β2: 60, 93 and 97. BMP-7 variants at the following positions are transferable to TGF-β3: 60 and 97.

Example 6

Generation of DNA Encoding the Parent BMP-7

A number of constructs for the expression of wild type human BMP-7 were made and tested: (1) native BMP-7 Image clone in pSport6 vector (obtained from ATCC), (2) FLAG-tagged BMP-7, with G4S linker and FLAG tag located just after the RXXR (SEQ ID NO:87) cleavage site in pCM-VTnT vector (Promega), (3) FLAG-tagged BMP-7 with a perfect Kozak sequence (MAV rather than MHV) in pCM-VTnT vector, (4) FLAG-tagged BMP-7 using native BMP-2 Kozak sequence, signal sequence, and pro-domain in pCM-VTnT vector, (5) FLAG-tagged BMP-7 using native MIC-1 Kozak sequence, signal sequence, and pro-domain in pCM-VTnT vector, and (6) native BMP-7 Image clone in pSport6 vector (obtained from ATCC) with 6× His tag at the N-terminus of the pro-domain. The untagged native Image clone in the pSport6 vector was found to produce the highest expression yields and was used as the template for variant construction.

Additional constructs were prepared for yeast expression: (1) pYES vector negative control, (2) BMP-7 mature domain in pYES vector, (3) E-BMP-7 mature domain in pYES vector, (4) AEAE-BMP-7 mature domain in pYES vector, (5) full length BMP-7 in pYES vector, and (6) REKR-full length BMP-7 in pYES vector.

Example 7

Generation of DNA Encoding BMP Variants

Constructs for the BMP-7 variants shown in the above table were prepared by site directed mutagenesis. The pSport6 Image clone (ATCC) was used as a template for all of the variants. DNA corresponding to each desired construct was prepared using Qiagen Miniprep or Maxiprep kits. As some of the BMP-7 variants were constructed using degenerate oligos, variants in addition to those explicitly included in Library 1 above were generated. Such variants include the following: L21E, L21G, L21N, L21R, M23G, M23N, M23R, V26E, V26G, V26N, K39A, K39G, K39N, Y44D, Y44G, Y44N, Y44P, Y44S, Y44T, R48D, R48H, W52P, W52T, Q53G, Q53K, Q53T, W55P, W55T, I57L, I57P, I57Q, E60H, E60N, E60P, F73G, F73K, F73N, F73T, N76Y, S77E, S77H, S77N, S77P, Y78P, Y78R, I86P, L90G, L90H, L90P, F93G, F93H, F93P, L115A, L115Q, Y116A, Y116Q, F117S, F117Y, V123G, I125P, I125T, K126G, K127A, K127H, K127N, K127P, K127Y, R129K, R129N, R134L, and R134P. Furthermore, silent mutations (that is, changes in DNA codon sequence that do not change the corresponding amino acid sequence) were introduced at I57, N76, Y116, V123, and R134.

Example 8

In Vitro Translation of Wild Type BMP-7

The following constructs were generated and used for in vitro translation experiments: (1) full length BMP-7 with FLAG tag at N-terminus of mature domain, (2) full length MIC-1 with FLAG tag at the N-terminus of the mature domain, (3) BMP-7 pro-domain with N-terminal FLAG tag, (4) MIC-1 pro-domain with N-terminal FLAG tag, (5)

BMP-7 mature domain with N-terminal FLAG tag, (6) MIC-1 mature domain with N-terminal FLAG tag, (7) full length BMP-7 with C-terminal FLAG tag, (8) full length MIC-1 with C-terminal FLAG tag, (9) BMP-7 pro-domain with C-terminal FLAG tag, (10) MIC-1 pro-domain with C-terminal FLAG tag, (11) BMP-7 mature domain with C-terminal FLAG tag, and (12) MIC-1 mature domain with C-terminal FLAG tag. The 5' end of each construct had a spacer, T7 promoter, globin UTR, and optimized ribosomal binding site preceeding the gene. Luciferase was used as a positive control. A coupled transcription/translation off the PCR product was used (TnT, Promega). Protein expression comparable to luciferase was obtained for all of the BMP-7 constructs other than (11) above.

Example 9

Expression of Wild Type and Variant BMP-7

The following small-scale expression protocol was used for initial library screening. 293T cells were plated into 6-well dishes (1-5×10$^5$ cells/mL in 4 mL DMEM 10% FBS). The next day, the cells were transfected using 5 ug DNA/well. As an internal control for transformation efficiency, several mini-preps of the native Image clone were used. After three days, the conditioned media was harvested and screened. Expression yields were determined using ELISA (all variants, not corrected for changes in antibody binding affinity, using R&D Systems ELISA Duoset Cat#DY354) and Western blotting (selected variants).

TABLE 12

Expression yields of Library 1 variants in 293T cells

| Variant name | ELISA concentration (ng/mL) | Fold change relative to Image clone | Western blot band intensity |
|---|---|---|---|
| L21D | 999 | 1.34 | |
| L21E | 332 | 0.45 | |
| L21G | 4917 | 0.78 | ++ |
| L21K | 495 | 0.50 | |
| L21N | 414 | 2.97 | − |
| L21R | 682 | 0.92 | |
| M23D | 565 | 0.56 | + |
| M23G | 4 | 0.03 | +++ |
| M23N | 600 | 0.81 | + |
| M23R | 3 | 0.02 | − |
| M23S | 15 | 0.11 | − |
| V26D | 747 | 0.75 | + |
| V26E | 1021 | 1.37 | + |
| V26G | 605 | 0.81 | − |
| V26K | 0 | 0.00 | − |
| V26N | 976 | 1.31 | + |
| V26S | 6 | 0.01 | − |
| Q36E | 7107 | 1.13 | ++ |
| Q36N | 1 | 0.00 | − |
| K39A | 22724 | 3.61 | + |
| K39D | 19 | 0.01 | |
| K39E | 1 | 0.00 | |
| K39G | 1 | 0.00 | |
| K39N | 69 | 0.04 | |
| K39R | 8376 | 1.33 | +++ |
| K39S | 23063 | 3.67 | + |
| K39T | 19 | 0.01 | |
| E42D | 7307 | 1.16 | +++ |
| E42Q | 6702 | 1.07 | +++ |
| E42R | 583 | 0.58 | − |
| E42T | 449 | 0.45 | − |
| Y44A | 259 | 0.04 | − |
| Y44D | 1 | 0.00 | |
| Y44E | 42 | 0.04 | − |
| Y44G | 0 | 0.00 | |
| Y44H | 1 | 0.01 | |
| Y44K | 2 | 0.00 | − |
| Y44N | 14 | 0.10 | − |
| Y44P | 0 | 0.00 | |
| Y44Q | 19 | 0.02 | − |
| Y44S | 1 | 0.00 | − |
| Y44T | 21 | 0.15 | |
| R48D | 1 | 0.00 | |
| R48E | 74 | 0.04 | |
| R48H | 6063 | 0.96 | − |
| R48N | 7100 | 1.13 | − |
| R48Q | 743 | 0.42 | |
| D49S | 24 | 0.02 | − |
| W52A | 38 | 0.27 | |
| W52E | 1 | 0.00 | |
| W52K | 0 | 0.00 | |
| W52P | 407 | 0.55 | |
| W52Q | 6 | 0.01 | − |
| W52T | 5 | 0.03 | |
| Q53A | 251 | 0.04 | − |
| Q53D | 6876 | 3.87 | ++ |
| Q53E | 1237 | 0.70 | |
| Q53G | 83 | 0.05 | + |
| Q53H | 645 | 0.29 | ++ |
| Q53K | 6413 | 1.02 | + |
| Q53R | 149 | 0.08 | |
| Q53S | 8530 | 1.36 | +++ |
| Q53T | 13237 | 2.10 | ++ |
| D54K | 10 | 0.01 | − |
| D54N | 458 | 0.46 | |
| D54S | 38 | 0.01 | − |
| W55A | 26 | 0.04 | |
| W55E | 2 | 0.00 | |
| W55H | 6 | 0.01 | |
| W55K | 10 | 0.07 | |
| W55N | 11 | 0.08 | |
| W55P | 0 | 0.00 | |
| W55Q | 10 | 0.07 | |
| W55R | 48 | 0.34 | − |
| W55T | 0 | 0.00 | |
| I57A | 47 | 0.01 | − |
| I57D | 0 | 0.00 | |
| I57E | 0 | 0.00 | |
| I57H | 8 | 0.06 | |
| I57I | 526 | 0.71 | − |
| I57K | 9 | 0.06 | |
| I57L | 16106 | 2.56 | 0.63 |
| I57P | 0 | 0.00 | |
| I57Q | 0 | 0.00 | |
| I57T | 1 | 0.00 | − |
| I57V | 6 | 0.01 | |
| E60H | 129 | 0.07 | |
| E60K | 755 | 0.76 | ++ |
| E60N | 5 | 0.00 | |
| E60P | 145 | 0.08 | |
| E60Q | 3172 | 3.17 | + |
| E60R | 2069 | 0.33 | + |
| E60S | 97 | 0.05 | |
| E60T | 410 | 0.41 | − |
| A63E | 4068 | 4.07 | + |
| A63Q | 8577 | 8.58 | ++ |
| A63R | 3183 | 3.18 | + |
| A63S | 8448 | 8.45 | ++ |
| Y65D | 18743 | 18.74 | +++ |
| Y65E | 382 | 0.38 | − |
| Y65N | 11678 | 11.68 | ++ |
| E70A | 501 | 0.50 | − |

TABLE 12-continued

Expression yields of Library 1 variants in 293T cells

| Variant name | ELISA concentration (ng/mL) | Fold change relative to Image clone | Western blot band intensity |
|---|---|---|---|
| E70Q | 679 | 0.68 | − |
| A72D | 5462 | 5.46 | + |
| A72E | 3822 | 3.82 | − |
| A72H | 3308 | 3.31 | + |
| A72K | 3863 | 3.86 | + |
| A72N | 1927 | 0.88 | + |
| A72R | 491 | 0.49 | − |
| A72S | 4784 | 2.17 | ++ |
| F73A | 153 | 1.10 | |
| F73D | 27 | 0.19 | |
| F73E | 138 | 0.99 | |
| F73G | 173 | 1.24 | |
| F73H | 5783 | 5.78 | ++ |
| F73K | 25 | 0.18 | |
| F73N | 321 | 0.43 | |
| F73Q | 75 | 0.54 | |
| F73S | 5159 | 0.82 | ++ |
| F73T | 193 | 1.38 | − |
| N76A | 5570 | 3.14 | |
| N76D | 7534 | 4.24 | |
| N76S | 8816 | 4.97 | |
| N76T | 4576 | 2.58 | |
| N76Y | 814 | 0.46 | |
| S77A | 1194 | 0.67 | |
| S77D | 1 | 0.00 | |
| S77E | 46 | 0.03 | |
| S77H | 49 | 0.03 | |
| S77K | 1 | 0.00 | |
| S77N | 1 | 0.00 | |
| S77P | 1302 | 0.73 | |
| S77Q | 645 | 0.64 | − |
| S77T | 1048 | 0.59 | |
| Y78D | 517 | 3.71 | − |
| Y78G | 2 | 0.00 | |
| Y78H | 10102 | 1.61 | + |
| Y78N | 5795 | 5.80 | − |
| Y78P | 1249 | 1.68 | |
| Y78R | 264 | 1.89 | − |
| Y78S | 9648 | 1.53 | ++ |
| Y78T | 714 | 5.12 | − |
| I86A | 5635 | 5.64 | ++ |
| I86D | 3480 | 3.48 | ++ |
| I86E | 2556 | 3.43 | |
| I86K | 2214 | 2.97 | |
| I86P | 5 | 0.01 | |
| I86Q | 3008 | 4.04 | |
| I86T | 532 | 0.53 | + |
| Q88E | 47 | 0.05 | − |
| L90E | 235 | 0.32 | |
| L90H | 62 | 0.08 | |
| L90H | 62 | 0.08 | |
| L90K | 3 | 0.00 | + |
| L90N | 200 | 0.09 | +++ |
| L90P | 109 | 0.15 | |
| L90R | 356 | 0.48 | |
| L90S | 5463 | 0.87 | +++ |
| L90T | 647 | 0.87 | |
| F93A | 12 | 0.02 | |
| F93D | 2346 | 0.37 | ++ |
| F93E | 646 | 0.87 | ++ |
| F93G | 24 | 0.03 | ++ |
| F93H | 16307 | 2.59 | +++ |
| F93P | 15 | 0.01 | +++ |
| F93Q | 279 | 0.13 | +++ |
| F93R | 38 | 0.02 | ++ |
| F93S | 2836 | 1.29 | ++ |
| F93T | 287 | 0.39 | + |
| I94A | 2 | 0.00 | +++ |
| I94E | 1 | 0.00 | − |
| I94H | 70 | 0.03 | − |
| I94K | 0 | 0.00 | − |
| I94P | 0 | 0.00 | |
| I94Q | 854 | 1.15 | |
| I94R | 0 | 0.00 | + |
| I94T | 10 | 0.01 | − |
| N95D | 18 | 0.02 | − |
| N95K | 2 | 0.00 | − |
| N95Q | 53 | 0.05 | − |
| N95R | 1 | 0.00 | − |
| E97D | 4784 | 2.17 | − |
| E97K | 2936 | 1.33 | − |
| E97R | 2113 | 0.96 | − |
| T98A | 4208 | 1.91 | |
| T98E | 3064 | 1.39 | |
| T98K | 5464 | 2.48 | − |
| T98X | 927 | 0.93 | − |
| A105V | 440 | 0.44 | − |
| Q108D | 4052 | 1.84 | − |
| Q108K | 1 | 0.00 | − |
| Q108S | 3529 | 1.60 | − |
| N110D | 8591 | 3.91 | − |
| N110E | 3020 | 1.37 | − |
| N110H | 331 | 0.33 | − |
| A111D | 2317 | 0.37 | ++ |
| A111S | 4358 | 4.36 | − |
| L115A | 24 | 0.03 | |
| L115E | 1 | 0.00 | − |
| L115K | 1 | 0.00 | − |
| L115Q | 1 | 0.00 | − |
| L115T | 0 | 0.00 | |
| Y116A | 0 | 0.00 | |
| Y116D | 1 | 0.00 | − |
| Y116E | 0 | 0.00 | |
| Y116H | 16724 | 2.66 | + |
| Y116K | 0 | 0.00 | |
| Y116Q | 0 | 0.00 | |
| Y116S | 34 | 0.01 | − |
| Y116T | 2 | 0.00 | − |
| Y116Y | 1922 | 2.58 | |
| F117A | 2 | 0.00 | − |
| F117D | 0 | 0.00 | |
| F117E | 2407 | 0.38 | − |
| F117H | 18720 | 2.98 | ++ |
| F117K | 329 | 0.44 | |
| F117Q | 3730 | 0.59 | + |
| F117R | 604 | 0.81 | |
| F117S | 42 | 0.06 | |
| F117Y | 1682 | 2.26 | |
| D119E | 9669 | 1.54 | ++ |
| D119N | 2870 | 0.46 | − |
| D119S | 4824 | 0.77 | + |
| D119T | 2022 | 0.32 | − |
| S120D | 21370 | 3.40 | +++ |
| S120E | 9259 | 1.47 | ++ |
| S120N | 11035 | 1.75 | ++ |
| S120R | 10544 | 1.68 | ++ |
| S121D | 9202 | 1.46 | ++ |
| S121E | 6098 | 0.97 | + |
| S121K | 4793 | 0.76 | − |
| S121N | 5161 | 0.82 | − |
| S121T | 2204 | 0.35 | − |
| N122E | 1 | 0.00 | − |
| N122Q | 6 | 0.00 | − |
| N122R | 63 | 0.01 | − |
| V123A | 0 | 0.00 | |
| V123D | 1 | 0.00 | − |
| V123G | 305 | 0.41 | |
| V123N | 0 | 0.00 | |
| V123R | 1 | 0.00 | − |
| V123T | 1 | 0.00 | |

TABLE 12-continued

Expression yields of Library 1 variants in 293T cells

| Variant name | ELISA concentration (ng/mL) | Fold change relative to Image clone | Western blot band intensity |
|---|---|---|---|
| V123V | 6 | 0.01 | |
| L125A | 1 | 0.00 | |
| L125E | 0 | 0.00 | |
| L125K | 1 | 0.00 | − |
| L125P | 0 | 0.00 | |
| L125Q | 4 | 0.00 | − |
| L125T | 0 | 0.00 | |
| L125Y | 3306 | 0.53 | − |
| K126D | 4393 | 0.70 | − |
| K126E | 24 | 0.01 | |
| K126G | 55 | 0.03 | |
| K126Q | 145 | 0.08 | |
| K126R | 10478 | 1.67 | + |
| K127A | 1 | 0.00 | |
| K127D | 1 | 0.00 | |
| K127E | 3974 | 0.63 | ++ |
| K127H | 1 | 0.00 | |
| K127N | 1 | 0.00 | |
| K127P | 1 | 0.00 | |
| K127Q | 1 | 0.00 | |
| K127S | 1 | 0.00 | − |
| K127T | 3 | 0.00 | |
| K127Y | 1 | 0.00 | |
| Y128D | 8948 | 1.42 | ++ |
| Y128E | 0 | 0.00 | |
| Y128H | 10887 | 1.73 | ++ |
| Y128K | 452 | 0.25 | |
| Y128Q | 11415 | 1.81 | ++ |
| R129D | 3093 | 0.49 | + |
| R129E | 15209 | 2.42 | + |
| R129K | 411 | 0.23 | |
| R129N | 573 | 0.32 | + |
| R129S | 46 | 0.03 | |
| N130D | 18652 | 2.96 | + |
| R134D | 1998 | 0.32 | − |
| R134E | 21604 | 3.43 | ++ |
| R134K | 830 | 0.47 | |
| R134L | 9016 | 5.08 | + |
| R134P | 125 | 0.07 | |
| R134Q | 1 | 0.00 | − |
| R134S | 4314 | 2.43 | ++ |
| A135D | 5 | 0.00 | − |
| A135E | 28974 | 4.61 | ++ |
| A135S | 29539 | 4.70 | ++ |
| H139R | 27483 | 4.37 | +++ |

Preferred modifications include those modifications that increase the expression yield in 293T cells by at least 2-fold, including but not limited to L21N, K39A, K39S, Q53D, Q53T, I57L, E60Q, A63E, A63Q, A63R, A63S, Y65D, Y65N, A72D, A72E, A72H, A72K, A72S, F73H, N76A, N76D, N76S, N76T, Y78D, Y78N, Y78T, I86A, I86D, I86E, I86K, I86Q, F93H, E97D, T98K, N110D, A111S, Y116H, F117H, F117Y, S120D, R129D, N130D, R134E, R134L, R134S, A135E, A135S, and H139R. Especially preferred modifications include those modifications that increase the expression yield in 293T cells by at least 5-fold, including but not limited to A63Q, A63S, Y65D, Y65N, A72D, F73H, Y78N, Y78T, I86A, and R134L. Furthermore, a silent mutation at Y116 from codon TCA to codon TAT was observed to increase the expression yield in 293T cells by 2.6-fold.

Additional expression protocols were used for different scales (96-, 48-, 24-, 12-, or 6-well dishes as well as 10 cm or 15 cm plates), serum-free expression, and expression in alternate hosts (CHO and BRK-21).

Expression yields of selected Library 1 variants were determined for 293T, CHO, and BRK21 cells, as shown below. Expression of the wild type Image clone does vary between expression hosts. However, the relative expression yields for the different variants tend to be improved across hosts, indicating that a variant that improves expression yield in one host tends to improve expression yield in other hosts.

TABLE 13

Expression yields of selected Library 1 variants in different expression hosts

| Yield vs. Image in | Image clone | Variant 23: L21G | Variant 154: Q53T | Variant 249: Y65N | Variant 117: Y78H | Variant 80: F93H |
|---|---|---|---|---|---|---|
| 293T | 1 | 3.8 | 1.9 | 7.2 | 2.3 | 8.5 |
| CHO | 1 | 0.9 | 1.4 | 6.8 | 1.1 | 6.5 |
| BRK21 | 1 | 1.0 | 1.4 | 10.2 | 1.3 | 5.8 |

Relative expression yield was also tested as a function of DNA dose (5.0, 2.5, and 1.0 ug were tested) and was found to be dose-independent.

Example 10

Characterization of the Receptor Binding Affinity of the BMP-7 Library 1 Variants The affinity of human and variant BMP-7 for several BMP receptors (ActRIa, BMPRIb, ActRIIa, and BMPRII) was measured using an ELISA-like assay, described below. 96-well plates were coated with a capture antibody (R&D Systems BMP-7 ELISA Duoset DY354, part # 840971) by diluting the antibody to 2 μg/mL in PBS, applying 50 μL/well, and incubating overnight or over the weekend at 4° C., in a humidified chamber. Excess liquid was removed from each plate. The plates were blocked by adding 175 μL blocking solution (1% BSA and 5% sucrose in PBS) to each well and incubating 1-2 hours at room temperature in a humidified chamber. The plates were then washed using an automated plate washer. 50 μL of BMP-7 containing solution (for example, diluted conditioned media obtained from the BMP-7 expression protocol above, or purified recombinant human BMP-7 of a known concentration) was added to each well and incubated 1.5-2 hours at room temperature in a humidified chamber. The plates were then washed using an automated plate washer. 50 μL of 5 μg/mL BMP receptor-Fc fusion in PBS was added to each well and incubated 1.5 hours at room temperature in a humidified chamber. The plates were then washed using an automated plate washer. 50 μL of 1:10, 000 diluted anti-human IgG-HRP conjugate in secondary antibody dilution buffer (1% BSA in PBS, filtered through a 0.2 50 μm filter) was added to each well and incubated 30 minutes at room temperature in a humidified chamber. The plates were then washed using an automated plate washer. 50 μL of pre-mixed TMB substrate (BD Pharmingen # 555214) was added to each well and incubated for 10-20 minutes at room temperature in the dark. 25 μL of 2N $H_2SO_4$ was added to each well. Absorbance readings at 450 nm were taken using a 540 nm wavelength correction.

The table below shows the receptor binding affinity of a selection of BMP-7 variants relative to the wild type protein (normalized to 1.0). Note that the assays were performed using a fixed volume of conditioned media rather than a specific concentration of protein, so differences in expression levels as well as differences in receptor binding affinity may affect the results. Data is shown only for variants with expression yields greater than 10.0 ng/mL.

TABLE 14

Receptor binding affinity of BMP-7 Library 1 variants.

| wt | res# | variant | ELISA Conc. (ng/mL) | ActRIIa binding | BMPRII binding | BMPRIa binding | BMPRIb binding |
|---|---|---|---|---|---|---|---|
| M | 23 | S | 15.20 | 2.20 | 2.41 | 0.88 | 1.09 |
| W | 52 | A | 37.78 | 1.69 | 1.25 | 0.92 | 0.33 |
| W | 55 | N | 10.93 | 0.41 | 0.82 | 0.35 | 0.00 |
| F | 73 | S | 15.45 | 2.54 | 2.84 | 0.90 | 0.25 |
| F | 73 | D | 26.89 | 2.50 | 3.05 | 0.33 | 0.64 |
| F | 73 | Q | 74.76 | 1.87 | 2.85 | 1.05 | 1.71 |
| F | 73 | E | 138.00 | 1.87 | 1.77 | 0.55 | 1.23 |
| F | 73 | A | 153.25 | 1.13 | 0.82 | 0.55 | 1.05 |
| F | 73 | A | 84.87 | 0.56 | 0.25 | 0.00 | 0.53 |
| Y | 78 | D | 517.04 | 1.93 | 2.72 | 1.05 | 2.01 |
| Y | 78 | T | 714.26 | 1.63 | 2.66 | 0.87 | 2.40 |
| Y | 78 | S | 789.68 | 1.58 | 1.77 | 1.29 | 2.75 |
| L | 21 | N | 414.21 | 1.03 | 1.73 | 1.57 | 2.81 |
| L | 21 | G | 12.36 | 1.50 | 2.30 | 2.53 | 3.65 |
| Y | 44 | N | 13.63 | 0.45 | 1.46 | 2.05 | 1.81 |
| F | 73 | T | 192.64 | 2.29 | 3.41 | 2.04 | 2.86 |
| Y | 44 | T | 21.46 | 0.36 | 0.25 | 1.09 | 1.33 |
| W | 55 | R | 47.80 | 1.20 | 1.52 | 1.75 | 2.17 |
| F | 73 | G | 22.42 | 1.41 | 1.55 | 1.36 | 1.64 |
| F | 73 | K | 24.61 | 0.61 | 0.38 | 0.69 | 1.14 |
| F | 73 | G | 172.77 | 1.73 | 1.26 | 1.16 | 1.53 |
| F | 73 | T | 154.57 | 1.92 | 1.93 | 1.12 | 1.44 |
| Y | 78 | R | 263.91 | 2.26 | 3.13 | 1.36 | 2.39 |
| Y | 78 | P | 1249.23 | 0.92 | 0.85 | 0.75 | 0.69 |
| I | 86 | K | 2214.38 | 0.97 | 1.02 | 0.81 | 0.69 |
| I | 86 | E | 2555.62 | 1.00 | 1.13 | 0.66 | 0.69 |
| I | 86 | Q | 3007.62 | 0.96 | 1.07 | 0.66 | 0.82 |
| L | 90 | R | 338.46 | 0.47 | 0.13 | 0.29 | 0.32 |
| L | 90 | T | 647.00 | 0.66 | 0.29 | 0.48 | 0.64 |
| L | 90 | E | 234.92 | 0.24 | 0.18 | 0.20 | 0.27 |
| L | 90 | R | 356.38 | 0.47 | 0.12 | 0.22 | 0.48 |
| F | 93 | A | 11.61 | 0.11 | 0.09 | 0.10 | 0.24 |
| F | 93 | E | 645.77 | 0.79 | 0.62 | 0.83 | 0.99 |
| F | 93 | D | 52.77 | 0.80 | 0.62 | 0.96 | 0.91 |
| F | 93 | T | 287.00 | 0.79 | 0.81 | 0.77 | 0.88 |
| L | 115 | A | 24.24 | 0.01 | -0.01 | -0.02 | 0.17 |
| F | 117 | R | 603.69 | 0.35 | 0.72 | 0.47 | 0.71 |
| F | 117 | K | 329.23 | 0.34 | 0.20 | 0.43 | 0.62 |
| L | 90 | H | 61.98 | 0.47 | 0.20 | 0.36 | 0.55 |
| L | 90 | P | 109.40 | 0.75 | 0.17 | 0.46 | 0.52 |
| L | 90 | G | 91.95 | 0.87 | 0.28 | 0.55 | 0.65 |
| F | 93 | H | 233.85 | 0.98 | 1.20 | 1.03 | 1.04 |
| F | 93 | G | 23.58 | 0.63 | 0.35 | 0.60 | 0.53 |
| Y | 116 | Y | 1921.77 | 1.02 | 1.12 | 1.07 | 0.79 |
| F | 117 | S | 42.22 | 0.11 | -0.04 | 0.15 | -0.08 |
| F | 117 | Y | 1682.15 | 1.03 | 0.96 | 1.07 | 0.73 |
| V | 123 | G | 304.85 | 0.53 | 0.22 | 0.67 | 0.17 |
| L | 21 | R | 681.69 | 0.84 | 0.66 | 0.83 | 1.01 |
| L | 21 | E | 332.00 | 0.25 | 0.07 | 0.12 | 0.16 |
| L | 21 | D | 999.08 | 0.94 | 0.94 | 1.01 | 1.52 |
| M | 23 | N | 600.08 | 0.94 | 0.90 | 0.98 | 1.36 |
| V | 26 | G | 604.77 | 1.07 | 1.00 | 1.08 | 1.66 |
| V | 26 | N | 976.38 | 1.00 | 0.97 | 1.14 | 1.43 |
| V | 26 | E | 1020.54 | 1.02 | 0.73 | 1.02 | 1.38 |
| W | 52 | P | 407.15 | 0.07 | 0.01 | 0.03 | 0.14 |
| W | 55 | A | 26.22 | 0.09 | 0.03 | 0.10 | 0.23 |
| I | 57 | I | 525.77 | 1.05 | 1.20 | 1.01 | 1.53 |
| I | 57 | L | 23.04 | 0.90 | 0.40 | 0.92 | 1.17 |
| F | 73 | N | 321.23 | 0.89 | 0.85 | 0.51 | 0.95 |
| Y | 78 | H | 1489.38 | 1.07 | 1.47 | 1.36 | 1.34 |
| I | 86 | D | 1703.85 | 1.09 | 1.31 | 1.03 | 1.18 |
| I | 94 | Q | 854.46 | 1.10 | 1.32 | 0.74 | 0.74 |
| Y | 128 | K | 452.40 | 1.11 | 1.78 | 1.40 | 1.57 |
| K | 39 | N | 69.00 | 1.08 | 0.99 | 1.98 | 1.63 |
| K | 39 | A | 8898.00 | 1.06 | 1.51 | 3.48 | 2.86 |
| K | 39 | S | 7148.00 | 1.04 | 1.37 | 2.77 | 2.23 |
| R | 48 | E | 73.90 | 0.34 | -0.13 | 0.45 | -0.51 |
| R | 48 | Q | 743.20 | 0.80 | 0.15 | 1.06 | 0.85 |
| R | 48 | N | 410.20 | 0.93 | 0.13 | 1.87 | 0.43 |
| R | 48 | H | 42.82 | 1.02 | 0.58 | 3.15 | 3.58 |

TABLE 14-continued

Receptor binding affinity of BMP-7 Library 1 variants.

| wt | res# | variant | ELISA Conc. (ng/mL) | ActRIIa binding | BMPRII binding | BMPRIa binding | BMPRIb binding |
|---|---|---|---|---|---|---|---|
| Q | 53 | G | 82.88 | 0.99 | 1.37 | 3.70 | 3.95 |
| Q | 53 | R | 149.28 | 0.81 | 0.96 | 1.26 | 1.41 |
| Q | 53 | E | 1236.80 | 0.98 | 0.72 | 2.30 | 2.78 |
| Q | 53 | D | 6876.00 | 0.89 | 1.01 | 2.20 | 3.74 |
| Q | 53 | K | 485.40 | 0.73 | 0.14 | 0.70 | 2.03 |
| Q | 53 | T | 5296.00 | 1.24 | 1.28 | 0.80 | 0.90 |
| Q | 53 | T | 4072.00 | 1.14 | 1.23 | 0.73 | 0.85 |
| Q | 53 | S | 5978.00 | 1.04 | 1.26 | 0.66 | 0.68 |
| E | 60 | R | 122.78 | 0.68 | 0.77 | 0.35 | 0.23 |
| E | 60 | P | 145.10 | 0.94 | 1.01 | 0.47 | 0.53 |
| E | 60 | H | 128.78 | 0.86 | 1.25 | 0.34 | 0.42 |
| E | 60 | R | 148.04 | 0.80 | 0.40 | 0.43 | 0.50 |
| N | 76 | T | 4576.00 | 1.11 | 0.97 | 0.94 | 0.98 |
| N | 76 | D | 7534.00 | 1.13 | 0.87 | 0.84 | 0.80 |
| N | 76 | Y | 813.80 | 0.92 | 0.60 | 0.46 | 0.46 |
| N | 76 | N | 4998.00 | 1.05 | 1.12 | 0.72 | 0.78 |
| N | 76 | A | 5570.00 | 0.96 | 0.95 | 0.79 | 0.81 |
| N | 76 | S | 8816.00 | 0.99 | 0.98 | 0.76 | 0.85 |
| S | 77 | A | 24.84 | 0.91 | 0.80 | 0.55 | 0.76 |
| S | 77 | T | 15.45 | 1.15 | 0.97 | 0.77 | 0.79 |
| S | 77 | E | 45.54 | 1.17 | 0.98 | 0.81 | 0.94 |
| S | 77 | P | 691.00 | 1.00 | 0.91 | 0.58 | 0.79 |
| S | 77 | A | 1194.00 | 1.05 | 0.84 | 0.85 | 0.92 |
| S | 77 | H | 48.80 | 0.42 | 0.08 | 0.29 | 0.30 |
| K | 126 | E | 24.45 | 0.26 | 0.00 | 0.23 | 0.22 |
| K | 126 | Q | 145.46 | 0.81 | 0.28 | 0.46 | 0.57 |
| R | 129 | N | 573.40 | 1.10 | 1.40 | 0.89 | 1.03 |
| R | 129 | D | 1305.00 | 1.13 | 1.86 | 0.93 | 1.16 |
| R | 129 | S | 45.52 | 0.62 | 0.26 | 0.32 | 0.37 |
| R | 129 | K | 410.80 | 1.12 | 0.78 | 0.69 | 0.77 |
| R | 134 | K | 830.00 | 1.18 | 0.91 | 1.05 | 1.11 |
| R | 134 | R | 249.28 | 1.09 | 0.81 | 0.87 | 0.90 |
| R | 134 | S | 4314.00 | 1.17 | 1.07 | 1.10 | 1.15 |
| K | 39 | T | 19.26 | 0.98 | 0.75 | 0.74 | 0.86 |
| K | 39 | D | 18.87 | 0.88 | 0.72 | 0.67 | 0.82 |
| Q | 53 | A | 27.33 | 0.84 | 0.26 | 0.54 | 0.65 |
| E | 60 | S | 97.16 | 1.02 | 0.88 | 0.74 | 0.87 |
| S | 77 | T | 1047.80 | 0.99 | 0.93 | 0.94 | 0.90 |
| S | 77 | P | 1302.20 | 0.92 | 0.85 | 0.68 | 0.95 |
| K | 126 | G | 55.32 | 0.53 | 0.12 | 0.30 | 0.35 |
| R | 134 | P | 125.14 | 0.89 | 0.50 | 0.54 | 0.60 |
| R | 134 | R | 927.00 | 1.11 | 1.02 | 0.86 | 0.98 |
| R | 134 | L | 9016.00 | 0.99 | 1.00 | 1.03 | 1.02 |

To further characterize receptor binding, dose-response binding assays, using 12-point serial dilutions from conditioned media, were conducted for selected Library 1 variants.

Next, dissociation constants ($K_D$ below) were calculated for each variant using the nonlinear regression—one site hyperbolic binding model in Prism. Note that the experiment was repeated for the wild type protein. The relative binding constants may be compared to determine whether the specificity of each variant is appreciably different from wild type.

TABLE 16

Dissociation constants for BMP-7 Library 1 variants

| variant | ActRIIa $K_D$ | BMPRII $K_D$ | BMPRIa $K_D$ | BMPRIb $K_D$ |
|---|---|---|---|---|
| WT | 0.40 | 1.28 | 1.61 | 1.77 |
| WT | 0.28 | 0.98 | 1.53 | 0.33 |
| L21G | 0.43 | 2.01 | 1.65 | 0.77 |
| L21K | 0.84 | 3.09 | 2.92 | 1.75 |
| L21N | 3.38 | 5.01 | 7.48 | 5.02 |
| L21R | 0.31 | 2.14 | 3.32 | 1.60 |
| M23G | 0.31 | 0.88 | 2.89 | 2.53 |

TABLE 16-continued

Dissociation constants for BMP-7 Library 1 variants

| variant | ActRIIa $K_D$ | BMPRII $K_D$ | BMPRIa $K_D$ | BMPRIb $K_D$ |
|---|---|---|---|---|
| M23N | 0.06 | 0.99 | 1.79 | 1.07 |
| M23R | 0.00 | 2.16 | 1.69 | 1.75 |
| M23S | 0.58 | 3.03 | 2.77 | 1.39 |
| V26E | 2.39 | 15.80 | 9.89 | 6.13 |
| V26G | 1.71 | 3.93 | 5.76 | 12.74 |
| V26K | 2.42 | 18.29 | 7.02 | 6.98 |
| V26N | 1.88 | 9.33 | 7.94 | 5.45 |
| K39A | 0.08 | 0.68 | 1.97 | 1.13 |
| K39S | 0.12 | 0.88 | 1.65 | 1.11 |
| Y44A | 1.57 | 4.27 | 5.54 | 2.39 |
| Y44D | 2.08 | 44.04 | 3.71 | 2.18 |
| Y44G | 1.10 | 21.39 | 4.98 | 2.56 |
| Y44N | 0.80 | 3.34 | 2.92 | 2.63 |
| Y44P | 0.80 | 11.56 | 6.46 | 1.67 |
| Y44S | 0.53 | 6.26 | 3.48 | 1.82 |
| R48H | 0.23 | 2.38 | 2.57 | 1.04 |
| R48N | 0.26 | 3.14 | 2.78 | 1.10 |
| R48Q | 1.42 | 5.37 | 5.17 | 5.16 |
| W52A | 0.45 | 8.16 | 5.00 | 1.61 |
| Q53A | 0.52 | 2.04 | 2.92 | 2.01 |
| Q53D | 1.32 | 5.37 | 5.22 | 4.45 |
| Q53G | 0.06 | 0.82 | 0.73 | 0.72 |
| Q53H | 0.53 | 7.97 | 3.38 | 2.13 |
| Q53K | 0.21 | 1.31 | 1.57 | 1.46 |
| Q53S | 0.13 | 1.12 | 1.36 | 1.07 |
| Q53T | 0.09 | 0.80 | 1.36 | 1.13 |
| W55N | 0.55 | 5.52 | 5.99 | 1.99 |
| I57H | 0.56 | 5.34 | 3.70 | 2.47 |
| I57I | 0.13 | 1.23 | 1.36 | 0.67 |
| I57L | 0.09 | 0.71 | 1.32 | 0.81 |
| E60K | 0.70 | 3.71 | 4.03 | 3.25 |
| E60Q | 0.49 | 2.32 | 2.93 | 2.11 |
| E60R | 0.41 | 1.01 | 2.76 | 2.58 |
| A63Q | 0.51 | 0.98 | 2.20 | 1.09 |
| A63S | 0.61 | 2.29 | 2.90 | 1.30 |
| Y65D | 0.45 | 1.11 | 2.19 | 1.11 |
| A72D | 0.46 | 1.56 | 2.68 | 1.30 |
| A72H | 0.54 | 2.55 | 1.98 | 1.71 |
| A72N | 0.81 | 3.21 | 4.02 | 1.25 |
| A72S | 0.35 | 1.50 | 2.48 | 1.04 |
| F73E | 0.72 | 34.63 | 4.25 | 1.79 |
| F73S | 0.18 | 1.72 | 2.33 | 1.08 |
| Y78H | 0.10 | 1.05 | 1.46 | 1.12 |
| Y78R | 0.94 | 11.65 | 3.90 | 1.68 |
| Y78S | 0.19 | 1.10 | 1.40 | 0.98 |
| N83P | 0.18 | 0.77 | 1.39 | 1.78 |
| I86A | 0.16 | 1.12 | 3.55 | 1.12 |
| I86D | 0.85 | 11.19 | 24.59 | 8.03 |
| Q88E | 1.33 | 8.96 | 9.65 | 7.32 |
| L90N | 1.11 | 12.59 | 7.26 | 5.23 |
| F93D | 0.40 | 3.02 | 1.18 | 1.20 |
| F93E | 0.73 | 17.88 | 3.57 | 1.33 |
| F93G | 0.43 | 1.21 | 6.15 | 5.35 |
| F93H | 0.14 | 0.84 | 1.35 | 0.71 |
| F93Q | 0.94 | 4.44 | 6.25 | 3.46 |
| F93R | 1.11 | 8.96 | 9.30 | 5.95 |
| F93S | 0.61 | 1.89 | 1.11 | 1.37 |
| F93T | 0.74 | 1.85 | 3.94 | 1.34 |
| I94E | 3.02 | 9.73 | 14.20 | 8.08 |
| I94H | 0.93 | 9.03 | 7.10 | 4.62 |
| I94K | 1.07 | 1.07 | 4.74 | 3.05 |
| I94R | 0.68 | 1.07 | 3.70 | 1.78 |
| N95K | 2.13 | 1.49 | 8.31 | 1.46 |
| N95R | 5.35 | 14.15 | 14.18 | 11.13 |
| E97D | 0.38 | 1.27 | 3.35 | 1.40 |
| E97K | 0.65 | 2.36 | 7.88 | 2.72 |
| E97R | 0.24 | 1.38 | 2.22 | 0.31 |
| T98A | 0.20 | 1.17 | 2.09 | 0.27 |
| T98E | 0.14 | 1.41 | 1.95 | 0.35 |
| T98K | 0.18 | 1.04 | 1.72 | 0.33 |
| T98X | 0.15 | 1.32 | 1.60 | 0.34 |
| A105V | 0.15 | 1.01 | 1.11 | 0.41 |
| Q108D | 0.14 | 0.84 | 2.01 | 0.42 |
| Q108S | 0.15 | 1.25 | 0.95 | 0.46 |
| N110D | 0.20 | 0.35 | 0.62 | 0.34 |
| N110E | 0.28 | 0.68 | 0.98 | 0.39 |
| Y116H | 0.28 | 1.96 | 2.12 | 0.41 |
| Y116Y | 0.25 | 1.06 | 2.20 | 0.93 |
| F117H | 0.16 | 0.84 | 1.43 | 0.28 |
| F117R | 0.65 | 5.54 | 4.17 | 1.17 |
| F117Y | 1.26 | 5.15 | 5.11 | 6.81 |
| S120D | 0.10 | 1.07 | 0.89 | 0.30 |
| R129D | 0.26 | 0.43 | 2.22 | 1.40 |
| R129N | 2.66 | 1.78 | 7.85 | 8.90 |
| R134E | 0.31 | 1.07 | 2.43 | 0.55 |
| R134L | 0.29 | 1.75 | 12.33 | 1.23 |
| R134R | 0.39 | 6.16 | 4.26 | 2.72 |
| R134S | 1.48 | 3.19 | 5.21 | 4.56 |
| A135E | 0.08 | 1.22 | 0.99 | 0.38 |
| A135S | 0.17 | 1.31 | 0.67 | 0.44 |
| H139R | 0.15 | 1.41 | 1.00 | 0.37 |

Based on the above-described results, the vast majority of the variants have receptor binding affinities that are similar to wild type BMP-7. The following variants appear to have altered specificity for the type II receptors: M23N, Q53G, Q53H, and I86D. Q53H and I86D bind to ActRIIa with similar affinity to wild type, but bind BMPRII with approximately 10-fold reduced affinity relative to wild type. M23N and Q53G bind to ActRIIa with approximately 10-fold increased affinity relative to wild type, but bind BMPRII with similar affinity to wild type.

Example 11

Characterization of Library 1 BMP Variants Using the C2C12 Bioassay

The biological activity of human and variant BMP-7 molecules was measured using the C2C12 bioassay. C2C12 cells are a mouse myoblastic cell line that differentiates in response to BMPs such as BMP-7. C2C12 cells were trypsinized and diluted to approximately 60,000 cells/mL in C2C12 media (DMEM, 4 mM L-glutamine, 1.5 g/L sodium bicarbonate, 4.5 g/L glucose, 10% FBS, and antibiotics). 50 μL (3000 cells) were dispensed into each well of a 96-well plate and incubated overnight at 37° C. The next day, 50 μL of BMP-7 containing solution (for example, diluted conditioned media obtained from the BMP-7 expression protocol above, or purified recombinant human BMP-7 of a known concentration) was added to each well; each sample was tested in duplicate. The plates were incubated for 3 days at 37° C. The plates were then washed twice with 150 μL TBS (50 mM Tris pH 7.5, 150 mM NaCl). 25 μL TBS with 1% Triton-X100 was added to each well and the plate was incubated for 10-20 minutes at 4° C. 100-150 μL CSPD SapphireII luminescent alkaline phosphatase substrate (Applied Biosystems #T2210) was added to each well and incubated at room temperature in the dark. Luminescence readings were obtained for each well using the TopCount plate reader. Luminescence of the BMP-7 variants were compared to the luminescence of known quantities of recombinant human BMP-7 in order to determine the relative biological activity of the variants.

The table below shows the bioactivity of a selection of BMP-7 variants relative to the wild type protein (normalized to 1.0). Note that the assays were performed using a fixed volume of conditioned media rather than a specific concentration of protein, so differences in expression levels as well as differences in receptor binding affinity may affect the results. Data is shown only for variants with expression yields greater than 10.0 ng/mL.

TABLE 17

Bioactivity of BMP-7 Library 1 variants

| var# | wt | res# | var | ELISA Conc. (ng/mL) | C2C12 Bioactivity |
|---|---|---|---|---|---|
| 1 | M | 23 | S | 15.20 | 8.65 |
| 6 | W | 52 | A | 37.78 | 0.11 |
| 9 | W | 55 | N | 10.93 | 0.06 |
| 13 | F | 73 | S | 15.45 | 0.11 |
| 14 | F | 73 | D | 26.89 | 0.03 |
| 15 | F | 73 | Q | 74.76 | 0.20 |
| 16 | F | 73 | E | 138.00 | 0.09 |
| 17 | F | 73 | A | 153.25 | 0.18 |
| 18 | F | 73 | A | 84.87 | −0.08 |
| 19 | Y | 78 | D | 517.04 | 0.13 |
| 20 | Y | 78 | T | 714.26 | 0.17 |
| 21 | Y | 78 | S | 789.68 | 0.09 |
| 22 | L | 21 | N | 414.21 | 1.21 |
| 23 | L | 21 | G | 12.36 | 4.34 |
| 28 | Y | 44 | N | 13.63 | 0.11 |
| 30 | F | 73 | T | 192.64 | 0.16 |
| 31 | Y | 44 | T | 21.46 | 0.13 |
| 33 | W | 55 | R | 47.80 | 0.51 |
| 37 | F | 73 | G | 22.42 | 0.07 |
| 39 | F | 73 | K | 24.61 | 0.11 |
| 40 | F | 73 | G | 172.77 | 0.13 |
| 41 | F | 73 | T | 154.57 | 0.17 |
| 42 | Y | 78 | R | 263.91 | 2.50 |
| 43 | Y | 78 | P | 1249.23 | 0.00 |
| 49 | I | 86 | K | 2214.38 | 0.01 |
| 50 | I | 86 | E | 2555.62 | 0.02 |
| 51 | I | 86 | Q | 3007.62 | 0.05 |
| 52 | L | 90 | R | 338.46 | 0.04 |
| 53 | L | 90 | T | 647.00 | 0.01 |
| 54 | L | 90 | E | 234.92 | 0.00 |
| 55 | L | 90 | R | 356.38 | 0.00 |
| 56 | F | 93 | A | 11.61 | 0.05 |
| 57 | F | 93 | E | 645.77 | 6.14 |
| 58 | F | 93 | D | 52.77 | 6.05 |
| 59 | F | 93 | T | 287.00 | 5.61 |
| 63 | L | 115 | A | 24.24 | −0.01 |
| 66 | F | 117 | R | 603.69 | 0.06 |
| 67 | F | 117 | K | 329.23 | 0.08 |
| 76 | L | 90 | H | 61.98 | 0.01 |
| 77 | L | 90 | P | 109.40 | −0.01 |
| 78 | L | 90 | G | 91.95 | −0.01 |
| 80 | F | 93 | H | 233.85 | 5.78 |
| 82 | F | 93 | G | 23.58 | 5.38 |
| 85 | Y | 116 | Y | 1921.77 | 2.34 |
| 86 | F | 117 | S | 42.22 | 0.00 |
| 87 | F | 117 | Y | 1682.15 | 1.84 |
| 88 | V | 123 | G | 304.85 | 0.31 |
| 97 | L | 21 | R | 681.69 | 1.20 |
| 98 | L | 21 | E | 332.00 | 0.00 |
| 99 | L | 21 | D | 999.08 | 0.89 |
| 100 | M | 23 | N | 600.08 | 1.54 |
| 103 | V | 26 | G | 604.77 | 2.13 |
| 104 | V | 26 | N | 976.38 | 2.75 |
| 105 | V | 26 | E | 1020.54 | 0.97 |
| 106 | W | 52 | P | 407.15 | 0.00 |
| 109 | W | 55 | A | 26.22 | −0.01 |
| 111 | I | 57 | I | 525.77 | 1.66 |
| 112 | I | 57 | L | 23.04 | 0.05 |
| 116 | F | 73 | N | 321.23 | −0.01 |
| 117 | Y | 78 | H | 1489.38 | 2.67 |
| 119 | I | 86 | D | 1703.85 | 0.20 |
| 120 | I | 94 | Q | 854.46 | 0.00 |
| 125 | Y | 128 | K | 452.40 | 0.12 |
| 137 | K | 39 | N | 69.00 | 0.13 |
| 140 | K | 39 | A | 8898.00 | 1.27 |
| 141 | K | 39 | S | 7148.00 | 0.96 |

TABLE 17-continued

Bioactivity of BMP-7 Library 1 variants

| var# | wt | res# | var | ELISA Conc. (ng/mL) | C2C12 Bioactivity |
|---|---|---|---|---|---|
| 143 | R | 48 | E | 73.90 | 0.00 |
| 144 | R | 48 | Q | 743.20 | 0.10 |
| 145 | R | 48 | N | 410.20 | 0.01 |
| 147 | R | 48 | H | 42.82 | 0.33 |
| 148 | Q | 53 | G | 82.88 | 1.00 |
| 149 | Q | 53 | R | 149.28 | 0.02 |
| 150 | Q | 53 | E | 1236.80 | 0.08 |
| 151 | Q | 53 | D | 6876.00 | 1.67 |
| 152 | Q | 53 | K | 485.40 | 0.04 |
| 153 | Q | 53 | T | 5296.00 | 0.72 |
| 154 | Q | 53 | T | 4072.00 | 1.20 |
| 155 | Q | 53 | S | 5978.00 | 1.52 |
| 156 | E | 60 | R | 122.78 | 0.17 |
| 159 | E | 60 | P | 145.10 | 0.73 |
| 160 | E | 60 | H | 128.78 | 0.32 |
| 161 | E | 60 | R | 148.04 | 0.28 |
| 162 | N | 76 | T | 4576.00 | 0.12 |
| 163 | N | 76 | D | 7534.00 | 0.01 |
| 164 | N | 76 | Y | 813.80 | 0.00 |
| 165 | N | 76 | N | 4998.00 | 1.18 |
| 166 | N | 76 | A | 5570.00 | 0.05 |
| 167 | N | 76 | S | 8816.00 | 0.20 |
| 168 | S | 77 | A | 24.84 | 0.32 |
| 169 | S | 77 | T | 15.45 | 0.00 |
| 170 | S | 77 | E | 45.54 | −0.01 |
| 171 | S | 77 | P | 691.00 | −0.01 |
| 172 | S | 77 | A | 1194.00 | 0.60 |
| 173 | S | 77 | H | 48.80 | 0.01 |
| 174 | K | 126 | E | 24.45 | 0.01 |
| 175 | K | 126 | Q | 145.46 | 0.21 |
| 182 | R | 129 | N | 573.40 | 1.50 |
| 183 | R | 129 | D | 1305.00 | 3.96 |
| 184 | R | 129 | S | 45.52 | 0.05 |
| 185 | R | 129 | K | 410.80 | 0.01 |
| 186 | R | 134 | K | 830.00 | 0.87 |
| 187 | R | 134 | R | 249.28 | 0.50 |
| 188 | R | 134 | S | 4314.00 | 3.76 |
| 190 | K | 39 | T | 19.26 | 0.06 |
| 191 | K | 39 | D | 18.87 | 0.01 |
| 192 | Q | 53 | A | 27.33 | 0.02 |
| 193 | E | 60 | S | 97.16 | 0.44 |
| 197 | S | 77 | T | 1047.80 | 0.01 |
| 199 | S | 77 | P | 1302.20 | 0.00 |
| 200 | K | 126 | G | 55.32 | 0.00 |
| 204 | R | 134 | P | 125.14 | 0.17 |
| 205 | R | 134 | R | 927.00 | 3.57 |
| 206 | R | 134 | L | 9016.00 | 3.76 |

Interestingly, a number of the library 1 variants have significantly greater bioactivity than the wild type Image clone. This observed increase in activity is likely due to increased expression yield, although additional factors including but not limited to altered stability, solubility, or receptor binding affinity may also influence the observed bioactivity. Substitutions that increase bioactivity by at least 2-fold relative to wild type include, but are not limited to, L21G, M23S, V26G, V26N, Y78H, Y78R, F93D, F93E, F93G, F93H, F93T, R129D, R134L, and R134S.

Example 12

Double Mutant Variants: BMP-7 Library 2

The point mutations from selected Library 1 variants were combined to yield a library of double mutants, referred to as Library 2. Methods for making and screening the Library 2 variants are as for the Library 1 variants described above. C2C12 bioassay data was determined at a single point by diluting conditioned media 1:66; due to the low expression yield of the Image clone, its bioassay signal is at background at this dilution.

TABLE 18

Expression yield and bioassay data, BMP-7 Library 2 variants.

| Variant Name | 293T ELISA (ng/mL) | Fold change: 293T | CHO ELISA (ng/mL) | Fold change: CHO | C2C12 @ 1:66 | Western Blot Band Intensity |
|---|---|---|---|---|---|---|
| L21G-Y65N | 4261.8 | 2.1 | 73.7 | 3.6 | 0.09 | ++ |
| L21G-F93H | 23923.5 | 12.0 | 20.8 | 1.1 | 0.23 | ++ |
| L21R-Y65N | 4371.2 | 2.2 | 59.9 | 2.9 | 0.16 | ++ |
| M23R-Y65N | 5468.8 | 2.7 | 182.3 | 8.8 | 0.20 | ++ |
| K39A-F93H | 37258.8 | 18.6 | 222.5 | 10.8 | 0.66 | ++ |
| K39S-Y65N | 5259.4 | 2.6 | 39.4 | 1.9 | 0.13 | ++ |
| K39S-A72D | 3703.5 | 1.9 | 0.7 | 0.0 | 0.05 | ++ |
| K39S-Y78H | 18617.6 | 9.3 | 173.8 | 8.4 | 0.02 | ++ |
| K39S-I86A | 4231.2 | 2.1 | 16.3 | 0.8 | 0.05 | ++ |
| K39S-I94R | 4.9 | 0.0 | 0.3 | 0.0 | 0.04 | ++ |
| K39S-F93S | 3256.5 | 1.6 | 45.7 | 2.2 | 1.23 | +++ |
| K39S-Q108D | 5472.9 | 2.7 | 42.4 | 2.1 | 0.07 | +++ |
| K39S-N110D | 19964.7 | 10.0 | 171.8 | 8.3 | 0.49 | ++ |
| K39S-S120D | 21147.1 | 10.6 | 134.3 | 6.5 | 0.46 | +++ |
| K39S-R129D | 2048.8 | 1.0 | 34.0 | 1.6 | 0.28 | ++ |
| K39S-N130D | 3918.2 | 2.0 | 284.5 | 13.8 | 0.20 | ++ |
| K39S-R134E | 20564.7 | 10.3 | 6.2 | 0.3 | 0.28 | ++ |
| K39S-R134S | 18847.1 | 9.4 | 35.1 | 1.7 | 0.20 | ++ |
| K39S-A135E | 17694.1 | 8.8 | 159.9 | 7.8 | 0.03 | ++ |
| K39S-A135S | 2783.5 | 1.4 | 22.8 | 1.1 | 0.03 | ++ |
| K39S-H139R | 2868.8 | 1.4 | 37.2 | 1.8 | 0.03 | ++ |
| Q53D-Y65N | 22552.9 | 11.3 | 88.7 | 4.3 | 0.02 | ++ |
| I57L-Y65N | 18982.4 | 9.5 | 158.7 | 7.7 | 0.02 | ++ |
| Y65N-Y78H | 27923.5 | 14.0 | 197.3 | 9.6 | 0.13 | ++ |
| Y65N-Y78R | 20076.5 | 10.0 | 185.7 | 9.0 | 0.06 | ++ |
| Y65N-S120D | 23794.1 | 11.9 | 218.3 | 10.6 | 0.66 | +++ |
| Y65N-A135S | 22023.5 | 11.0 | 51.5 | 2.5 | 0.12 | ++ |
| A72D-F93H | 23329.4 | 11.7 | 369.2 | 17.9 | 0.17 | ++ |
| Y78H-F93H | 18117.6 | 9.1 | 395.7 | 20.5 | 0.36 | ++ |
| Y78H-Q108D | 35176.5 | 17.6 | 0.7 | 0.0 | 0.27 | ++ |
| Y78H-Y116H | 23688.2 | 11.8 | 70.8 | 3.2 | 0.01 | + |
| Y78H-F117Y | 21794.1 | 10.9 | 62.3 | 5.5 | 0.07 | ++ |
| Y78H-S120D | 27864.7 | 13.9 | 179.6 | 12.5 | 0.34 | ++ |
| Y78H-R134E | 40129.4 | 20.1 | 410.1 | 21.6 | 0.72 | ++ |
| Y78H-R134S | 49617.6 | 24.8 | 36.3 | 2.4 | 0.68 | ++ |
| Y78H-A135E | 49729.4 | 24.9 | 167.6 | 9.6 | 0.03 | ++ |
| Y78H-A135S | 34458.8 | 17.2 | 43.4 | 2.2 | 0.05 | ++ |
| Y78H-H139R | 37770.6 | 18.9 | 40.5 | 2.1 | 0.14 | ++ |
| F93H-F117Y | 24747.1 | 12.4 | 296.0 | 14.4 | 0.40 | ++ |
| F93H-S120D | 35758.8 | 17.9 | 276.1 | 13.4 | 1.14 | ++ |
| F93H-R134S | 33800.0 | 16.9 | 378.7 | 18.4 | 1.21 | ++ |
| F93H-H139R | 39929.4 | 20.0 | 279.5 | 13.6 | 0.53 | ++ |

As may be seen above, a number of the Library 2 variants have significantly increased expression yield, in both 293T and CHO cells, relative to the wild type Image clone. Preferred variants show at least a 10-fold increase in at least one expression host; examples of such variants include but are not limited to L21G/F93H, K39A/F93H, K39S/N110D, K39S/S120D, K39S/N130D, K39S/R134E, Q53D/Y65N, Y65N/Y78H, Y65N/Y78R, Y65N/S120D, Y65N/A135S, A72D/F93H, Y78H/F93H, Y78H/Q108D, Y78H/Y116H, Y78H/F117Y, Y78H/S120D, Y78H/R134E, Y78H/R134S, Y78H/A135E, Y78H/A135S, Y78H/H139R, F93H/F117Y, F93H/S120D, F93H/R134S, F93H/H139R. Especially preferred variants show at least a 10-fold increase in expression yield in both 293T and CHO cells; examples of such variants include but are not limited to K39A/F93H, Y65N/S120D, A72D/F93H, Y78H/S120D, Y78H/R134E, Y78H/A135E, F93H/F117Y, F93H/S120D, F93H/R134S, and F93H/H139R.

Example 13

Expression Yield of Triple, Quadruple, and Higher-Order Mutants.

Triple, quadruple, and higher order mutants of BMP-7 were made and tested as described above. A number of these variants exhibit significantly increased expression yield or significantly increased bioactivity. Note that ELISA substantially underestimates the protein concentration of a substantial fraction of these variants due to decreased antibody binding affinity.

TABLE 19

Expression yield in 293T cells and bioactivity data for selected triple variants with high expression yield in 293T cells

| Variant Name | ELISA Conc. (ng/mL) | Fold Increase Expression Yield | Fold Increase C2C12 Bioactivity | Western Blot Band Intensity |
|---|---|---|---|---|
| K39S/S120D/Y78H | 50100.0 | 96.8 | 7.1 | +++ |
| Y78H/F93H/F117H | 43490.0 | 84.0 | 23.0 | +++ |
| Y78H/F93H/Q108D | 42880.0 | 82.8 | 21.6 | +++ |
| Y78H/F93H/A72D | 42590.0 | 82.3 | 14.6 | +++ |
| K39S/S120D/Q108D | 41170.0 | 79.5 | 15.6 | +++ |
| Y78H/F93H/Y65N | 34830.0 | 79.4 | 21.3 | +++ |
| Y78H/F93H/S120D | 40260.0 | 77.8 | 26.6 | +++ |
| Y78H/R134E/Y65N | 40210.0 | 77.7 | 42.2 | ++++ |
| K39S/S120D/Y65N | 34260.0 | 66.2 | 17.8 | +++ |
| K39S/S120D/A72D | 34070.0 | 65.8 | 25.9 | +++ |
| K39S/S120D/R134E | 32320.0 | 62.4 | 37.9 | +++ |
| K39S/S120D/M23R | 32060.0 | 61.9 | 14.3 | +++ |
| K39S/S120D/H139R | 29930.0 | 57.8 | 21.2 | ++ |
| K39S/S120D/R129D | 5910.0 | 11.4 | 22.7 | +++ |
| Y78H/R134E/M23R | 4775.0 | 9.2 | 27.7 | ++ |
| Y78H/R134E/L21G | 4763.0 | 9.2 | 28.4 | ++ |
| Y78H/R134E/A72D | 3269.0 | 6.3 | 43.6 | ++++ |
| K39S/S120D/F93H | 2950.0 | 5.7 | 2.1 | + |
| K39S/S120D/F93S | 2031.0 | 4.6 | 45.3 | +++ |

All of the above triples have expression yields that are at least 50-fold higher than wild type, and at least 2-fold higher than the best doubles. Furthermore, the majority of the above triples have significantly increased bioactivity relative to wild type and the best doubles. Triple variants with especially high bioactivity include, but are not limited to, K39S/F93S/S120D, K39S/S120D/R134E, Y65N/Y78H/R134E, and A72D/Y78H/R134E.

TABLE 20

Expression yield in CHO-K1 cells and bioactivity data for selected triple variants with high expression yield in CHO-K1 cells

| Variant Name | ELISA Conc. (ng/mL) | Fold Increase Expression Yield | Fold Increase C2C12 Bioactivity | Western Blot Band Intensity |
|---|---|---|---|---|
| Y78H/R134E/Y65N | 316.2 | 17.1 | 3.6 | − |
| Y78H/F93H/S120D | 316.1 | 17.1 | 2.8 | − |
| K39S/S120D/R134E | 245.7 | 13.3 | 21.8 | + |
| Y78H/R134E/A72D | 232.1 | 12.5 | 14.7 | + |
| K39S/S120D/Q108D | 219.8 | 11.9 | 2.4 | − |
| Y78H/F93H/Y65N | 200.0 | 10.8 | 1.6 | − |
| Y78H/R134E/L21G | 198.0 | 10.7 | 2.8 | − |
| Y78H/F93H/Q108D | 115.3 | 6.2 | 2.9 | − |
| Y78H/F93H/A72D | 107.1 | 5.8 | 2.0 | − |
| Y78H/R134E/M23R | 78.8 | 4.3 | 6.4 | − |
| Y78H/F93H/F117H | 58.7 | 3.2 | 1.0 | − |
| K39S/S120D/A72D | 46.8 | 2.5 | 1.6 | − |
| K39S/S120D/R129D | 42.9 | 2.3 | 28.0 | + |
| K39S/S120D/F93S | 38.4 | 2.1 | 78.7 | + |
| K39S/S120D/H139R | 33.8 | 1.8 | 1.5 | − |

Preferred variants with dramatic increases in CHO-K1 expression yield or C2C12 bioactivity include but are not limited to K39S/F93S/S120D, K39S/S120D/R129D, K39S/S120D/R134E, Y65N/Y78H/R134E, and Y78H/F93H/S120D.

Additional triple mutants were generated to determine the impact of different substitutions on receptor and inhibitor binding specificity. These variants included the Y65N and S120D substitutions, which confer increased expression yield and do not significantly affect receptor or inhibitor binding, and one additional substitution that may alter binding specificity. Triples comprising Y65N/S120D, and one of the following substitutions were made: M23R, R48H, R48N, R48Q, Q53G, Q53H, Q53K, Q53T, E60R, F73S, F73T, Y78D, Y78S, Y78T, I86D, K126R, Y128D, Y128H, and Y128Q.

Example 14

Purification of BMP-7 Variants

Y65N/S120D was partially purified using conventional chromatography. Heparin-sulphate sepharose (17-0407-01) was equilibrated in PBS. Conditioned media containing the Y65N/S120D variant was diluted 1:1 with 40 mM phosphate pH 6.5 filtered through a 0.45 micron filter, loaded onto the column, washed with 2-3 column volumes of PBS, and eluted in a single isocratic step with PBS/1M NaCl. The heparin bound fractions were dialyzed into 20 mM phosphate, 50 mM NaCl pH 7.0, loaded onto a SP-sepharose column, and eluted with a linear gradient (0-100% PBS/1M NaCl). A second purification protocol was used for larger scale purification of variants 457 (K39S/F93S), 471 (K39S/N130D), 492 (Y65N/Y78H), 504 (Y65N/S120D), 526 (K39S/S120D/R134E), and 565 (Y65N/F93T/R129D). Conditioned media was diluted 1:1 at neutral pH to lower the salt concentration to ~75 mM and loaded onto a SP-sepharose column. The column was then washed in 75 mM salt and then 300 mM salt, and BMP-7 was eluted with 1M salt.

Example 15

Receptor, Antibody, and Inhibitor Binding of Selected Variants

The binding of selected variants to BMP receptors, antibodies, and inhibitors was characterized using a fluorescence binding assay and the AlphaScreen™ assay. BMP-7 variant Y65N/S120D, partially purified as described above, was labeled with the dye AlexaFluor 568 (Molecular Probes). Small-scale (25 uL) reactions were performed using 15 uM BMP-7 and dye concentrations ranging from 0.3 uM to 1000 uM. Reactions using 333 uM and 10 uM dye then were performed using 750 uL protein. The reaction was quenched with Tris pH 8.0 and cleaned up using a PD-10 desalt column; the second fraction was used in the experiments described below. BMP-7 was also labeled with C6-FXS, a FITC-derived fluorophore with a 6-carbon spacer between the fluor and the NHS group. Labeling conditions with various ratios of protein to dye were tested, in 20 mM PO4, 500 mM NaCl, pH 7 solution. After establishing labeling conditions, 500 ug Y65N/S120D was labeled. Excess dye was removed by centrifugation and a PD-10 desalt column.

The flourescently labeled BMP-7 was added to serial dilutions of receptor/Fc fusions of the BMP-7 receptors ActRIa, BMPRIa, BMPRIb, ActRIIa, ActRIIb, and BMPRII (R&D Systems). Experiments were also performed in which the fluorescently labeled BMP-7 was added to serial dilutions of noggin/Fc or gremlin (R&D Systems). The labeled BMP-7 and receptor or inhibitor was allowed to incubate, and the fluorescence polarization and intensity was measured using a TopCount plate reader. Significant changes in intensity or anisotropy were observed for all of the receptors and inhibitors tested, for at least one of the labeled BMP-7 molecules.

Binding affinity of different BMP variants to these receptors and inhibitors may be determined by performing competition experiments. To perform these experiments, labeled BMP-7 and receptor or inhibitor are combined in amounts that yield an appreciable change in anisotropy or intensity relative to free labeled BMP-7. Then, varying amounts of a second, unlabeled BMP-7 molecule are added and the change in anisotropy or polarization is measured. The EC50 is then given by the concentration of competitor when half of the labeled BMP-7 is bound and half is free.

The Y65N/S120D variant of BMP-7 was also biotinylated for use in AlphaScreen assays using NHS-biotin. Bioactivity of the biotinylated protein was confirmed. AlphaScreen assays were performed to determine the binding affinity of selected BMP-7 variants for Fc fusions of the receptors BMPRIa, BMPRIb, ActRIIa, and BMPRII and the inhibitor noggin (R&D Systems). AlphaScreen assays were also performed to determine the affinity of selected variants for an anti-BMP-7 monoclonal antibody (R&D Systems mAb 3541). In all cases, 12-point binding curves were obtained in triplicate. Each data point corresponds to the luminescence produced from a solution comprising 10 uL of serially diluted BMP-7 variant, 10 uL receptor, inhibitor, or antibody, 10 uL biotinylated BMP-7, 10 uL AlphaScreen™ acceptor beads, and 10 uL AlphaScreen™ donor beads. Prism was used to calculate EC50 values for selected experiments.

TABLE 21

EC50 of wild type human BMP-7 (R&D Systems) and BMP-7 variants 504, 526, and 565 for the BMP receptors BMPRIb, ActRIIa, and BMPRII and the BMP inhibitor noggin, as determined using AlphaScreen ™ assays.

| BMP-7 variant | Receptor or inhibitor | EC(50) (ug/mL) | EC50 (ng/mL) | log(EC50) (ug/mL) | log(EC50) (ng/mL) | std. error (logEC50) ug/mL | Fold change vs. wt |
|---|---|---|---|---|---|---|---|
| wt | BMPRIb | 0.0499 | 49.9 | −1.30 | 1.70 | 0.136 | |
| wt | ActRIIa | 0.107 | 107 | −0.971 | 2.03 | 0.218 | |
| wt | BMPRII | 0.230 | 230 | −0.639 | 2.36 | 0.259 | |
| wt | noggin | 2.85 | 2850 | 0.455 | 3.46 | 0.894 | |
| v504 | BMPRIb | 0.0185 | 18.5 | −1.73 | 1.27 | 0.190 | 0.371 |
| v504 | ActRIIa | 0.0475 | 47.5 | −1.32 | 1.68 | 0.180 | 0.445 |
| v504 | BMPRII | 0.222 | 222 | −0.653 | 2.35 | 0.567 | 0.969 |
| v504 | noggin | 3.40 | 3400 | 0.532 | 3.53 | 2.32 | 1.19 |

TABLE 21-continued

EC50 of wild type human BMP-7 (R&D Systems) and BMP-7 variants
504, 526, and 565 for the BMP receptors BMPRIb, ActRIIa, and BMPRII and
the BMP inhibitor noggin, as determined using AlphaScreen ™ assays.

| BMP-7 variant | Receptor or inhibitor | EC(50) (ug/mL) | EC50 (ng/mL) | log(EC50) (ug/mL) | log(EC50) (ng/mL) | std. error (logEC50) ug/mL | Fold change vs. wt |
|---|---|---|---|---|---|---|---|
| v526 | BMPRIb | 0.0363 | 36.3 | −1.44 | 1.56 | 0.172 | 0.727 |
| v526 | ActRIIa | 0.0445 | 44.5 | −1.35 | 1.65 | 0.148 | 0.416 |
| v526 | BMPRII | 0.139 | 139.4 | −0.856 | 2.14 | 0.394 | 0.607 |
| v526 | noggin | 16.7 | 16700 | 1.22 | 4.22 | 11.5 | 5.83 |
| v565 | BMPRIb | 0.0224 | 22.4 | −1.65 | 1.35 | 0.121 | 0.448 |
| v565 | ActRIIa | 0.0424 | 42.4 | −1.37 | 1.63 | 0.272 | 0.397 |
| v565 | BMPRII | 0.409 | 409 | −0.388 | 2.61 | 1.02 | 1.78 |
| v565 | noggin | 0.392 | 392 | −0.407 | 2.59 | 0.471 | 0.137 |

Overall, these three variants have binding affinities that are similar to wild type. Potentially significant differences include, but are not limited to, decreased noggin affinity of v526 and increased noggin affinity of v565.

Example 16

Concentration Determination

Some of the BMP-7 variants, especially those variants with two or more mutations, exhibit reduced antibody binding affinity. As a result, ELISA concentration determination systematically underestimates the concentration of these variants. In order to obtain more accurate concentrations for these variants, as well as correction factors for the concentrations determined using ELISA, multiple concentration determination measurements were performed. Following purification, the concentration of variants 457, 471, 492, 504, 526, and 565 was assessed using the BCA assay, densitometry analysis of Coomasie blue stained mature domain following SDS-PAGE, and Western blotting using a polyclonal antibody. Wild type BMP-7 (R&D Systems) was used as a standard.

Example 17

Specific Activity Determination

The specific activity of five especially preferred BMP-7 variants was determined and compared with the specific activity of recombinant human BMP-7 purchased from R&D Systems. Equal concentrations of each protein, as determined above, were tested in the C2C12 bioassay three times.

TABLE 22

Specific activity of selected BMP-7 variants.

| Name | EC50: Exp #1 | EC50: Exp #2 | EC50: Exp #3 | Avg EC50 (ug/mL) | Std. dev. |
|---|---|---|---|---|---|
| Wild type (R&D Systems) | 2.99 | 3.53 | 2.06 | 2.86 | 0.74 |
| 565-Y65N/F93T/R129D | 0.1 | 0.3 | 0.09 | 0.16 | 0.12 |
| 526-K39S/S120D/R134E | 0.58 | 1.69 | 0.49 | 0.92 | 0.67 |
| 504-Y65N/S120D | 2.91 | nd | 4.85 | 3.88 | 1.37 |
| 492-Y65N/Y87H | 5.91 | nd | 6.18 | 6.04 | 0.19 |
| 471-K39S/N130D | 1.38 | nd | 3.99 | 2.69 | 1.85 |
| 457-K39S/F93S | 0.37 | 1.1 | nd | 0.74 | 0.52 |

Variants with the F93S and F93T substitutions were found to have increased specific activity relative to the wild type protein.

Example 18

Specific Variant Designs

Quadruple mutant containing variants were designed to improve the proteins expression yields and ensure the highest biological activities. The mutant substitutions chosen for these variants comprise a subset of total variants that either singly, or in combination improve the properties of BMP-7. The stability and yield variants were chosen a subset of mutants that show beneficial protein properties and are located at amino acid residues that do not make receptor contacts. Furin optimization is defined as a set of mutant variants, built in either the native or Y65N/S120D background that have an engineered consensus site for the furin protease required for normal processing and secretion of BMP-7. Glycosylation removal variants are mutant BMP-7 proteins, built in either the native or F93H/R134S background that contain mutations in the consensus glycosylation site, these variants are predicted to be aglycosylated. The following table summaries specific variant BMP-7 proteins created to have the listed properties:

TABLE 23

| Variant | Property |
|---|---|
| K39S_S120D_Q108D_F93S | High activity and yield |
| K39S_S120D_R129D_F93S | High activity and yield |
| K39S_S120D_Y65N_F93S | High activity and yield |
| K39S_S120D_A72D_F93S | High activity and yield |
| Y78H_R134E_Y65N_F93S | High activity and yield |
| Y78H_R134E_A72D_F93S | High activity and yield |
| K39S_S120D_Q108D_Q108D | High activity and yield |
| K39S_S120D_R129D_Q108D | High activity and yield |
| K39S_S120D_Y78H_Q108D | High activity and yield |
| K39S_S120D_R134E_Q108D | High activity and yield |
| K39S_S120D_A72D_Q108D | High activity and yield |
| Y78H_R134E_A72D_Q108D | High activity and yield |
| Y65N_R129D_M23R_Q108D | High activity and yield |
| K39S_S120D_Y65N_R129D | High activity and yield |
| K39S_S120D_Y78H_R129D | High activity and yield |
| K39S_S120D_A72D_R129D | High activity and yield |
| Y65N_R129D_M23R_S120D | High activity and yield |
| Y65N_R129D_Q108D_S120D | High activity and yield |
| K39S_S120D_Q108D_Y65N | High activity and yield |
| K39S_S120D_R129D_Y65N | High activity and yield |
| K39S_S120D_R134E_Y78H | High activity and yield |
| K39S_S120D_Q108D_R134E | High activity and yield |

TABLE 23-continued

| Variant | Property |
|---|---|
| K39S__S120D__Y65N__R134E | High activity and yield |
| K39S__S120D__Y78H__R134E | High activity and yield |
| K39S__S120D__A72D__R134E | High activity and yield |
| K39S__S120D__Q108D__M23R | High activity and yield |
| K39S__S120D__R129D__M23R | High activity and yield |
| K39S__S120D__Y78H__M23R | High activity and yield |
| K39S__S120D__R134E__M23R | High activity and yield |
| K39S__S120D__A72D__M23R | High activity and yield |
| Y78H__R134E__Y65N__M23R | High activity and yield |
| Y78H__R134E__A72D__M23R | High activity and yield |
| Y65N__R129D__Q108D__M23R | High activity and yield |
| Q108D__A72D | Stability and yield |
| S120D__A72D | Stability and yield |
| R129D__A72D | Stability and yield |
| A135E__A72D | Stability and yield |
| A72D__Q108D | Stability and yield |
| S120D__Q108D | Stability and yield |
| Q108D__S120D | Stability and yield |
| A135E__S120D | Stability and yield |
| A72D__R129D | Stability and yield |
| Q108D__R129D | Stability and yield |
| S120D__R129D | Stability and yield |
| Q108D__A135E | Stability and yield |
| S120D__A135E | Stability and yield |
| A72D__F93S | Stability and yield |
| A72D__A105V | Stability and yield |
| A72D__N110D | Stability and yield |
| A72D__A135S | Stability and yield |
| A72D__H139R | Stability and yield |
| F93S__A105V | Stability and yield |
| F93S__Q108D | Stability and yield |
| F93S__N110D | Stability and yield |
| F93S__S120D | Stability and yield |
| F93S__R129D | Stability and yield |
| F93S__R134E | Stability and yield |
| F93S__A135S | Stability and yield |
| F93S__H139R | Stability and yield |
| A105V__S120D | Stability and yield |
| A105V__R129D | Stability and yield |
| A105V__R134E | Stability and yield |
| A105V__A135S | Stability and yield |
| A105V__H139R | Stability and yield |
| N110D__S120D | Stability and yield |
| N110D__R129D | Stability and yield |
| N110D__R134E | Stability and yield |
| N110D__A135S | Stability and yield |
| N110D__H139R | Stability and yield |
| Q108D__R134E | Stability and yield |
| Q108D__A135S | Stability and yield |
| Q108D__H139R | Stability and yield |
| F117Y__R129D | Stability and yield |
| F117Y__R134E | Stability and yield |
| S120D__R134E | Stability and yield |
| S120D__A135S | Stability and yield |
| S120D__H139R | Stability and yield |
| L21G__E42D | Stability and yield |
| L21G__T98K | Stability and yield |
| L21G__A105V | Stability and yield |
| L21G__S120D | Stability and yield |
| L21G__A135S | Stability and yield |
| L21G__A135E | Stability and yield |
| L21G__H139R | Stability and yield |
| M23R__E42D | Stability and yield |
| M23R__T98K | Stability and yield |
| M23R__A105V | Stability and yield |
| M23R__S120D | Stability and yield |
| M23R__A135S | Stability and yield |
| M23R__A135E | Stability and yield |
| M23R__H139R | Stability and yield |
| E42D__T98K | Stability and yield |
| E42D__A105V | Stability and yield |
| E42D__S120D | Stability and yield |
| E42D__A135S | Stability and yield |
| E42D__A135E | Stability and yield |
| E42D__H139R | Stability and yield |
| T98K__A105V | Stability and yield |
| T98K__S120D | Stability and yield |

TABLE 23-continued

| Variant | Property |
|---|---|
| T98K__A135S | Stability and yield |
| T98K__A135E | Stability and yield |
| T98K__H139R | Stability and yield |
| A105V__S120D | Stability and yield |
| A105V__A135S | Stability and yield |
| A105V__A135E | Stability and yield |
| A105V__H139R | Stability and yield |
| S120D__A135S | Stability and yield |
| S120D__A135E | Stability and yield |
| S120D__H139R | Stability and yield |
| WT__P1__QVKKRSKR | Furin optimization |
| WT__P2__QVKKRSRR | Furin optimization |
| WT__P3__QVRKRSKR | Furin optimization |
| WT__P4__QVRKRSRR | Furin optimization |
| WT__P5__KVKKRSKR | Furin optimization |
| WT__P6__KVKKRSRR | Furin optimization |
| WT__P7__KVRKRSKR | Furin optimization |
| WT__P8__KVRKRSRR | Furin optimization |
| WT__P9__EVKLRSKR | Furin optimization |
| WT__P10__EVKLRSRR | Furin optimization |
| WT__P11__EVRLRSKR | Furin optimization |
| WT__P12__EVRLRSRR | Furin optimization |
| Y65N__S120D__QVKKRSKR | Furin optimization |
| Y65N__S120D__QVKKRSRR | Furin optimization |
| Y65N__S120D__QVRKRSKR | Furin optimization |
| Y65N__S120D__QVRKRSRR | Furin optimization |
| Y65N__S120D__KVKKRSKR | Furin optimization |
| Y65N__S120D__KVKKRSRR | Furin optimization |
| Y65N__S120D__KVRKRSKR | Furin optimization |
| Y65N__S120D__KVRKRSRR | Furin optimization |
| Y65N__S120D__EVKLRSKR | Furin optimization |
| Y65N__S120D__EVKLRSRR | Furin optimization |
| Y65N__S120D__EVRLRSKR | Furin optimization |
| Y65N__S120D__EVRLRSRR | Furin optimization |
| N80A | Glycosylation removal |
| N80C | Glycosylation removal |
| N80D | Glycosylation removal |
| N80E | Glycosylation removal |
| N80F | Glycosylation removal |
| N80G | Glycosylation removal |
| N80H | Glycosylation removal |
| N80I | Glycosylation removal |
| N80K | Glycosylation removal |
| N80L | Glycosylation removal |
| N80M | Glycosylation removal |
| N80P | Glycosylation removal |
| N80Q | Glycosylation removal |
| N80R | Glycosylation removal |
| N80S | Glycosylation removal |
| N80T | Glycosylation removal |
| N80V | Glycosylation removal |
| N80W | Glycosylation removal |
| N80Y | Glycosylation removal |
| A81P | Glycosylation removal |
| T82A | Glycosylation removal |
| T82D | Glycosylation removal |
| T82E | Glycosylation removal |
| T82F | Glycosylation removal |
| T82G | Glycosylation removal |
| T82H | Glycosylation removal |
| T82I | Glycosylation removal |
| T82K | Glycosylation removal |
| T82L | Glycosylation removal |
| T82M | Glycosylation removal |
| T82N | Glycosylation removal |
| T82P | Glycosylation removal |
| T82Q | Glycosylation removal |
| T82R | Glycosylation removal |
| T82V | Glycosylation removal |
| T82W | Glycosylation removal |
| T82Y | Glycosylation removal |
| F93H/R134S/N80A | Glycosylation removal |
| F93H/R134S/N80C | Glycosylation removal |
| F93H/R134S/N80D | Glycosylation removal |
| F93H/R134S/N80E | Glycosylation removal |
| F93H/R134S/N80F | Glycosylation removal |
| F93H/R134S/N80G | Glycosylation removal |

TABLE 23-continued

| Variant | Property |
|---|---|
| F93H/R134S/N80H | Glycosylation removal |
| F93H/R134S/N80I | Glycosylation removal |
| F93H/R134S/N80K | Glycosylation removal |
| F93H/R134S/N80L | Glycosylation removal |
| F93H/R134S/N80M | Glycosylation removal |
| F93H/R134S/N80P | Glycosylation removal |
| F93H/R134S/N80Q | Glycosylation removal |
| F93H/R134S/N80R | Glycosylation removal |
| F93H/R134S/N80S | Glycosylation removal |
| F93H/R134S/N80T | Glycosylation removal |
| F93H/R134S/N80V | Glycosylation removal |
| F93H/R134S/N80W | Glycosylation removal |
| F93H/R134S/N80Y | Glycosylation removal |
| F93H/R134S/A81P | Glycosylation removal |
| F93H/R134S/T82A | Glycosylation removal |
| F93H/R134S/T82D | Glycosylation removal |
| F93H/R134S/T82E | Glycosylation removal |
| F93H/R134S/T82F | Glycosylation removal |
| F93H/R134S/T82G | Glycosylation removal |
| F93H/R134S/T82H | Glycosylation removal |
| F93H/R134S/T82I | Glycosylation removal |
| F93H/R134S/T82K | Glycosylation removal |
| F93H/R134S/T82L | Glycosylation removal |
| F93H/R134S/T82M | Glycosylation removal |
| F93H/R134S/T82N | Glycosylation removal |
| F93H/R134S/T82P | Glycosylation removal |
| F93H/R134S/T82Q | Glycosylation removal |
| F93H/R134S/T82R | Glycosylation removal |
| F93H/R134S/T82V | Glycosylation removal |
| F93H/R134S/T82W | Glycosylation removal |
| F93H/R134S/T82Y | Glycosylation removal |

Example 18

Variant Designs

In addition to the preferred embodiments disclosed in Table 23 above, the following variants are also preferred embodiments of the present invention:

TABLE 24

L21G_V26G
L21G_V26N
L21G_M23G
L21N_M23G
M23G_V26G
M23G_V26N
21N_23G_26G
A105V
A111D
A111S
A135D
A135E
A135S
A37E
A63E
A63Q
A63R
A63S
A72D
A72E
A72H
A72K
A72N
A72R
A72S
A105V
D119E
D119N
D119S
D119T

TABLE 24-continued

D49S
D54K
D54N
D54S
E42D
E42Q
E42R
E42T
E60H
E60K
E60N
E60P
R60Q
E60R
E60R
E60R
E60S
E60T
E70A
E70Q
E97D
E97K
E97R
F117A
F117D
F117E
F117H
F117K
F117Q
F117R
F117S
F117Y
F73A
F73A
F73D
F73E
F73G
F73G
F73H
F73K
F73N
F73Q
F73R
F73S
F73T
F73T
F93A
F93D
F93E
F93G
F93H
F93H_A105V
F93H_A135E
F93H_A72D
F93H_F117Y
F93H_H139R
F93H_I57L
F93H_I94R
F93H_K127E
F93H_K39A
F93H_K39S
F93H_L21G
F93H_L21R
F93H_N130D
F93H_Q108D
F93H_R129D
F93H_R134E
F93H_R134S
F93H_R48N
F93H_S120D
F93H_Y128D
F93H_Y78R
F93K
F93P
F93Q
F93R
F93S
F93T
H139R

TABLE 24-continued

I124A
I124D
I124E
I124K
I124N
I124Q
I124R
I124S
I124T
I124V
I57A
I57D
I57E
I57H
I57I
I57K
I57L
I57N
I57P
I57Q
I57T
I57V
I86A
I86D
I86D
I86E
I86K
I86P
I86Q
I86T
I94A
I94E
I94H
I94K
I94K
I94P
I94Q
I94R
I94T
K126D
K126E
K126G
K126Q
K126R
K127A
K127D
K127E
K127E
K127H
K127N
K127P
K127Q
K127S
K127T
K127Y
K39A
K39A
K39D
K39E
K39G
K39N
K39R
K39S
K39S_A135E
K39S_A135S
K39S_A72D
K39S_F117H
K39S_F117Y
K39S_F93S
K39S_H139R
K39S_I57L
K39S_I86A
K39S_I94R
K39S_L21G
K39S_L21R
K39S_M23R
K39S_N110D
K39S_N130D
K39S_Q108D

TABLE 24-continued

K39S_Q53G
K39S_Q53T
K39S_R129D
K39S_R134E
K39S_R134S
K39S_R48N
K39S_S120D
K39S_S120D_A72D
K39S_S120D_F93H
K39S_S120D_F93S
K39S_S120D_H139R
K39S_S120D_L21G
K39S_S120D_M23R
K39S_S120D_Q108D
K39S_S120D_R129D
K39S_S120D_R134E
K39S_S120D_Y65N
K39S_S120D_Y78H
K39S_Y116H
K39S_Y128D
K39S_Y65N
K39S_Y78R
K39T
L115A
L115E
L115K
L115Q
L115T
L125A
L125E
L125K
L125P
L125Q
L125T
L125Y
L21D
L21E
L21G
L21G
L21H
L21K
L21N
L21N_M23G_V26N
L21R
L21S
L90A
L90E
L90G
L90H
L90K
L90L
L90N
L90P
L90P
L90Q
L90R
L90R
L90R
L90S
L90T
M23D
M23G
M23K
M23N
M23R
M23S
N110D
N110E
N110H
N122E
N122Q
N122R
N130D
N76A
N76D
N76N
N76S
N76T
N76Y

TABLE 24-continued

N83P
N95D
N95K
N95Q
N95R
Q108D
Q108K
Q108S
Q36E
Q36N
Q53A
Q53D
Q53E
Q53G
Q53H
Q53K
Q53R
Q53S
Q53T
Q53T
Q88E
R129D
R129E
R129K
R129N
R129S
R134D
R134E
R134K
R134L
R134P
R134P
R134Q
R134R
R134R
R134S
R48D
R48E
R48H
R48N
R48Q
S113D
S113E
S120D
S120E
S120N
S120R
S121D
S121E
S121K
S121N
S121T
S77A
S77A
S77A
S77D
S77E
S77H
S77K
S77N
S77P
S77P
S77Q
S77T
S77T
T107D
T107E
T98A
T98Del
T98E
T98E
T98K
V123A
V123A
V123D
V123G
V123G
V123N
V123N

TABLE 24-continued

V123R
V123T
V123V
V26D
V26E
V26G
V26K
V26K
V26N
V26S
V26V
W52A
W52E
W52K
W52P
W52Q
W52T
W55A
W55A
W55E
W55H
W55K
W55N
W55P
W55Q
W55R
W55T
Y116A
Y116D
Y116E
Y116H
Y116K
Y116Q
Y116S
Y116T
Y116Y
Y128D
Y128E
Y128H
Y128K
Y128Q
Y44A
Y44D
Y44E
Y44G
Y44H
Y44K
Y44N
Y44P
Y44Q
Y44R
Y44S
Y44T
Y65D
Y65E
Y65N
Y65N_A105V
Y65N_A135E
Y65N_A135S
Y65N_F117Y
Y65N_F93H
Y65N_F93T
Y65N_H139R
Y65N_I57L
Y65N_I94R
Y65N_K127E
Y65N_K39A
Y65N_K39S
Y65N_L21G
Y65N_L21R
Y65N_M23N
Y65N_M23R
Y65N_Q108D
Y65N_Q53D
Y65N_Q53G
Y65N_Q53S
Y65N_Q53T
Y65N_R129D
Y65N_R129D_F117H

TABLE 24-continued

Y65N_R129D_F117Y
Y65N_R129D_F93H
Y65N_R129D_F93S
Y65N_R129D_F93T
Y65N_R129D_K39A
Y65N_R129D_K39S
Y65N_R129D_L21G
Y65N_R129D_M23R
Y65N_R129D_Q108D
Y65N_R129D_S120D
Y65N_R129D_Y78H
Y65N_R134E
Y65N_R134S
Y65N_S120D
Y65N_Y128D
Y65N_Y78H
Y65N_Y78R
Y78A
Y78D
Y78G
Y78H
Y78H_A105V
Y78H_A135E
Y78H_A135S
Y78H_A63S
Y78H_A72D
Y78H_F117H
Y78H_F117Y
Y78H_F93H
Y78H_F93H_A72D
Y78H_F93H_F117H
Y78H_F93H_F117Y
Y78H_F93H_H139R
Y78H_F93H_K39A
Y78H_F93H_K39S
Y78H_F93H_L21G
Y78H_F93H_M23R
Y78H_F93H_Q108D
Y78H_F93H_R129D
Y78H_F93H_R134S
Y78H_F93H_S120D
Y78H_F93H_Y65N
Y78H_F93T
Y78H_H139R
Y78H_I57L

TABLE 24-continued

Y78H_I94R
Y78H_K127E
Y78H_K39S
Y78H_L21R
Y78H_N110D
Y78H_N130D
Y78H_Q108D
Y78H_Q53G
Y78H_Q53S
Y78H_R129D
Y78H_R134E
Y78H_R134E_A72D
Y78H_R134E_F117Y
Y78H_R134E_F93H
Y78H_R134E_F93S
Y78H_R134E_F93T
Y78H_R134E_K39A
Y78H_R134E_K39S
Y78H_R134E_L21G
Y78H_R134E_M23R
Y78H_R134E_Q108D
Y78H_R134E_S120D
Y78H_R134E_Y65N
Y78H_R134S
Y78H_R48N
Y78H_S120D
Y78H_Y116H
Y78H_Y128D
Y78N
Y78P
Y78R
Y78S
Y78T
Y78Y

While the foregoing invention has been described above, it will be clear to one skilled in the art that various changes and additional embodiments made be made without departing from the scope of the invention. All publications, patents, patent applications (provisional, utility and PCT) or other documents cited herein are incorporated by references in their entirety.

We claim:

1. A non-naturally occurring variant BMP-7 protein comprising amino acid D at position Vb(120) of the sequence: Fx(1-20)-Vb(21)-Fx(22-38)-Vb(39)-Fx(40-64)-Vb(65)-Fx(66-71)-Vb(72)-Fx(73-77)-Vb(78)-Fx(79-92)-Vb(93)-Fx(94-119)-Vb(120)-Fx(121-134)-Vb(135) whereinFx(1-20) corresponds to amino acid residues 1-20 of human BMP-7 (SEQ ID NO:5); Vb(21) is selected from the group consisting of L and G; Fx(22-38) corresponds to amino acid residues 22-38 of human BMP-7 (SEQ ID NO:5); Vb(39) is selected from the group consisting of K, A and S; Fx(40-64) corresponds to amino acid residues 40-64 of human BMP-7 (SEQ ID NO:5); Vb(65) is selected from the group consisting of Y and N; Fx(66-71) corresponds to amino acid residues 66-71 of human BMP-7 (SEQ ID NO:5); Vb(72) is selected from the group consisting of A and D; Fx(73-77) corresponds to amino acid residues 73-77 of human BMP-7 (SEQ ID NO:5); Vb(78) is selected from the group consisting of Y and H; Fx(79-92) corresponds to amino acid residues 79-92 of human BMP-7 (SEQ ID NO:5); Vb(93) is selected from the group consisting of F, H, S and T; Fx(94-119) corresponds to amino acid residues 94-119 of human BMP-7 (SEQ ID NO:5); Fx(121-134) corresponds to amino acid residues 121-134 of human BMP-7 (SEQ ID NO:5); Vb(135) is selected from the group consisting of A and E; wherein said variant comprises an amino acid substitution as compared to human BMP-7 (SEQ ID NO:5), wherein said variant retains at least 50% bioactivity relative to human BMP-7 (SEQ ID NO:5), as determined by differentiation of C2C12 cells as measured by alkaline phosphatase activity, and, wherein said variant BMP-7 protein differs from human BMP-7 (SEQ ID NO:5) by 1, 2, 3, 4 or 5 residues.

2. A variant BMP-7 protein comprising the substitution S210D as compared to human BMP-7 (SEQ ID NO:5), wherein said variant retains at least 50% bioactivity relative to human BMP-7 (SEQ ID NO:5), as determined by differentiation of C2C12 cells as measured by alkaline phosphatase activity, and wherein said variant BMP-7 protein differs from human BMP-7 (SEQ ID NO:5) by 1, 2, 3, 4 or 5 residues.

* * * * *